(12) United States Patent
Chen

(10) Patent No.: US 12,291,534 B2
(45) Date of Patent: *May 6, 2025

(54) AMINONORBORNANE DERIVATIVE AND MANUFACTURE METHOD THEREFOR AND USE THEREOF

(71) Applicant: TRANSTHERA SCIENCES (NANJING), INC., Jiangsu (CN)

(72) Inventor: Rongyao Chen, Jiangsu (CN)

(73) Assignee: TRANSTHERA SCIENCES (NANJING), INC., Jiangsu (CN)

( * ) Notice: Subject to any disclaimer, the term of this patent is extended or adjusted under 35 U.S.C. 154(b) by 840 days.

This patent is subject to a terminal disclaimer.

(21) Appl. No.: 17/279,751

(22) PCT Filed: Jul. 5, 2019

(86) PCT No.: PCT/CN2019/094864
§ 371 (c)(1),
(2) Date: Mar. 25, 2021

(87) PCT Pub. No.: WO2020/063012
PCT Pub. Date: Apr. 2, 2020

(65) Prior Publication Data
US 2021/0332057 A1 Oct. 28, 2021

(30) Foreign Application Priority Data
Sep. 29, 2018 (CN) .................. 201811153123.3

(51) Int. Cl.
*C07D 487/04* (2006.01)
*A61P 35/00* (2006.01)

(52) U.S. Cl.
CPC ............ *C07D 487/04* (2013.01); *A61P 35/00* (2018.01)

(58) Field of Classification Search
CPC ........ C07D 487/04; A61P 35/00; A61P 11/06; A61P 29/00; A61P 35/02; A61P 37/02; A61P 37/00; A61K 31/5377; A61K 31/4985
See application file for complete search history.

(56) References Cited

U.S. PATENT DOCUMENTS

| 2008/0076921 A1 * | 3/2008 | Honigberg ................ A61P 1/04 435/194 |
| 2016/0200730 A1 | 7/2016 | He |
| 2016/0237075 A1 | 8/2016 | Chen et al. |
| 2017/0008899 A1 | 1/2017 | De Man et al. |

FOREIGN PATENT DOCUMENTS

| CN | 1898240 A | 1/2007 |
| CN | 106831789 A | 6/2017 |
| CN | 107602564 A | 1/2018 |
| EA | 201692176 A1 | 5/2019 |
| JP | 2014-520866 A | 8/2014 |
| JP | 2015-509927 A | 4/2015 |
| JP | 2016-501191 A | 1/2016 |
| JP | 2018-527384 A | 9/2018 |
| RU | 2016115803 A | 5/2019 |
| WO | 2016/019233 A1 | 2/2016 |
| WO | 2016/109222 A1 | 7/2016 |
| WO | 2016/109223 A1 | 7/2016 |

OTHER PUBLICATIONS

Stella. J. Pharmaceutical Sciences, 2010, 99(12), pp. 4755-4765 (Year: 2010).*
Phillips, Journal of Aerosol Medicine and Pulmonary Drug Delivery, vol. 29, No. 3, 2016 (Year: 2016).*
International Search Report for International Application PCT/CN2019/094864, dated Sep. 20, 2019.

* cited by examiner

*Primary Examiner* — Susanna Moore
*Assistant Examiner* — Luisalberto Gonzalez
(74) *Attorney, Agent, or Firm* — The Dobrusin Law Firm, P.C.

(57) ABSTRACT

The present invention relates to a compound of formula I or a pharmaceutically acceptable salt, a solvate, an active metabolite, a polymorph, an ester, an optical isomer or a prodrug thereof, a pharmaceutical composition comprising the compound of formula I, and use of the compound, as a Bruton's tyrosine kinase inhibitor with high selectivity for BTK(C481S) mutant, in the manufacture of a medicament for preventing or treating a heteroimmune disease, an autoimmune disease or a cancer.

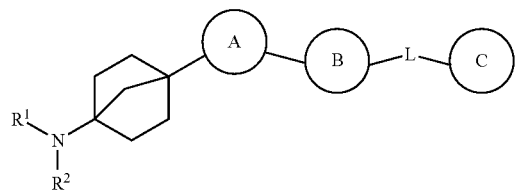

Formula I

16 Claims, 1 Drawing Sheet

AMINONORBORNANE DERIVATIVE AND MANUFACTURE METHOD THEREFOR AND USE THEREOF

TECHNICAL FIELD

The present invention belongs to the field of medicine, and particularly relates to an aminonorbornane derivative as a Bruton's tyrosine kinase inhibitor with high selectivity for a C481S mutant, a pharmaceutical composition thereof, a manufacture method therefor and use thereof in the manufacture of a medicament.

BACKGROUND

B-cell receptor (BCR) signaling pathway plays a key role in the maturation, differentiation and development of B cells. Aberrant BCR-mediated signal transduction may lead to deregulated B cell activation and/or formation of pathogenic autoantibodies, resulting in a variety of human diseases including cancer, autoimmune diseases including lupus erythematosus, chronic lymphocytic lymphoma, diffuse large cell lymphoma, follicular lymphoma or chronic lymphocytic leukemia, heteroimmune diseases including inflammatory diseases, asthma, and the like.

Bruton's tyrosine kinase (BTK) is a member of the TEC family of non-receptor tyrosine kinases. It plays a key role in the activation of the BCR signaling pathway, and is a key regulator of early B-cell formation and mature B-cell activation and survival (Khan et al., *Immunity* 1995 3:283; Ellmeier et al., *J Exp Med* 2000 192:1611). BTK plays an important role in regulating B-cell proliferation and apoptosis (Islam and Smith, *Immunol Rev* 2000 178:49; Davis et al., *Nature* 2010 463:88-94), and therefore inhibition of BTK can be used to treat certain B-cell lymphomas and leukemia (Feldhahn et al., *J Exp Med* 2005 201:1837).

The role of BTK in autoimmune and inflammatory diseases has been confirmed by BTK-deficient mouse models. In a preclinical mouse model of systemic lupus erythematosus (SLE), BTK-deficient mice show significant improvement in progressive disease. In addition, BTK-deficient mice are resistant to collagen-induced arthritis (Jansson and Holmdahl, *Clin Exp Immunol* 1993 94:459). Selective BTK inhibitors show a clear dose-effect relationship in mouse models of arthritis (Pan et al., *Chem. Med. Chem.* 2007 2:58-61). Clinical studies are currently underway for the treatment of arthritis with BTK inhibitors.

As the first marketed BTK inhibitor, ibrutinib (trade name Imbruvica) has had great success with its annual sales reaching 2.6 billion US dollars in 2017. However, as with many other anticancer drugs, some patients exhibit resistance to the drug. C481S mutation of BTK kinase has been found to be the main cause of drug resistance. Ibrutinib acts pharmacodynamically by irreversible covalent binding to C481 tryptophan residue of BTK kinase; however, the tryptophan residue loses the ability to covalently binding to ibrutinib as C481S mutation changes tryptophan into serine.

According to clinical statistics, BTK(C481S) mutation is associated with 87% of patients with relapsed chronic lymphoma (CLL) (Woyach et al., *J. Clin Oncol* 2017 35:1437-1443) and about 80% of patients with relapsed mantle cell lymphoma (MCL) (Chiron et al., *Cancer Discovery* 2014 4(9): 1-14). The development of a BTK inhibitor that is effective against BTK(C481S) mutant would overcome the resistance to ibrutinib due to the C481S mutation.

SUMMARY

The technical problem to be solved by the prevent invention is to provide a novel and undisclosed compound of Bruton's tyrosine kinase inhibitor with high selectivity for BTK(C481S) mutant, a pharmaceutically acceptable salt, a solvate, an active metabolite, a polymorph, an ester, an optical isomer or a prodrug thereof, use of the compound in pharmacy and a method for preventing or treating diseases related to excessive BTK activity in human or mammals by using the compound disclosed herein.

In order to solve the technical problem, the technical scheme adopted in the present invention is as follows:

Provided is a compound of formula (I)

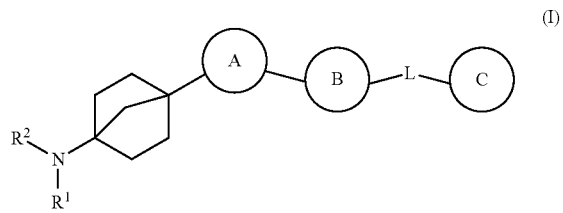

or a pharmaceutically acceptable salt, a solvate, an active metabolite, a polymorph, an ester, an optical isomer or a prodrug thereof, wherein ring A is selected from one of the following structures:

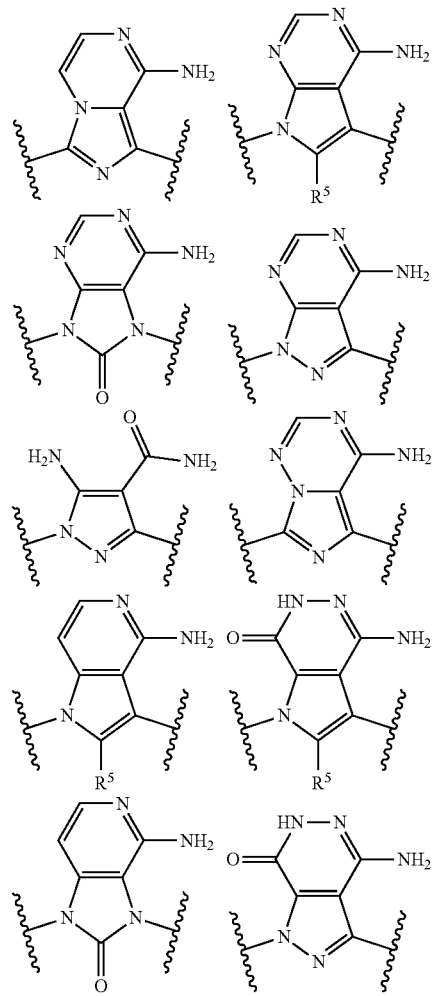

-continued

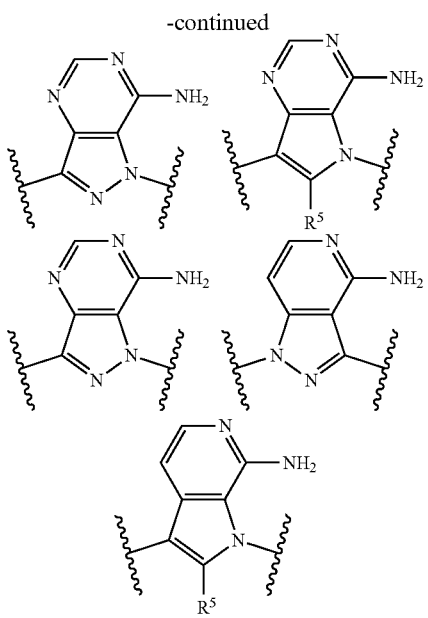

R⁵ being selected from hydrogen, halogen, cyano, hydroxyl, alkynyl, amino, $C_{1-3}$ alkyl, $C_{1-3}$ alkoxy, $C_{1-3}$ haloalkyl, $C_{1-3}$ haloalkoxy, $C_{1-3}$ haloalkylamino, $C_{3-7}$ cycloalkyl, $C_{1-3}$ cycloalkoxy and $C_{3-7}$ cycloalkylamino;

ring B is a substituted or unsubstituted aromatic ring or heteroaromatic ring; ring C is a substituted or unsubstituted aromatic ring or heteroaromatic ring;

L is a single bond or one of the following structures:

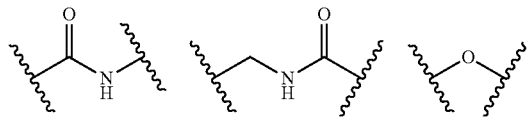

R¹ is selected from R³ and one of the following structures:

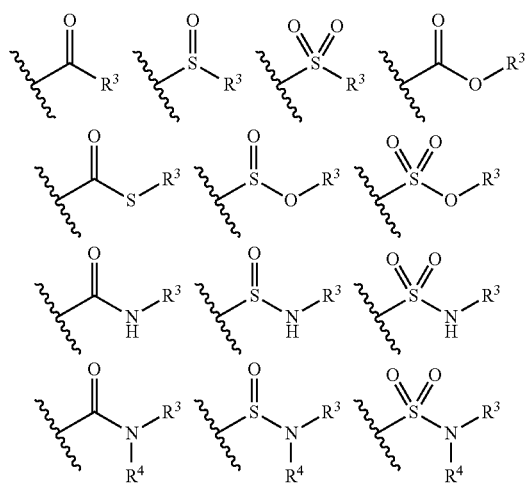

R³ being selected from hydrogen, substituted or unsubstituted $C_{1-6}$ alkyl, substituted or unsubstituted $C_{1-6}$ alkynyl, substituted or unsubstituted $C_{1-6}$ alkenyl, substituted or unsubstituted $C_{6-10}$ aryl, substituted or unsubstituted $C_{1-9}$ heteroaryl, substituted or unsubstituted $C_{3-7}$ cycloalkyl, and substituted or unsubstituted $C_{2-7}$ heterocycloalkylamino; and R⁴ being selected from hydrogen, substituted or unsubstituted $C_{1-6}$ alkyl, substituted or unsubstituted $C_{6-10}$ aryl, substituted or unsubstituted $C_{1-9}$ heteroaryl, substituted or unsubstituted $C_{3-7}$ cycloalkyl, and substituted or unsubstituted $C_{3-7}$ heterocycloalkyl; and R² is selected from H, substituted or unsubstituted $C_{1-3}$ alkyl, substituted or unsubstituted $C_{3-7}$ cycloalkyl, substituted or unsubstituted $C_{2-7}$ heterocycloalkyl, substituted or unsubstituted $C_{6-10}$ aryl, and substituted or unsubstituted $C_{1-9}$ heteroaryl.

R¹ and R², along with N attached thereto, form a substituted or unsubstituted $C_{2-7}$ heterocyclic ring, and R³ and R4, along with N attached thereto, form or do not form a $C_{3-7}$ heterocyclylamino or a $C_{3-9}$ heteroarylamino.

Preferably, for R³, a substituent of the substituted $C_{1-6}$ alkyl, the substituted $C_{1-6}$ alkynyl, the substituted $C_{1-6}$ alkenyl, the substituted $C_{6-10}$ aryl, the substituted $C_{1-9}$ heteroaryl, the substituted $C_{3-7}$ cycloalkyl or the substituted $C_{2-7}$ heterocycloalkyl is selected from one or more of halogen, cyano, hydroxyl, amino, substituted or unsubstituted acylamino, substituted or unsubstituted aminoacyl, substituted or unsubstituted $C_{1-4}$ alkyl, substituted or unsubstituted $C_{3-7}$ cycloalkyl, substituted or unsubstituted $C_{3-7}$ cycloalkoxy, substituted or unsubstituted $C_{1-4}$ alkylamino, di[substituted or unsubstituted $C_{1-4}$ alkyl]amino, substituted or unsubstituted $C_{3-7}$ cycloalkylamino, substituted or unsubstituted $C_{3-7}$ heterocycloalkylamino, substituted or unsubstituted $C_{1-3}$ alkoxy, substituted or unsubstituted $C_{3-7}$ cycloalkoxy, substituted or unsubstituted $C_{6-10}$ aryl, and substituted or unsubstituted $C_{3-7}$ heterocycloalkyl.

Preferably, for R⁴, a substituent of the substituted $C_{1-4}$ alkyl, the substituted $C_{6-10}$ aryl, the substituted $C_{1-9}$ heteroaryl, the substituted $C_{3-7}$ cycloalkyl or the substituted $C_{3-7}$ heterocycloalkyl is selected from one or more of halogen, hydroxyl, cyano, amino, substituted or unsubstituted $C_{1-4}$ alkenyl, substituted or unsubstituted $C_{3-7}$ cycloalkyl, substituted or unsubstituted $C_{3-7}$ cycloalkoxy, substituted or unsubstituted $C_{1-4}$ alkylamino, di[substituted or unsubstituted $C_{1-4}$ alkyl]amino, substituted or unsubstituted $C_{3-7}$ cycloalkylamino, substituted or unsubstituted $C_{3-7}$ heterocycloalkylamino, substituted or unsubstituted $C_{1-3}$ alkoxy, substituted or unsubstituted $C_{3-7}$ cycloalkoxy, substituted or unsubstituted $C_{6-10}$ aryl, and substituted or unsubstituted $C_{3-7}$ heterocycloalkyl.

Preferably, ring A is one of the following structures:

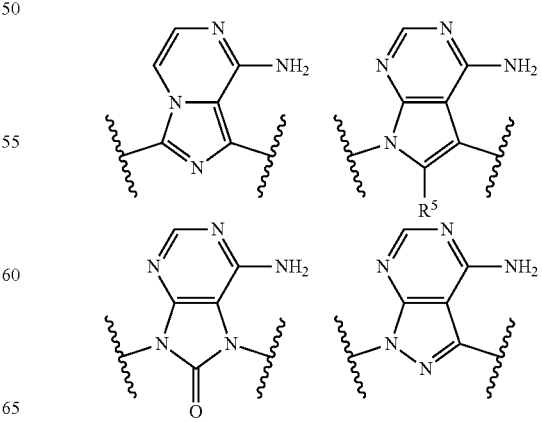

R[5] being selected from hydrogen, halogen, cyano, hydroxyl, alkynyl, amino, $C_{1-3}$ alkyl, $C_{1-3}$ alkoxy, $C_{1-3}$ haloalkyl, $C_{1-3}$ haloalkoxy, $C_{1-3}$ haloalkylamino. $C_{3-7}$ cycloalkyl, $C_{3-7}$ cycloalkoxy and $C_{3-7}$ cycloalkylamino;

preferably, for ring B, a substituent of the substituted aromatic ring or heteroaromatic ring is selected from one or more of halogen, hydroxyl, cyano, amino, $C_{1-3}$, alkyl, $C_{1-3}$ alkoxy, $C_{1-3}$ haloalkyl and $C_{1-3}$ haloalkoxy.

Preferably, ring B is one of the following structures:

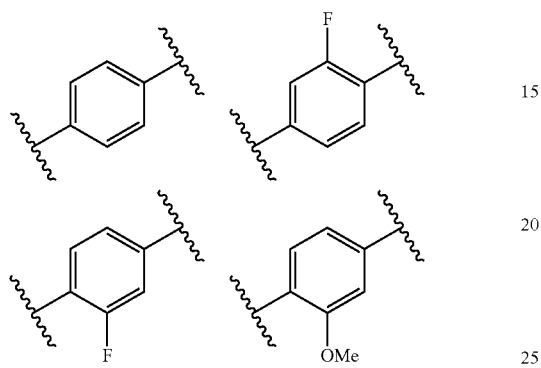

Preferably, for ring C, a substituent of the substituted aromatic ring or heteroaromatic ring is selected from one or more of halogen, hydroxyl, cyano, amino, $C_{1-3}$ alkyl, $C_{1-3}$ alkoxy, $C_{1-3}$ haloalkyl and $C_{1-3}$ haloalkoxy.

Preferably, ring C is one of the following structures:

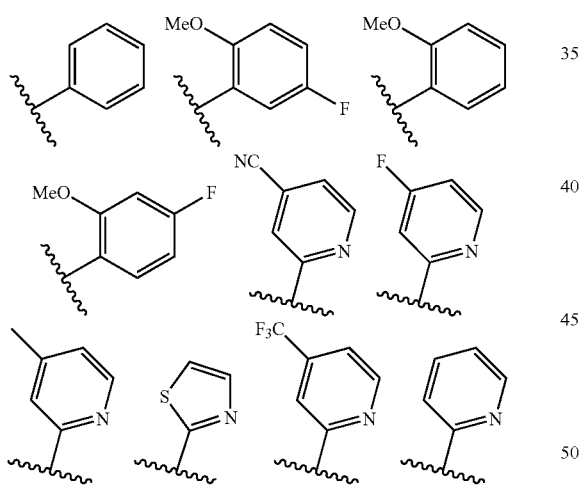

Preferably, R[2] is selected from H, and R[1] is selected from

wherein R[3] is selected from hydrogen, substituted or unsubstituted $C_{1-6}$ alkyl, substituted or unsubstituted $C_{1-6}$ alkynyl, substituted or unsubstituted $C_{1-6}$ alkenyl, substituted or unsubstituted $C_{6-10}$ aryl, substituted or unsubstituted $C_{1-9}$ heteroaryl, substituted or unsubstituted $C_{6-10}$ cycloalkyl, and substituted or unsubstituted $C_{2-7}$ heterocycloalkylamino.

Most preferably, the compound is selected from any one of the following structures:

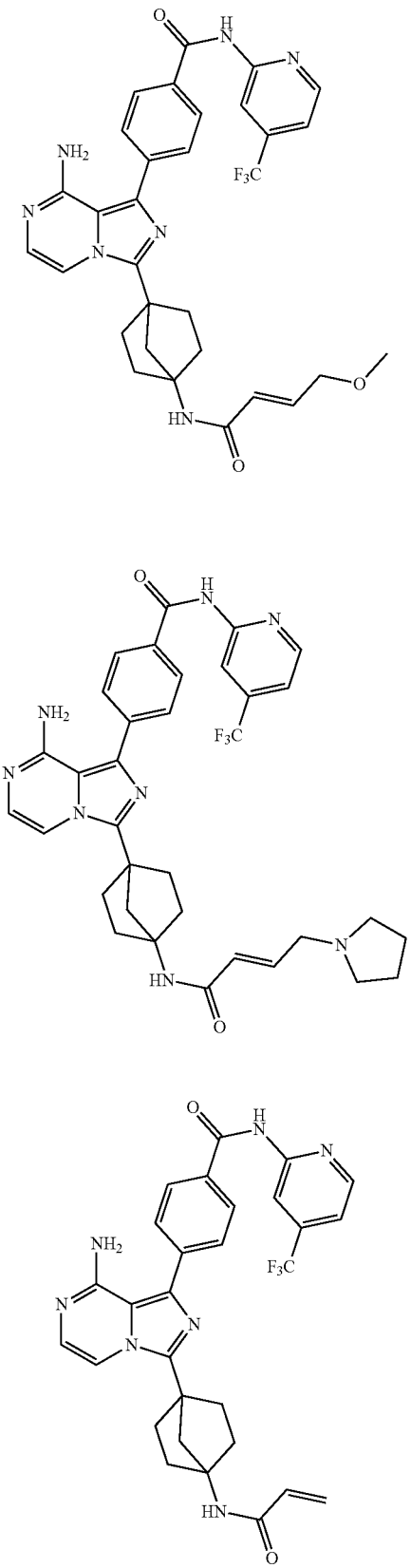

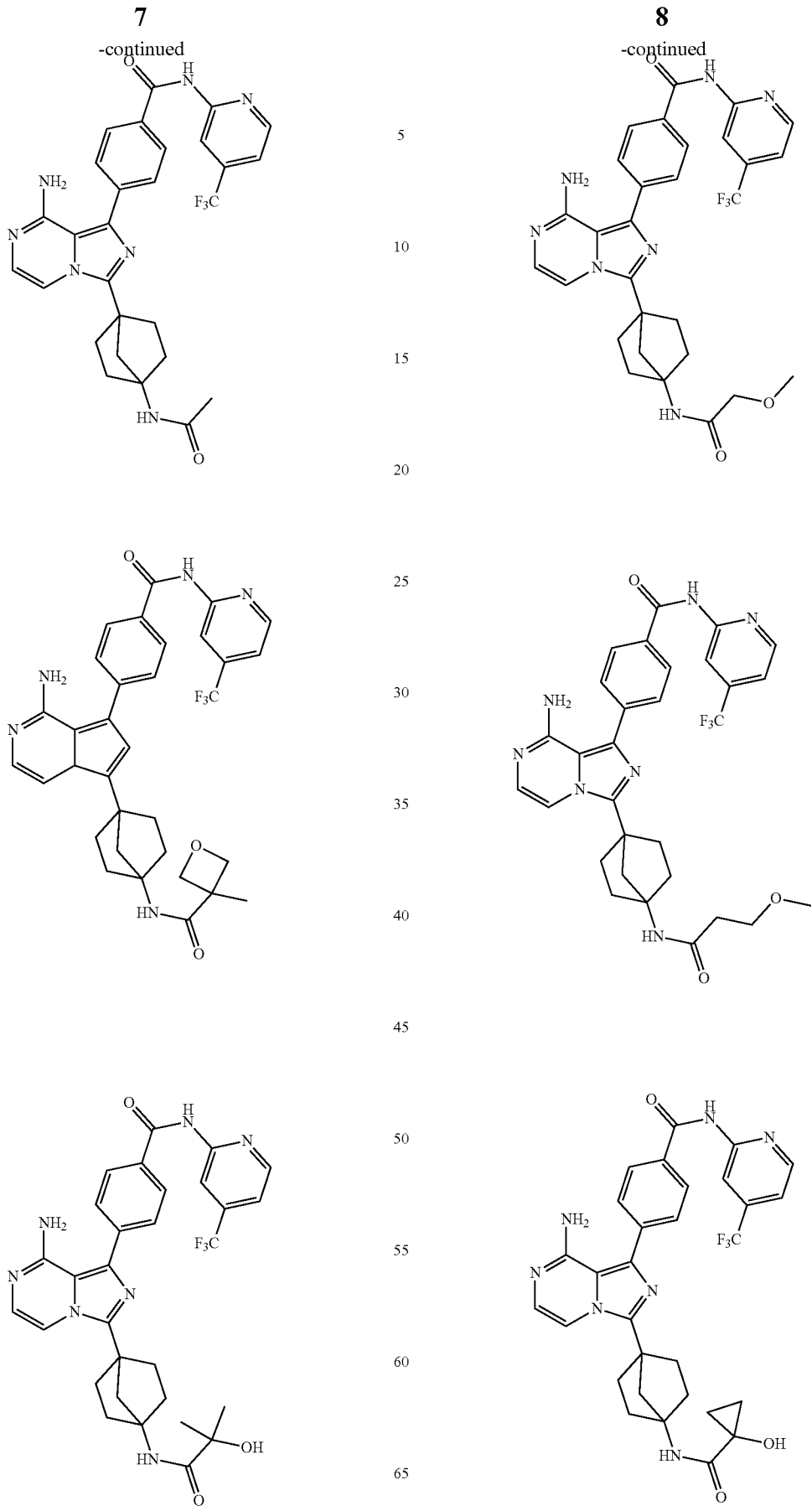

-continued
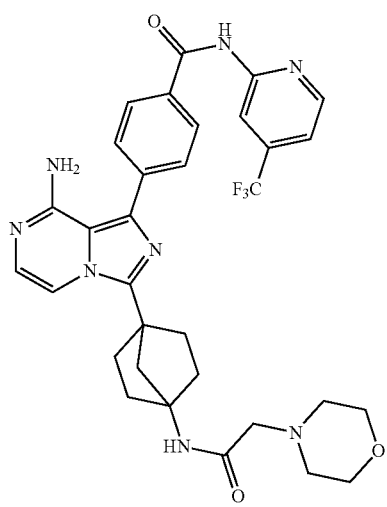
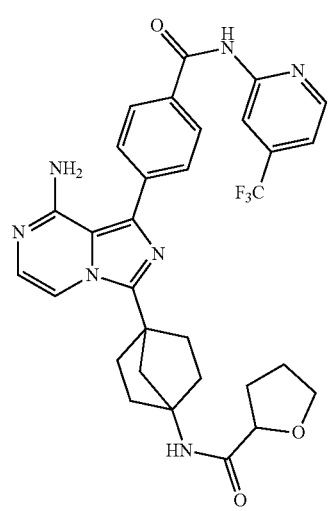
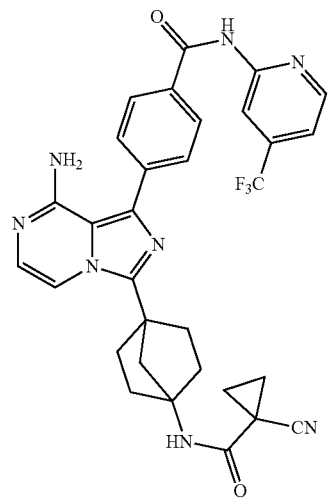
-continued
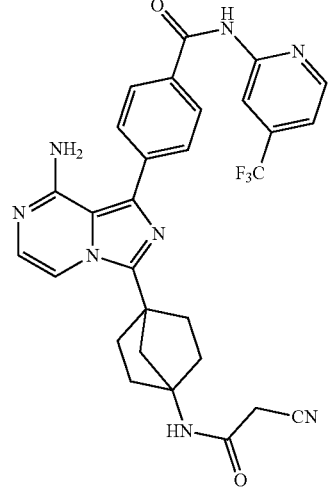
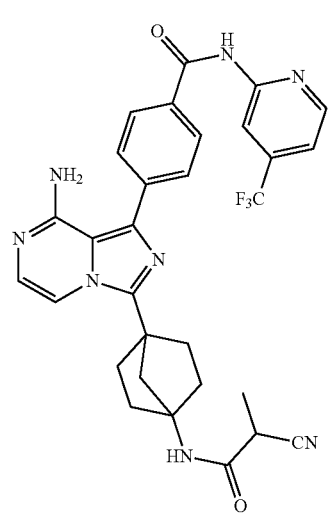
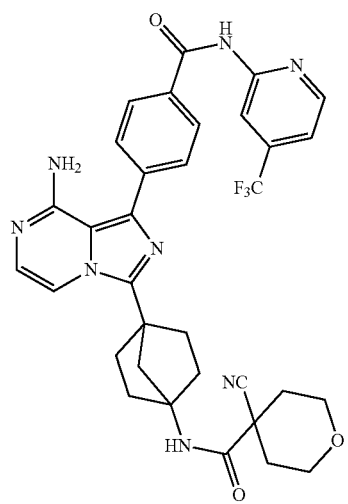

-continued
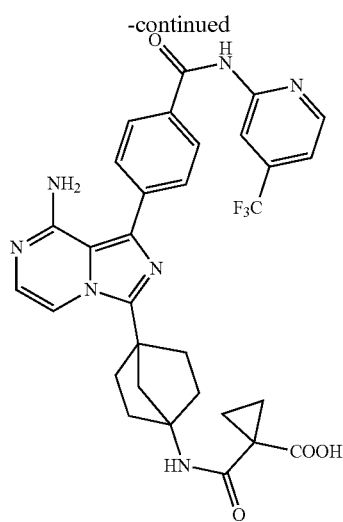
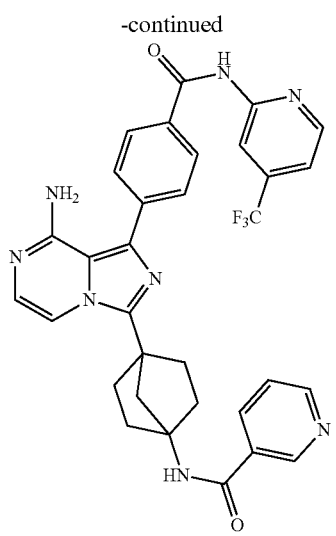
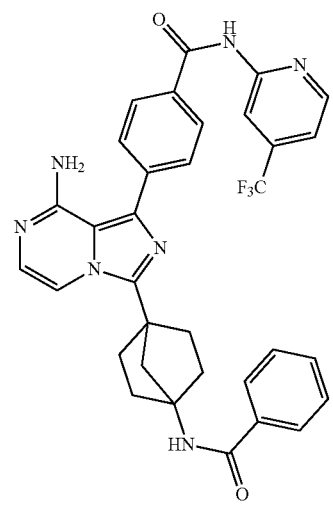
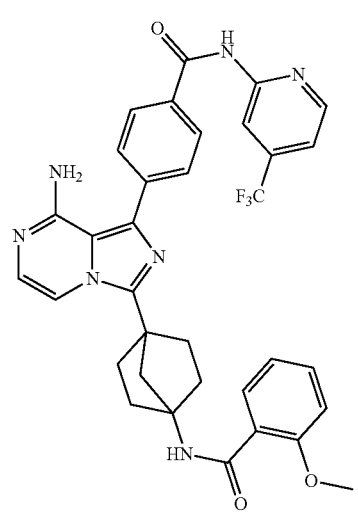
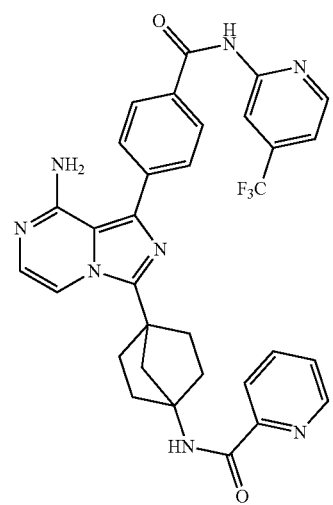
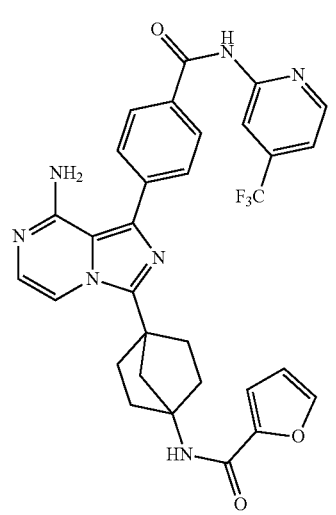

-continued
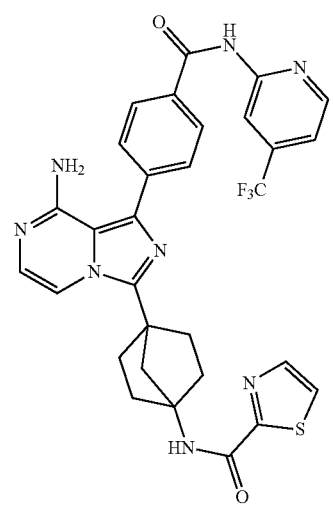
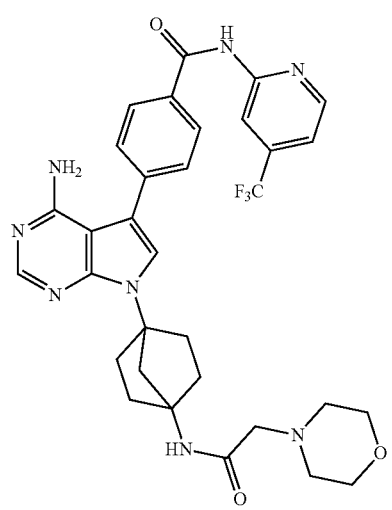
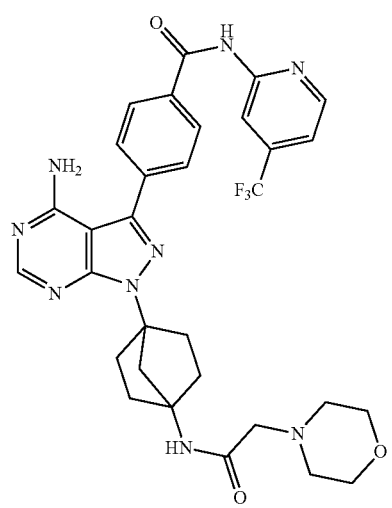
-continued
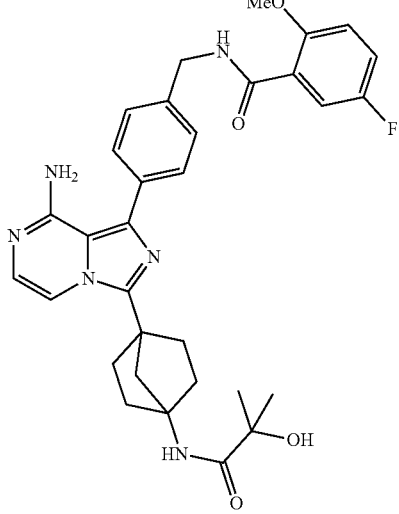
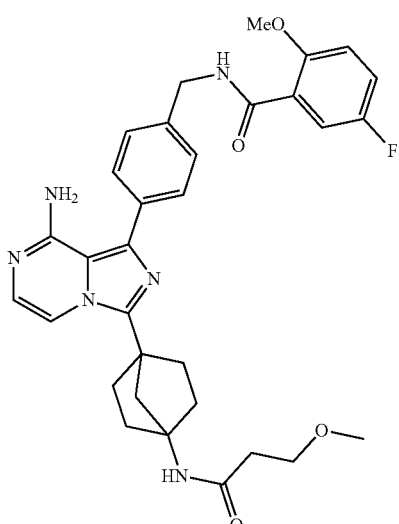
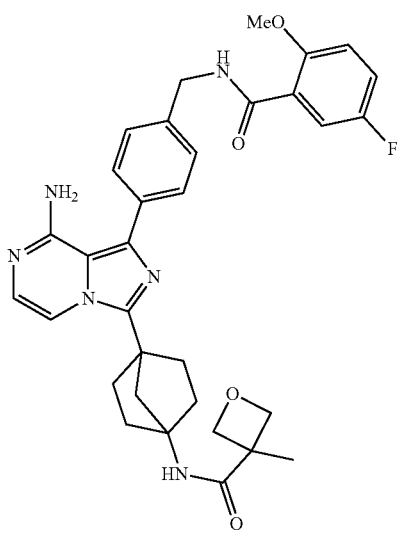

-continued
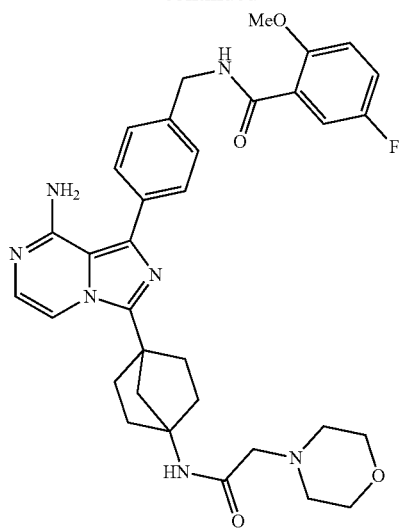
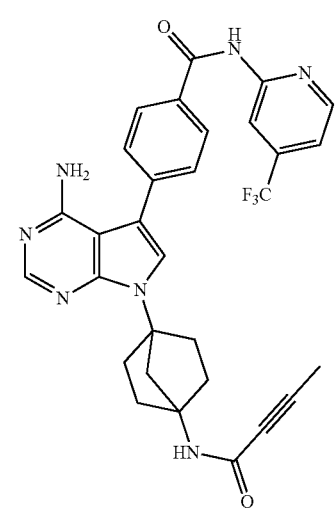
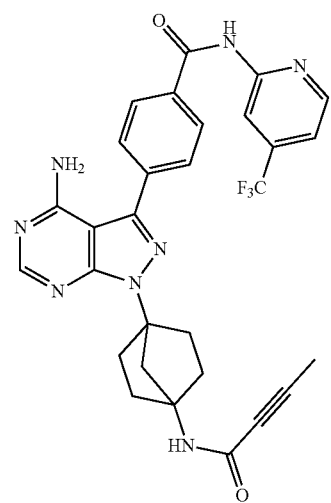
-continued
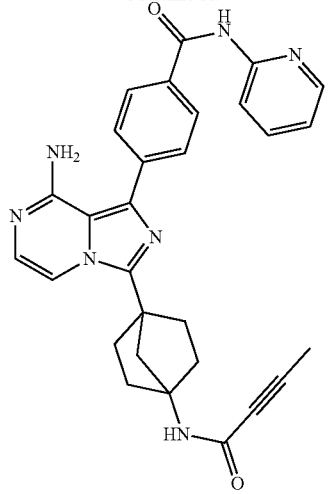
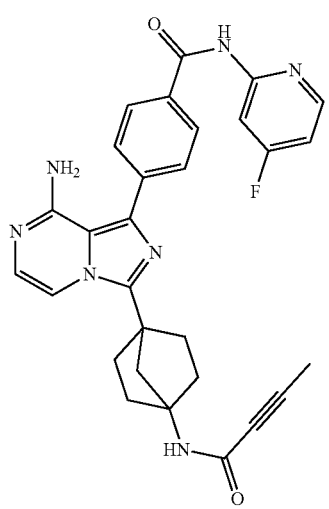
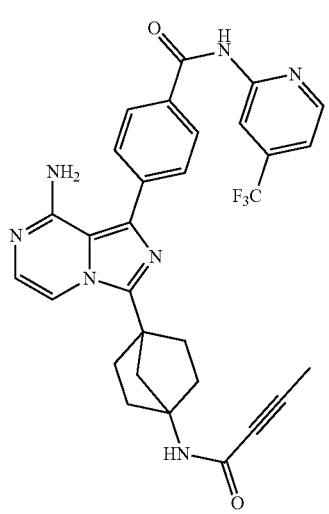

-continued
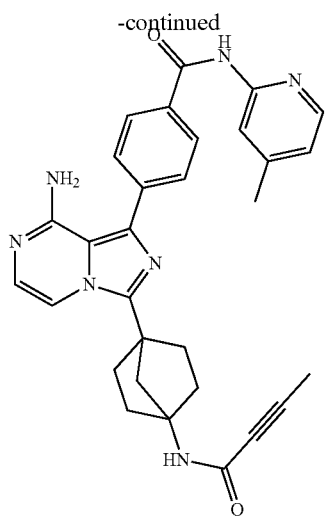 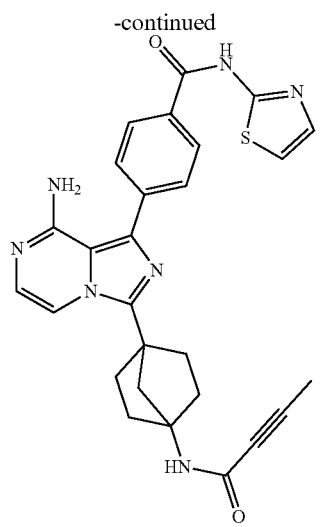
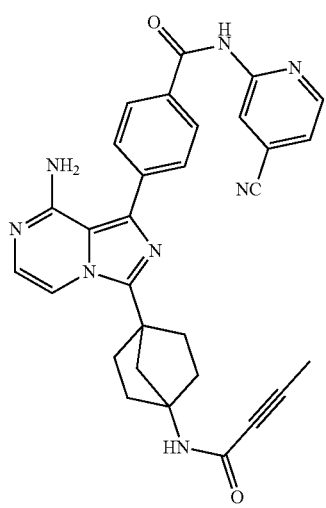 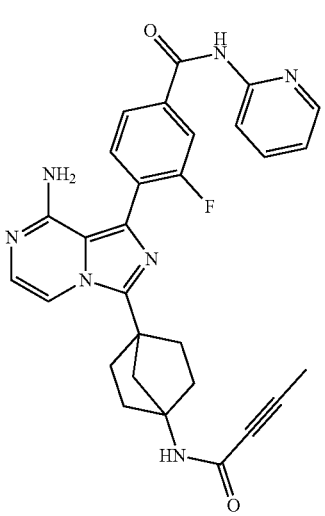
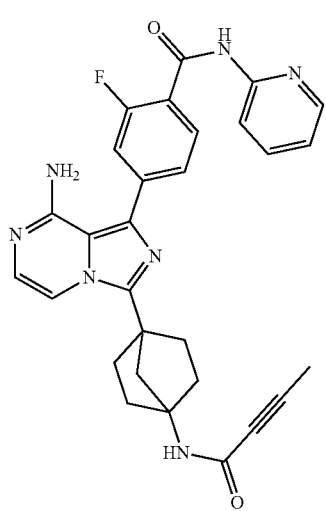 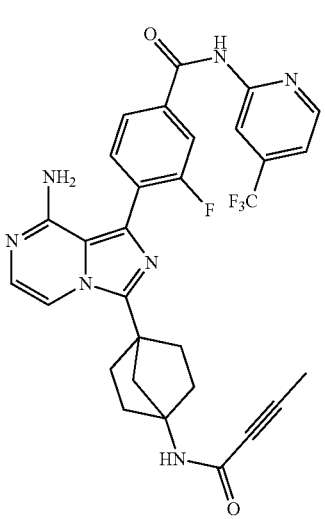

19
-continued
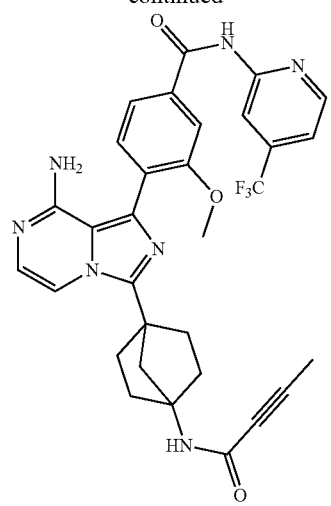
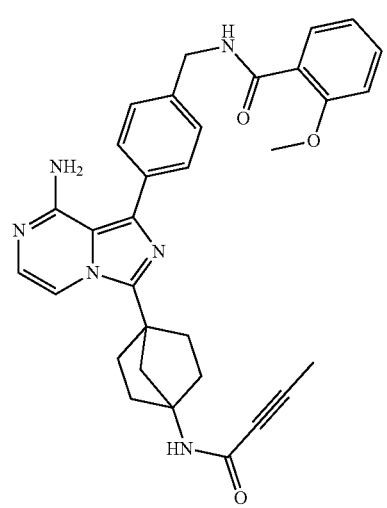
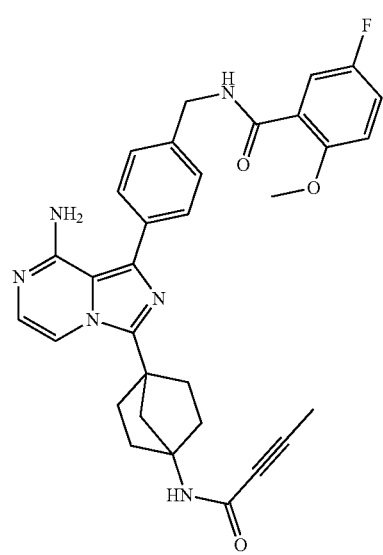
20
-continued
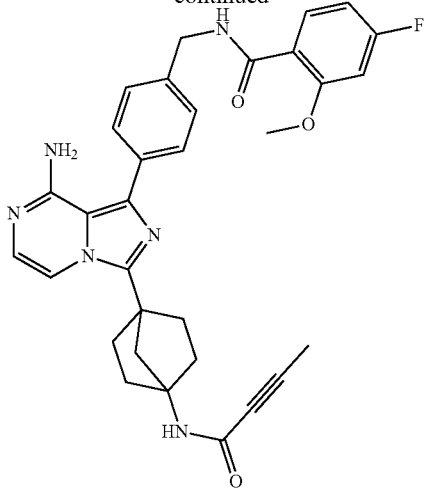
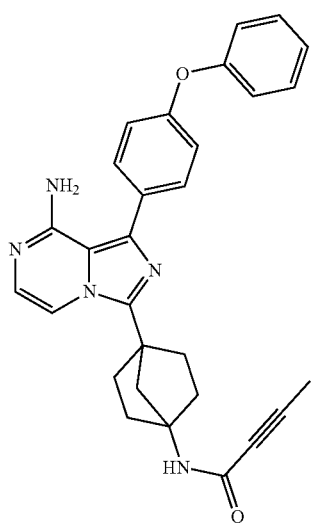
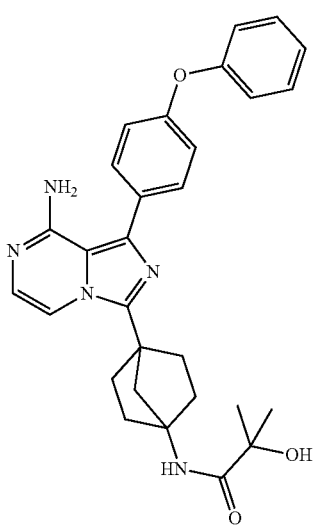

-continued
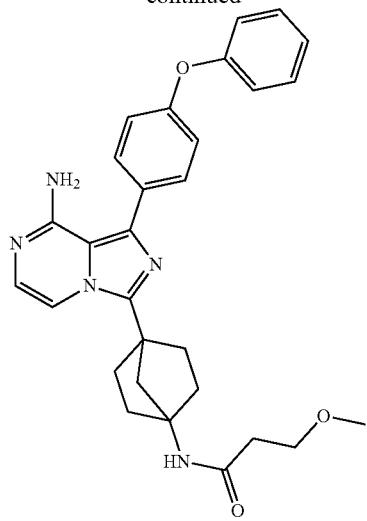
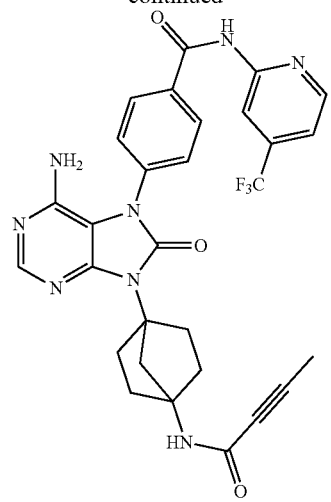
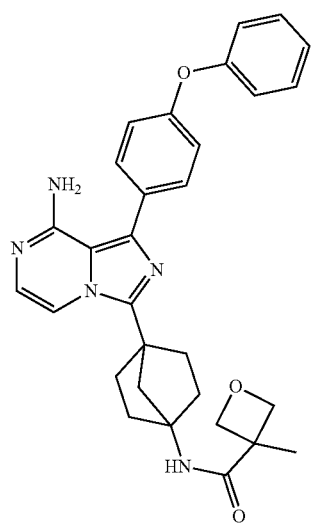
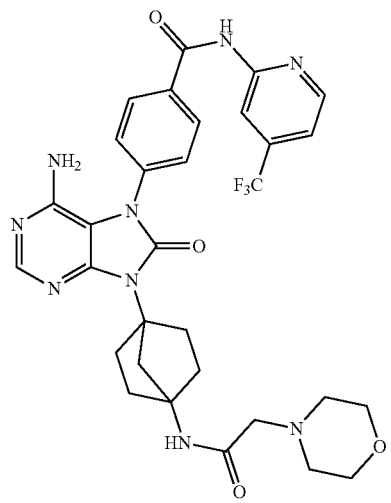
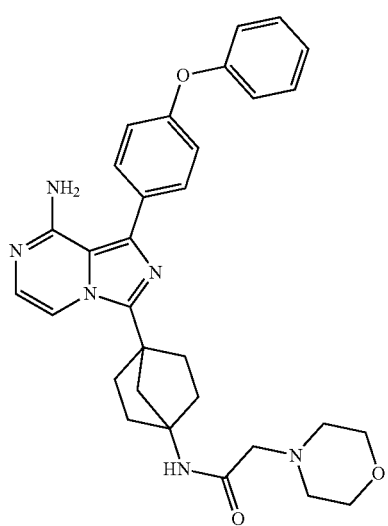
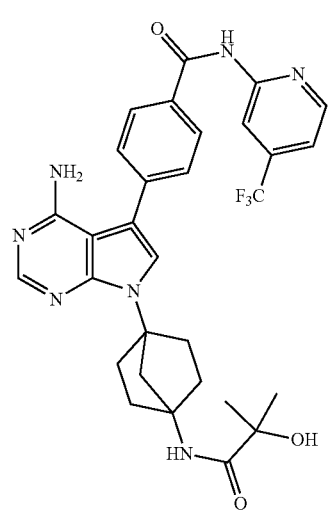

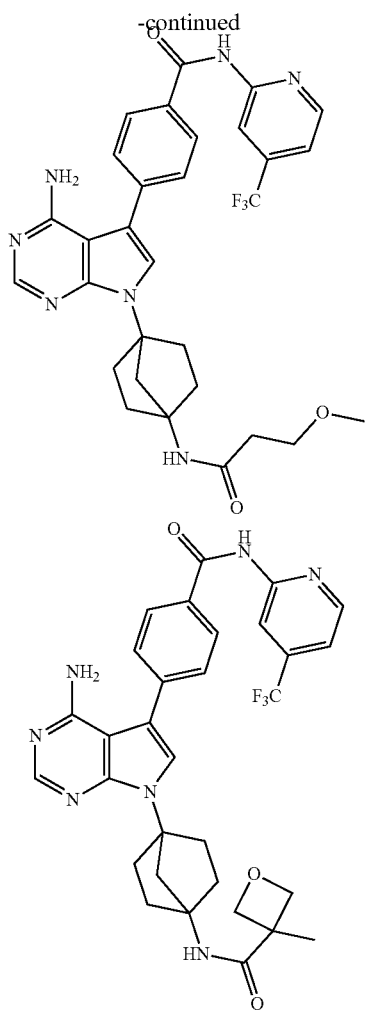

Provided is use of the compound according to any one of aspects above in the manufacture of a medicament for preventing or treating a heteroimmune disease, an autoimmune disease or a cancer,
wherein the heteroimmune disease, the autoimmune disease or the cancer is associated with excessive activity of Bruton's tyrosine kinase, or
the heteroimmune disease, the autoimmune disease or the cancer is associated with aberrant B-cell proliferation.

Further, the heteroimmune disease is an inflammatory disease or asthma.

Further, the autoimmune disease is lupus erythematosus, chronic lymphocytic lymphoma, diffuse large cell lymphoma, follicular lymphoma or chronic lymphocytic leukemia.

Provided is a pharmaceutical composition comprising one or more compounds according to any one of aspects above.

Provided is a pharmaceutical formulation comprising a therapeutically effective amount of the compound according to any one of aspects above and a pharmaceutically acceptable excipient.

The pharmaceutical formulation is formulated for oral administration, parenteral administration, buccal administration, nasal administration, topical administration or rectal administration.

The pharmaceutical formulation is for use in treating a disease or condition associated with excessive activity of Bruton's tyrosine kinase, comprising administering the pharmaceutical formulation to a human or mammal in need thereof; the disease associated with excessive activity of Bruton's tyrosine kinase is a heteroimmune disease, an autoimmune disease or a cancer; the heteroimmune disease is an inflammatory disease or asthma; the autoimmune disease is lupus erythematosus, chronic lymphocytic lymphoma, diffuse large cell lymphoma, follicular lymphoma or chronic lymphocytic leukemia.

The present invention comprises the step of contacting the pharmaceutical formulation with BTK, comprising an in vitro or in vivo assay.

Manufacture method 1 for the compound I above comprises: (S1) performing Suzuki coupling of compound IIIA with boronic acid or borate II to give compound IV; (S2) converting the compound IV into the hydrochloride of compound V by removal of benzyloxycarbonyl with trifluoroacetic acid; and (S3) coupling the compound V with an organic acid to give the compound I described above;

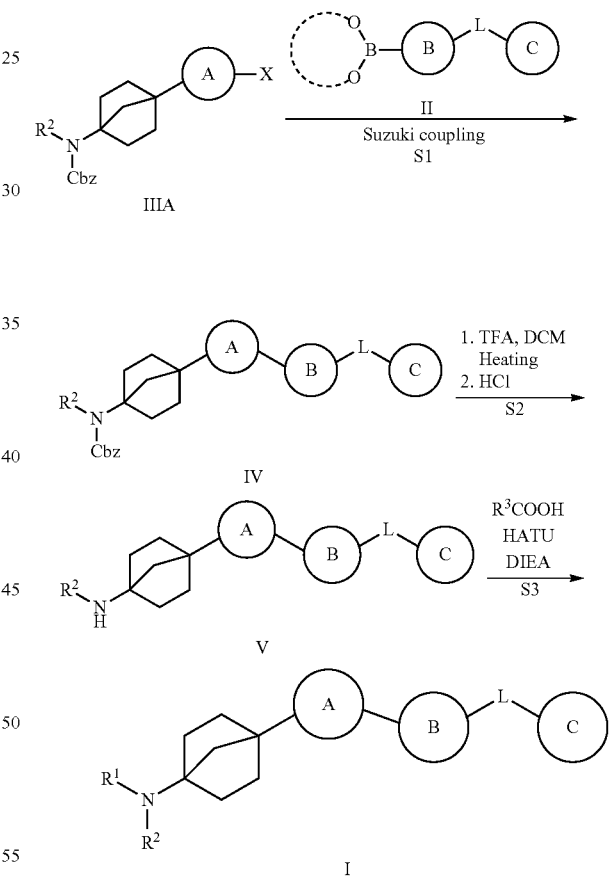

wherein X=halogen, and $R^2$, $R^3$, L, ring A, ring B and ring C are described as above.

Manufacture method 2 for the compound I above comprises: (A1) converting compound IIIA into the hydrochloride of compound VI by removal of benzyloxycarbonyl with trifluoroacetic acid; (A2) coupling the compound VI with an organic acid to give compound VII; and (A3) performing Suzuki coupling of the compound VII with boronic acid or borate II to give the compound I described above;

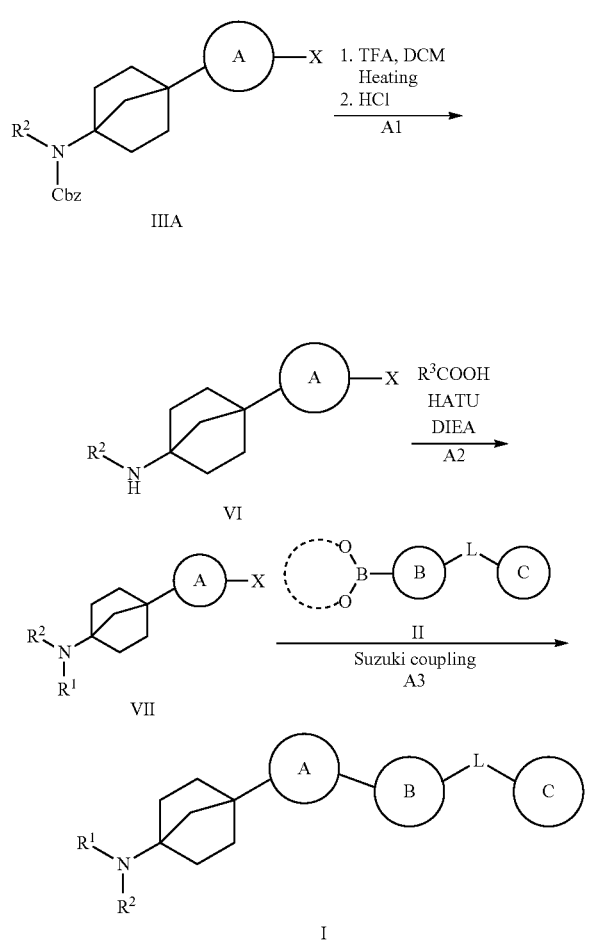

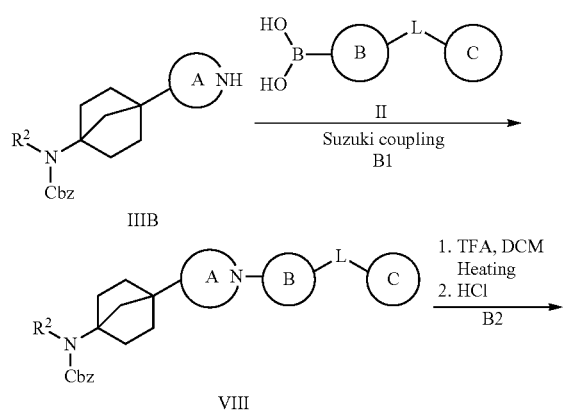

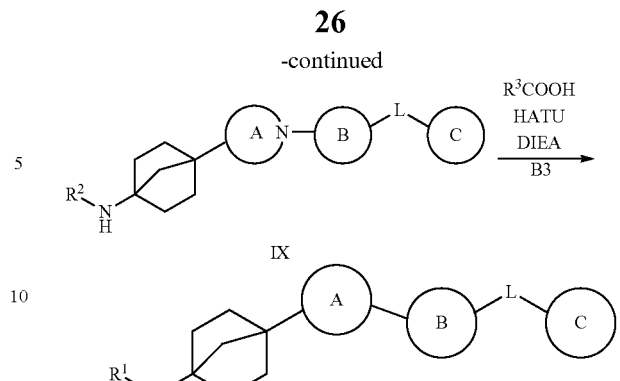

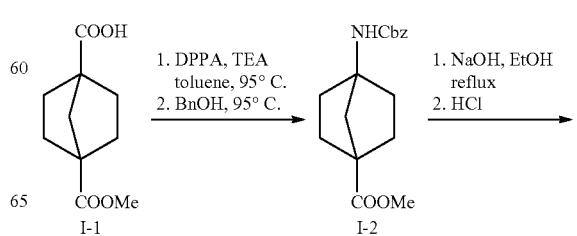

wherein X=halogen, and $R^2$, $R^3$, L, ring A, ring B and ring C are described as above.

Manufacture method 3 for the compound I above comprises: (B1) performing Chan-Lam-Evans coupling of compound IIIB with boronic acid II in the presence of catalyzation of copper acetate to give compound VIII; (B2) converting the compound VIII into the hydrochloride of compound IX by removal of benzyloxycarbonyl with trifluoroacetic acid; and (B3) coupling the compound IX with an organic acid to give the compound I described above;

wherein $R^2$, $R^3$, L, ring A, ring B and ring C are described as above.

Each of the products resulting from the reactions in methods 1, 2 and 3 may be obtained by conventional separation techniques, including but not limited to filtration, distillation, crystallization, chromatographic separation, and the like. The starting materials required for synthesis may be synthesized by: oneself or purchased from commercial establishments, such as Adrich or Sigma. These materials can be characterized using conventional means, such as physical constants and spectral data. The compounds described herein may be synthesized to give a single optical isomer or a mixture of optical isomers.

The superscripts of letters in the present invention indicate the sequence number of the group, and the subscripts indicate the number of the atom. For example: $R^1$, $R^2$ and $R^3$ represent the $1^{st}$ to the $3^{rd}$ R groups, and $C_{1-4}$ alkyl represents alkyl containing 1-4 C atoms. The number of C atoms on the substituent is not counted in the main chain.

DETAILED DESCRIPTION

Figure 1:
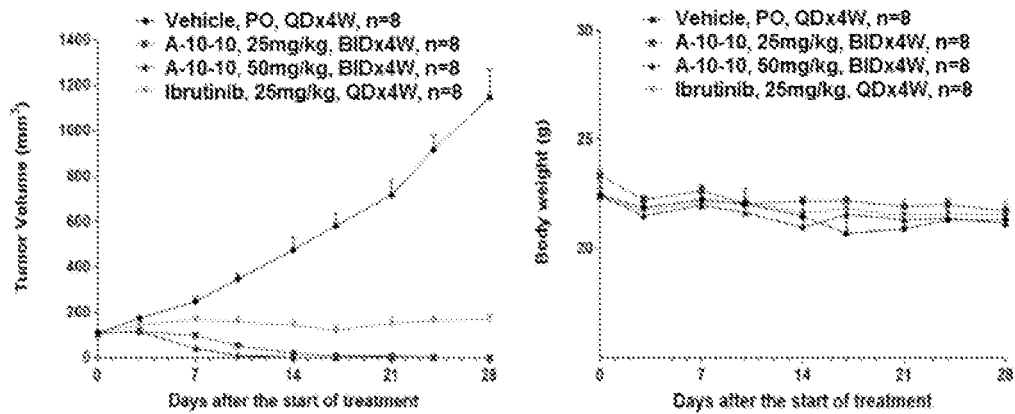
FIG. 1 is an OCI-LY10 xenograft tumor model.

The present invention can be better understood according to the following examples. However, it is easily understood by those skilled in the art that the content described in the examples are only used to illustrate the present invention, and should not and will not limit the present invention described in detail in the claims.

Synthesis of Intermediate I-5
Synthetic Route of Intermediate I-5

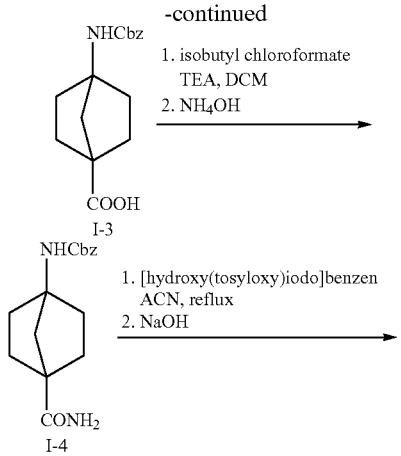

I-2: methyl 4-(((benzyloxy)carbonyl)amino)bicyclo[2.2.1]heptane-1-carboxylate

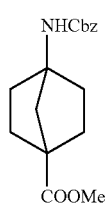

To a solution of 4-(methoxycarbonyl)bicyclo[2.2.1]heptane-1-carboxylic acid (I-1) (3.5 g, 17.7 mmol) and TEA (1.78 g, 17.7 mmol) in toluene (30 mL) was added DPPA (5.34 g, 19.5 mmol). The mixture was heated to 90° C. and maintained at this temperature for 2 h. After being cooled to room temperature, the mixture was added with BnOH (1.9 g, 17.7 mmol). The resulting mixture was stirred at 90° C. for 4 days. After being cooled to room temperature, the mixture was diluted with ethyl acetate and washed with aqueous NaHCO$_3$ solution. The organic phase was separated, dried over Na$_2$SO$_4$, filtered and evaporated. The residue was purified by column chromatography (ethyl acetate/petroleum ether=1:4) to give the desired compound I-2 (3 g, yield: 56%).

I-3: 4-(((benzyloxy)carbonyl)amino)bicyclo[2.2.1]heptane-1-carboxylic acid

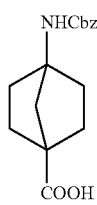

To a solution of methyl 4-(((benzyloxy)carbonyl)amino)bicyclo[2.2.1]heptane-1-carboxylate (I-2) (3 g, 9.9 mmol) was added NaOH (792 mg, 19.8 mmol), and the mixture was heated to 60° C. and maintained at this temperature for 10 h. The mixture was concentrated, added with water (50 mL), and then added with 1 N aqueous HCl solution to adjust the pH to 4. Ethyl acetate (20 mL×3) was added for extraction, and the organic phase was separated, dried over Na$_2$SO$_4$, filtered and evaporated to give the desired compound I-3 (2.2 g. yield: 77%), which was directly used in the next step without purification.

I-4: benzyl (4-carbamoylbicyclo[2.2.1]heptan-1-yl)carbamate

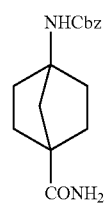

To a solution of compound I-3 (2 g, 6.9 mmol) and Et$_3$N (0 g, 10 mmol) in DCM (20 mL) was added isobutyl chloroformate (1.36 g, 10 mmol) dropwise at 0° C. The mixture was stirred at 0° C. for 20 min, added with NH$_4$OH (10 mL) dropwise and then stirred at room temperature for 10 min. The resulting mixture was poured into water (30 mL), and the organic phase was separated. The aqueous solution was extracted with DCM (15 mL×2), and the combined organic phases were dried over Na$_2$SO$_4$, filtered and concentrated. The residue was purified by column chromatography (eluent: EA/PE (1:1)-EA/MeOH (10:1)), to give the desired compound I-4 (1.7 g, yield: 85%).

I-5: benzyl (4-aminobicyclo[2.2.1]heptan-1-yl)carbamate

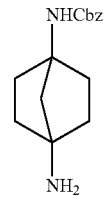

A solution of compound I-4 (1.6 g, 5.55 mmol) and [hydroxy(tosyloxy)iodo]benzene (2.17 g, 5.55 mmol) in ACN (20 mL) was heated to reflux for 1 h. The solvent was evaporated and 1 M NaOH (12 mL) was added. EA (15 mL×2) was added for extraction, and the organic phase was dried over Na$_2$SO$_4$, filtered and concentrated. The residue was purified by column chromatography (eluent: DCM/MeOH=10:1) to give the desired compound I-6 (920 mg, yield: 64%). LC-MS m/z=261.1[M+1]$^+$.

Synthesis of Intermediate Boronic Acid II

Synthetic Route of Intermediate II-1

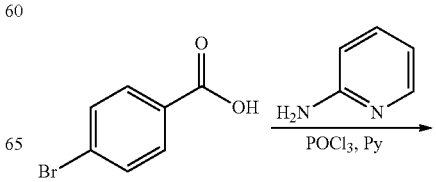

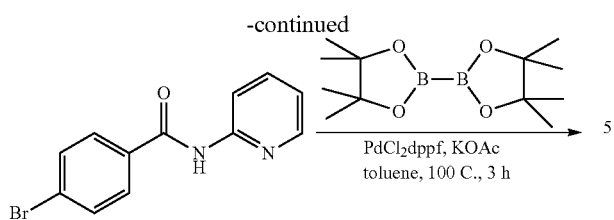

N-(pyridin-2-yl)-4-(4,4,5,5-tetramethyl-1,3,2-dioxaborolan-2-yl)benzamide

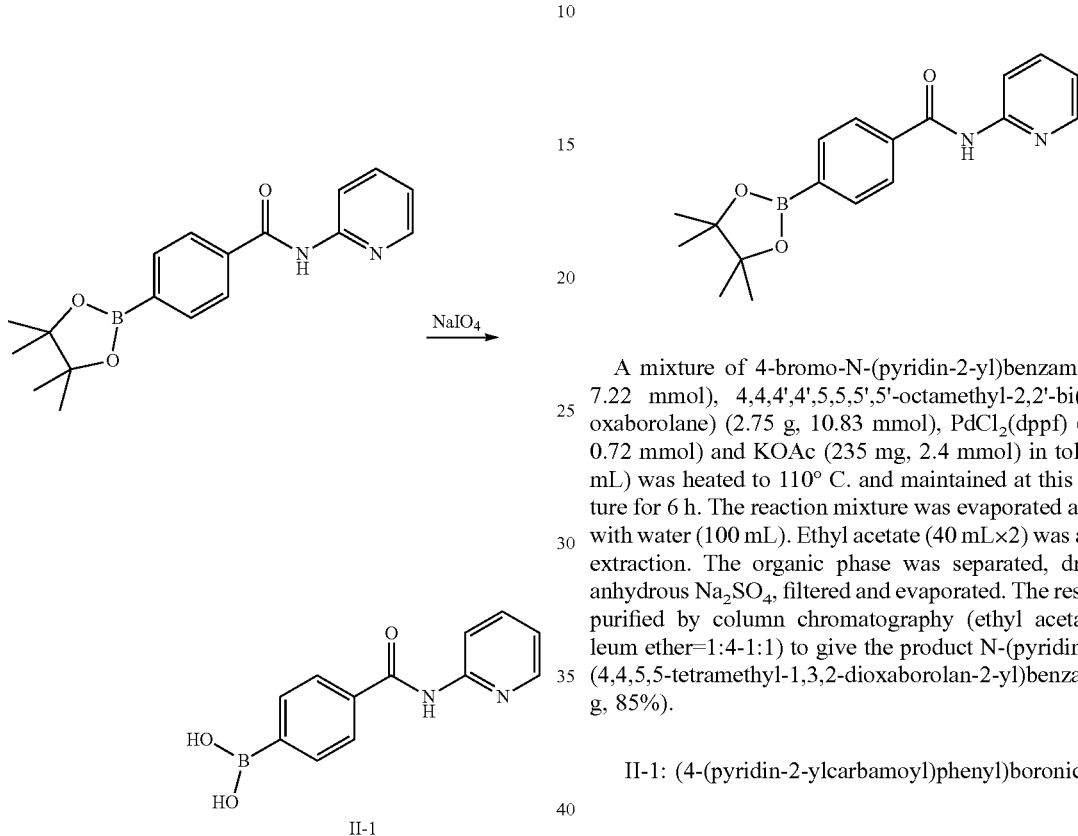

A mixture of 4-bromo-N-(pyridin-2-yl)benzamide (2 g, 7.22 mmol), 4,4,4',4',5,5,5',5'-octamethyl-2,2'-bi(1,3,2-dioxaborolane) (2.75 g, 10.83 mmol), PdCl$_2$(dppf) (527 mg, 0.72 mmol) and KOAc (235 mg, 2.4 mmol) in toluene (30 mL) was heated to 110° C. and maintained at this temperature for 6 h. The reaction mixture was evaporated and added with water (100 mL). Ethyl acetate (40 mL×2) was added for extraction. The organic phase was separated, dried over anhydrous Na$_2$SO$_4$, filtered and evaporated. The residue was purified by column chromatography (ethyl acetate/petroleum ether=1:4-1:1) to give the product N-(pyridin-2-yl)-4-(4,4,5,5-tetramethyl-1,3,2-dioxaborolan-2-yl)benzamide (2 g, 85%).

II-1: (4-(pyridin-2-ylcarbamoyl)phenyl)boronic acid

4-bromo-N-(pyridin-2-yl)benzamide

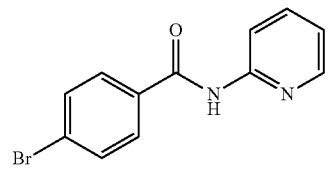 [SMILES: O=C(Nc1ccccn1)c1ccc(Br)cc1]

To a mixture of 4-bromobenzoic acid (5 g, 24.8 mmol) and pyridin-2-amine (4.68 g, 49 mmol) in pyridine (30 mL) was added POCl$_3$ (11.4 g, 74 mmol) dropwise under an ice bath. The suspension was stirred at room temperature for 20 min. The reaction mixture was poured into water (100 mL) and extracted with ethyl acetate (40 mL×3). The organic phase was washed with saturated aqueous NaCl solution (50 mL×2), dried over anhydrous Na$_2$SO$_4$, filtered and evaporated. The residue was purified by column chromatography (ethyl acetate/petroleum ether=1:9-1:1) to give the product 4-bromo-N-pyridin-2-yl)benzamide (3.28 g, 48%). LC-MS m/z=277.0[M+1]$^+$.

To a solution of N-(pyridin-2-yl)-4-(4,4,5,5-tetramethyl-1,3,2-dioxaborolan-2-yl) benzamide (2 g, 6.2 mmol) in a mixed solvent of THF:H$_2$O (24 mL:6 mL) was added NaIO$_4$ (3.27 g, 18.6 mmol), and the mixture was stirred at room temperature for 30 min. 2 N aqueous HCl solution (1.65 mL) was then added, and the resulting mixture was stirred at room temperature for 3 h. The mixture was diluted with ethyl acetate and washed with brine. The organic phase was separated, dried over anhydrous Na$_2$SO$_4$, filtered and concentrated. The residue was purified by column chromatography (MeOH/DCM=1:10) to give the product (4-(pyridin-2-ylcarbamoyl)phenyl)boronic acid (II-1) (1.4 g, 93%). LC-MS m/z=243.1[M+1]$^+$.

Synthetic Route of Intermediate II-2

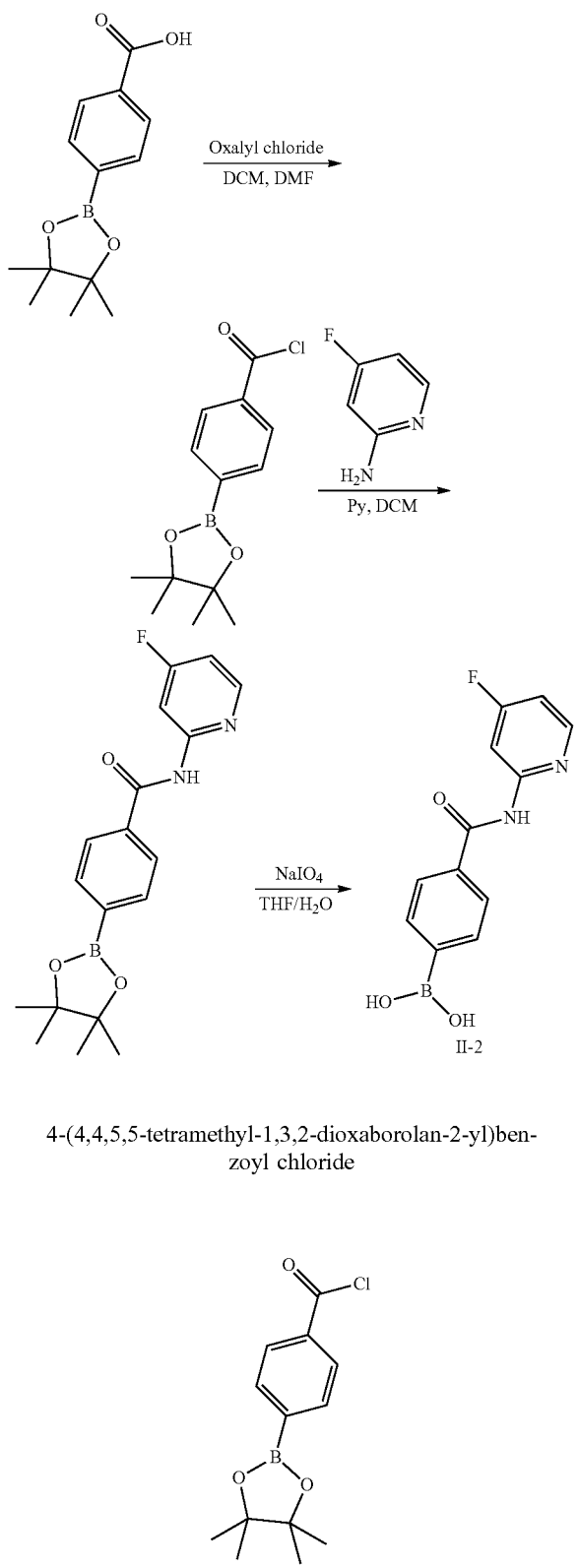

4-(4,4,5,5-tetramethyl-1,3,2-dioxaborolan-2-yl)benzoyl chloride

To a solution of 4-(4,4,5,5-tetramethyl-1,3,2-dioxaborolan-2-yl)benzoic acid (10 g, 40 mmol) and 1 drop of DMF in DCM (100 mL) was added oxalyl chloride (10.2 g, 80 mmol) dropwise under an ice bath. The mixture was stirred at 0° C. for 30 min, and then warmed to room temperature and maintained at this temperature for 3 h. The mixture was then concentrated to give a product, which was directly used in the next step without purification.

N-(4-fluoropyridin-2-yl)-4-(4,4,5,5-tetramethyl-1,3,2-dioxaborolan-2-yl)benzamide To a solution of 4-fluoropyridin-2-amine (421 mg, 3.76 mmol) in pyridine (3 mL) was added a solution of 4-(4,4,5,5-tetramethyl-1,3,2-dioxaborolan-2-yl)pyridin-2-yl)benzoyl chloride (1 g, 3.76 mmol) in DCM (6 mL), and the suspension was stirred at 0° C. for 30 min. The mixture was poured into water and extracted with DCM (20 mL×2). The organic phase was washed with saturated aqueous NaCl solution, separated, dried over anhydrous $Na_2SO_4$ and evaporated, and the residue was purified by column chromatography (ethyl acetate/petroleum ether=1:9) to give the product (1.04 g, 81%). LC-MS m/z=343.2 $[M+1]^+$.

II-2: (4-((4-fluoropyridin-2-yl)carbamoyl)phenyl)boronic acid

To a solution of N-(4-fluoropyridin-2-yl)-4-(4,4,5,5-tetramethyl-1,3,2-dioxaborolan-2-yl) benzamide (1.04 g, 3.04 mmol) in a mixed solvent of $THF:H_2O$ (24 mL:6 mL) was added $NaIO_4$ (1.9 g, 9.12 mmol), and the mixture, was stirred at room temperature for 30 min. Aqueous HCl solution (1.65 mL) was then added, and the resulting mixture was stirred at room temperature for 3 h. The mixture was diluted with ethyl acetate and washed with brine. The organic phase was separated, dried over anhydrous Na$_2$SO$_4$, filtered and concentrated. The residue was purified by column chromatography (MeOH/DCM=1:10) to give the product II-2 (648 mg, 82%). LC-MS m/z=261.1 [M+1]$^+$.

II-3: (4-((4-(trifluoromethyl)pyridin-2-yl)carbamoyl)phenyl)boronic acid

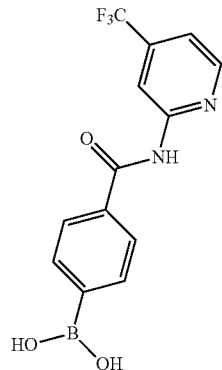 [SMILES: O=C(Nc1cc(C(F)(F)F)ccn1)c1ccc(B(O)O)cc1]

With 4-(trifluoromethyl)pyridin-2-amine (609 mg, 3.76 mmol) and 4-(4,4,5,5-tetramethyl-1,3,2-dioxaborolan-2-yl)pyridin-2-yl)benzoyl chloride (1 g, 3.76 mmol) as the starting materials, the same synthetic method as that of II-2 was used to give the desired compound (607 mg). LC-MS m/z=311.1 [M+1]$^+$.

II-4: (4-((4-methylpyridin-2-yl)carbamoyl)phenyl)boronic acid

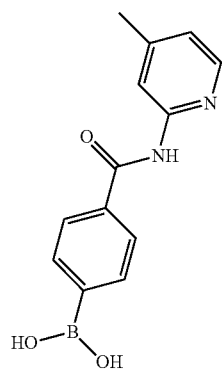 [SMILES: Cc1ccnc(NC(=O)c2ccc(B(O)O)cc2)c1]

With 4-methyl-pyridin-2-amine (406 mg, 3.76 mmol) and 4-(4,4,5,5-tetramethyl-1,3,2-dioxaborolan-2-yl)pyridin-2-yl)benzoyl chloride (1 g, 3.76 mmol) as the starting materials, the same synthetic method as that of II-2 was used to give the desired compound (589 mg). LC-MS m/z=257.1 [M+1]$^+$.

II-5: (4-((4-cyanopyridin-2-yl)carbamoyl)phenyl)boronic acid

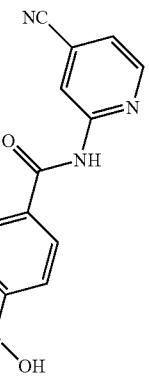

With 4-cyano-pyridin-2-amine (447 mg, 3.76 mmol) and 4-(4,4,5,5-tetramethyl-1,3,2-dioxaborolan-2-yl)pyridin-2-yl)benzoyl chloride (1 g, 3.76 mmol) as the starting materials, the same synthetic method as that of II-2 was used to give the desired compound (465 mg). LC-MS m/z=268.0 [M+1]$^+$.

Synthetic Route of Intermediate II-6

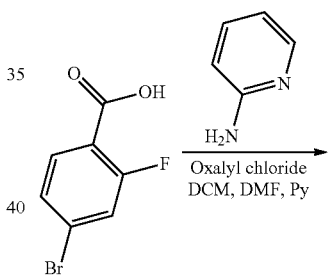

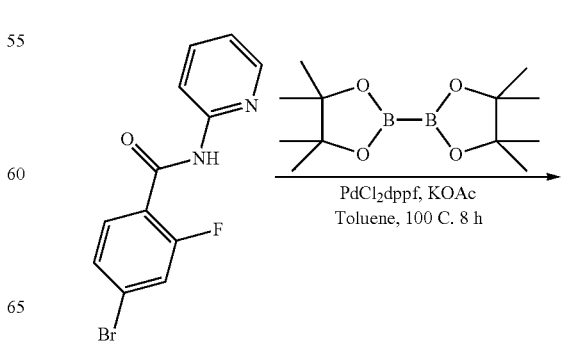

-continued

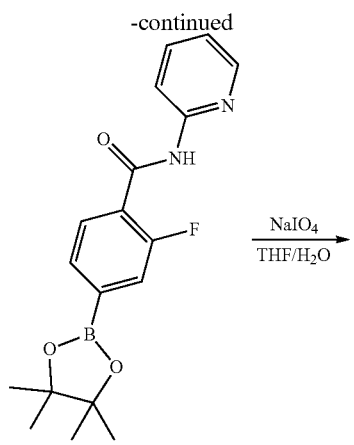

$\xrightarrow{\text{NaIO}_4}$
THF/H$_2$O

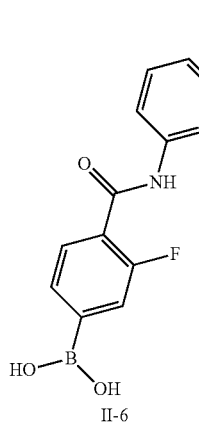

II-6

4-bromo-2-fluoro-N-(pyridin-2-yl)benzamide

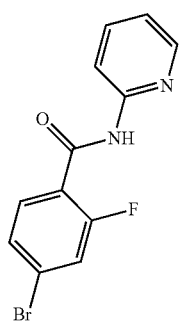 [SMILES: O=C(Nc1ccccn1)c1ccc(Br)cc1F]

To a solution of 4-bromo-2-fluorobenzoic acid (1 g, 4.56 mmol) in DCM (30 mL) was added oxalyl chloride (1.16 g, 9.13 mmol) dropwise under an ice bath, and then 1 drop of DMF was added. After being stirred at room temperature for 3 h, the mixture was concentrated and dissolved in DCM (6 mL). The resulting solution was added to a solution of pyridin-2-amine (428 mg, 4.56 mmol) in pyridine (3 mL) at 0° C., and the suspension was stirred at 0° C. for 30 min. The mixture was poured into water and extracted with DCM (20 mL×2). The organic phase was washed with saturated aqueous NaCl solution, separated, dried over anhydrous Na$_2$SO$_4$ and evaporated, and the residue was purified by column chromatography (ethyl acetate/petroleum ether=1:9) to give the product (1.05 g, 78%). LC-MS m/z=295.01 [M+1]$^+$.

2-fluoro-N-(pyridin-2-yl)-4-(4,4,5,5-tetramethyl-1,3,2-dioxaborolan-2-yl)benzamide

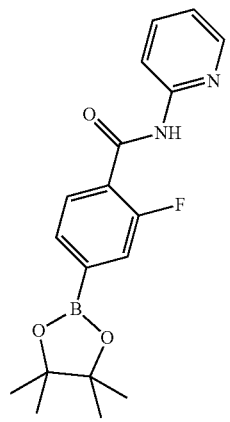 [SMILES: CC1(C)OB(c2ccc(C(=O)Nc3ccccn3)c(F)c2)OC1(C)C]

A solution of 4-bromo-2-fluoro-N-(pyridin-2-yl)benzamide (1.05 g, 3.55 mmol), (4,4,5,5-tetramethyl-1,3,2-dioxaborolan-2-yl)-1,3,2-dioxaborolane (1.36 g, 5.3 mmol), PdCl$_2$(dppf) (260 mg, 0.36 mmol) and KOAc (1.04 g, 10.65 mmol) in toluene (30 mL) was heated to 110° C. and maintained at this temperature for 6 h. The reaction mixture was evaporated and then added with water (100 mL). Ethyl acetate (40 mL×2) was added for extraction. The organic phase was separated, dried over anhydrous Na$_2$SO$_4$, filtered and evaporated. The residue was purified by column chromatography (ethyl acetate/petroleum ether=1:4-1:1) to give the product (971 mg, 80%).

II-6:
(3-fluoro-4-(pyridin-2-ylcarbamoyl)phenyl)boronic acid

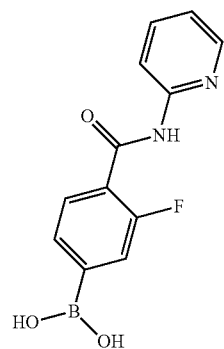 [SMILES: O=C(Nc1ccccn1)c1ccc(B(O)O)cc1F]

To a solution of 2-fluoro-N-(pyridin-2-yl)-4-(4,4,5,5-tetramethyl-1,3,2-dioxaborolan-2-yl)benzamide (970 mg, 2.84 mmol) in a mixed solvent of THF:H$_2$O (24 mL:6 mL) was added NaIO$_4$ (1.8 g, 8.52 mmol), and the mixture was stirred at room temperature for 30 min. Aqueous HCl solution (1.65 mL) was then added. After being stirred at room temperature for 3 h, the mixture was diluted with ethyl acetate and washed with brine. The organic phase was separated, dried over anhydrous Na$_2$SO$_4$, filtered and concentrated. The residue was purified by column chromatography (MeOH/DCM=1:10) to give the product II-6 (605 mg, 82%). LC-MS m/z=261.1 [M+1]$^+$.

II-7: (4-(thiazol-2-ylcarbamoyl)phenyl)boronic acid

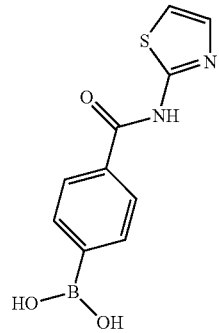 [SMILES: O=C(Nc1nccs1)c1ccc(B(O)O)cc1]

With thiazol-2-amine (376 mg, 3.76 mmol) and 4-(4,4,5,5-tetramethyl-1,3,2-dioxaborolan-2-yl)pyridin-2-yl)benzoyl chloride (1 g, 3.76 mmol) as the starting materials, the same synthetic method as that of II-2 was used to give the desired compound II-7 (580 mg). LC-MS m/z=249.1 [M+1]+.

II-8: (2-fluoro-4-(pyridin-2-ylcarbamoyl)phenyl)boronic acid

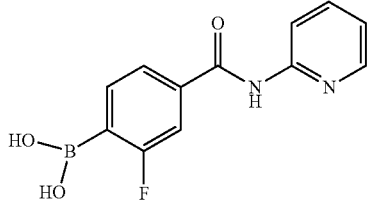 [SMILES: O=C(Nc1ccccn1)c1ccc(B(O)O)c(F)c1]

With 4-bromo-3-fluoro-benzoic acid and pyridin-2-amine as the starting materials, the same synthetic method as that of II-1 was used to give the desired compound II-8 (138 mg). LC-MS m/z=261.0 [M+1]+.

II-9: (2-fluoro-4-((4-(trifluoromethyl)pyridin-2-yl)carbamoyl)phenyl)boronic acid

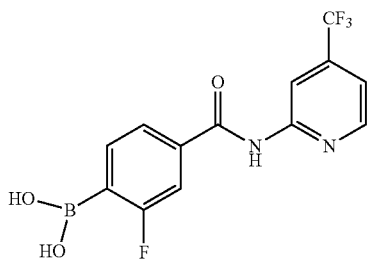 [SMILES: O=C(Nc1cc(C(F)(F)F)ccn1)c1ccc(B(O)O)c(F)c1]

With 4-bromo-3-fluoro-benzoic acid and 4-(trifluoromethyl)-pyridin-2-amine as the starting materials, the same synthetic method as that of II-1 was used to give the desired compound II-9 (130 mg). LC-MS m/z=329.0 [M+1]+.

II-10: (2-methoxy-4-((4-(trifluoromethyl)pyridin-2-yl)carbamoyl)phenyl)boronic acid

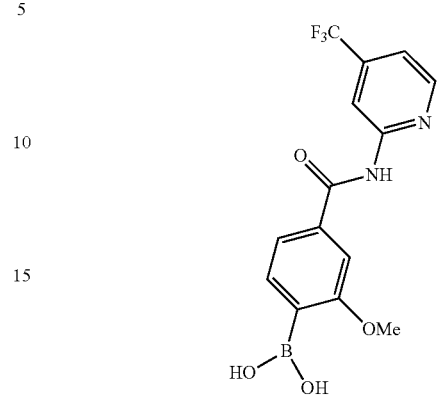

With 4-bromo-3-methoxybenzoic acid (1 g, 4.36 mmol) and 4-(trifluoromethyl)-pyridin-2-amine (706 mg, 4.36 mmol) as the starting materials, the same synthetic method as that of II-6 was used to give the desired compound II-10 (440 mg). LC-MS m/z=341.0 [M+1]+.

Synthetic Route of Intermediate Borate II-11

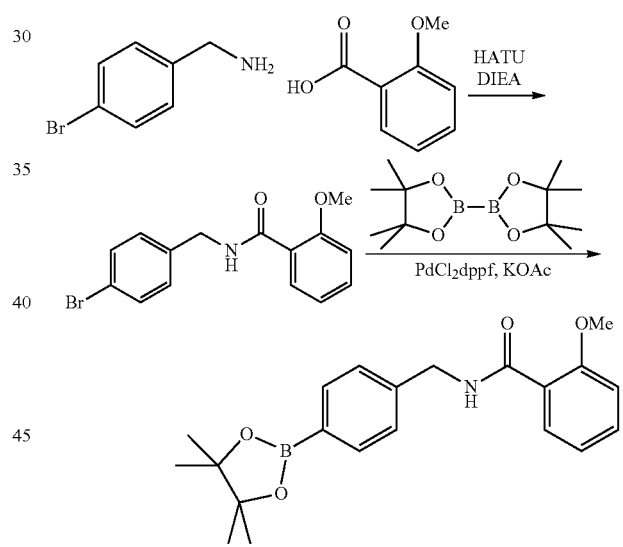

N-(4-bromobenzyl)-2-methoxybenzamide

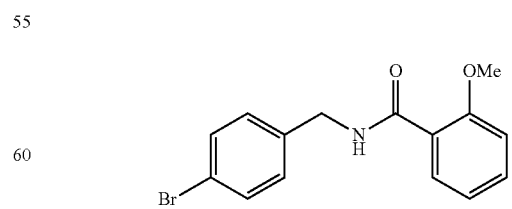

A solution of 4-bromobenzylamine (1 g, 5.38 mmol), 2-methoxybenzoic acid (818 mg, 5.38 mmol), HATU (2.45 g, 6.46 mmol) and DIEA (1.39 g, 10.76 mmol) in DMF (20 mL) was stirred at room temperature for 2 h. The mixture was poured into water (50 mL), filtered, washed with water (30 mL×2) and dried to give the desired compound (1.6 g, yield: 93%), which was directly used in the next step without purification.

II-11: 2-methoxy-N-(4-(4,4,5,5-tetramethyl-1,3,2-dioxaborolan-2-yl)benzyl)benzamide

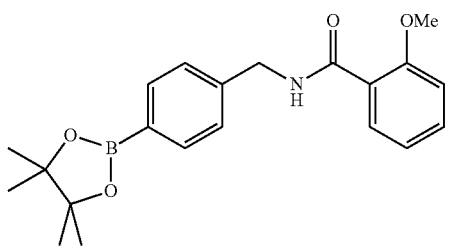 [SMILES: COc1ccccc1C(=O)NCc1ccc(B2OC(C)(C)C(C)(C)O2)cc1]

A solution of N-(4-bromobenzyl)-2-methoxy benzamide (1.6 g, 5 mmol), 4,4,4',4',5,5,5',5'-octamethyl-2,2'-bi(1,3,2-dioxaborolane) (1.9 g, 7.5 mmol), PdCl₂(dppf) (365 mg, 0.5 mmol) and KOAc (1.47 g, 15 mmol) in dioxane (30 mL) was heated to 100° C. and maintained at this temperature for 6 h. The mixture was concentrated, added with water (100 ml), and then extracted with ethyl acetate (20 mL×2). The organic phase was separated, dried over Na₂SO₄, filtered and concentrated, and the residue was purified by column chromatography (ethyl acetate/petroleum ether 1:9) to give the desired compound II-11 (1.5 g, yield: 82%).

II-12: 5-fluoro-2-methoxy-N-(4-(4,4,5,5-tetramethyl-1,3,2-dioxaborolan-2-yl)benzyl) benzamide

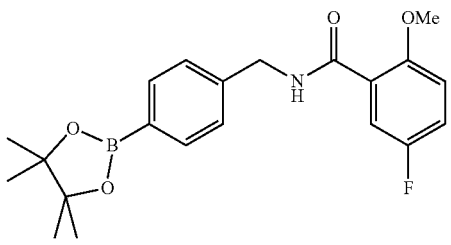 [SMILES: COc1ccc(F)cc1C(=O)NCc1ccc(B2OC(C)(C)C(C)(C)O2)cc1]

With 5-fluoro-2-methoxybenzoic acid (915 mg, 5.38 mmol) and 4-bromobenzylamine (1 g, 5.38 mmol) as the starting materials, the same synthetic method as that of II-11 was used to give the desired compound II-12 (900 mg).

II-13: 4-fluoro-2-methoxy-N-(4-(4,4,5,5-tetramethyl-1,3,2-dioxaborolan-2-yl)benzyl) benzamide

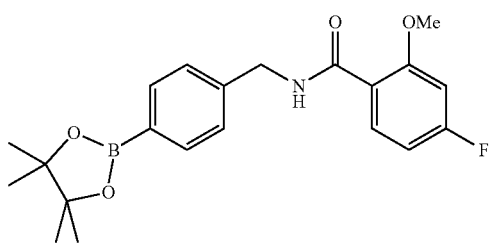 [SMILES: COc1cc(F)ccc1C(=O)NCc1ccc(B2OC(C)(C)C(C)(C)O2)cc1]

With 4-fluoro-2-methoxybenzoic acid (915 mg, 5.38 mmol) and 4-bromobenzylamine (1 g, 5.38 mmol) as the starting materials, the same synthetic method as that of II-11 was used to give the desired compound II-13 (1 g).

Synthetic Route of Intermediate A-4

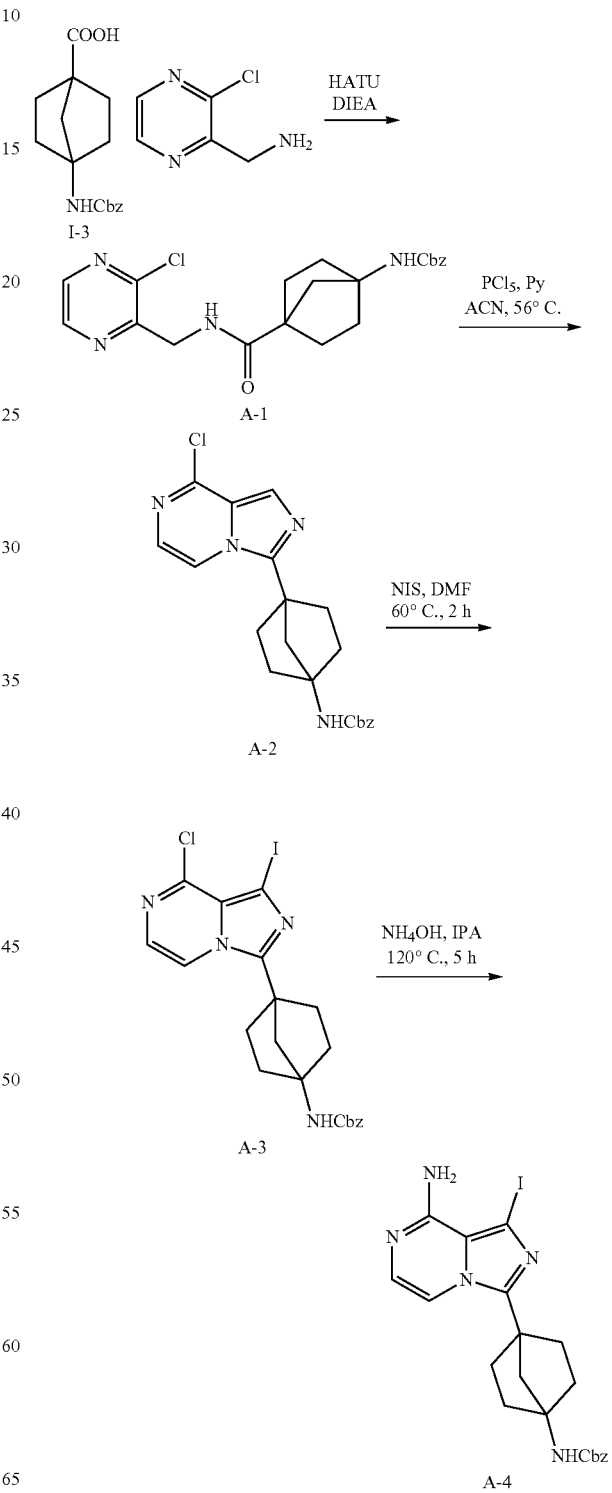

A-1: benzyl(4-(((3-chloropyrazin-2-yl)methyl)carbamoyl)bicyclo[2.2.1]heptan-1-yl)carbamate

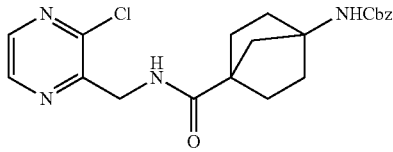 [SMILES: O=C(NC12CCC(C(=O)NCc3nccnc3Cl)(CC1)C2)OCc1ccccc1]

A solution of 4-(((benzyloxy)carbonyl)amino)bicyclo[2.2.1]heptane-1-carboxylic acid (2 g, 6.9 mmol), HATU (2.89 g, 7.6 mmol), DIEA (3.56 g, 27.6 mmol) and the hydrochloride of (3-chloropyrazin-2-yl)methylamine (1.3 g, 7.24 mmol) in DMF (20 mL) was stirred at room temperature for 6 h. The mixture was poured into water (100 mL) and extracted with ethyl acetate (30 mL×2). The organic phase was washed with saturated aqueous NaCl solution, separated, dried over Na$_2$SO$_4$, filtered and evaporated. The residue was purified by column chromatography (ethyl acetate/petroleum ether=1:1-1:0) to give the desired compound A-1 (2 g, yield: 70%). LC-MS m/z=414.9 [M+1]$^+$.

A-2: benzyl (4-(8-chloroimidazo[1,5-a]pyrazin-3-yl)bicyclo[2.2.1]heptan-1-yl)carbamate

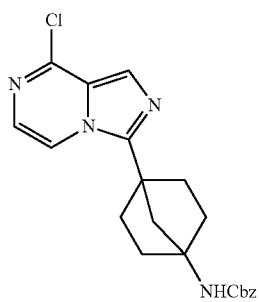 [SMILES: O=C(NC12CCC(c3ncc4c(Cl)nccn34)(CC1)C2)OCc1ccccc1]

To a solution of benzyl (4N-(((3-chloropyrazin-2-yl)methyl)carbamoyl)bicyclo[2.2.1]heptan-1-yl)carbamate (A-1) (2 g, 4.83 mmol) in ACN (30 mL) were added pyridine (381 mg, 4.83 mmol) and PCl$_5$ (4 g, 19.32 mmol), and the mixture was heated to 56° C. and maintained at this temperature for 1 h. After being cooled to room temperature, the mixture was slowly poured into ice saturated aqueous NaHCO$_3$ solution (100 mL). While maintaining pH at 9, the mixture was extracted with ethyl acetate (30 mL×2). The organic phase was washed with saturated aqueous NaCl solution, separated, dried over Na$_2$SO$_4$, filtered and evaporated. The residue was purified by column chromatography (ethyl acetate/petroleum ether=1:1) to give the desired compound A-2 (1.5 g, yield: 78%).

A-3: benzyl (4-(8-chloro-1-iodoimidazo[1,5-a]pyrazin-3-yl)bicyclo[2.2.1]heptan-1-yl)carbamate

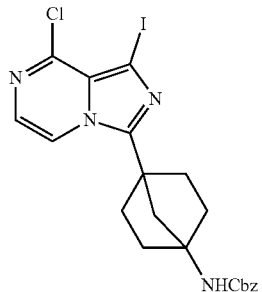 [SMILES: O=C(NC12CCC(c3nc(I)c4c(Cl)nccn34)(CC1)C2)OCc1ccccc1]

A mixed solution of benzyl (4-(8-chloroimidazo[1,5-a]pyrazin-3-yl)bicyclo[2.2.1]heptan-1-yl)carbamate (A-2) (1.5 g, 3.79 mmol) and NIS (1.13 g, 5.04 mmol) in DMF (10 mL) was heated to 60° C. under N$_2$ atmosphere and stirred for 10 h. After being cooled to room temperature, the mixture was poured into water (100 mL) and extracted with ethyl acetate (30 mL×2). The organic phase was washed with saturated aqueous NaCl solution, separated, dried over Na$_2$SO$_4$, filtered and evaporated. The residue was purified by column chromatography (ethyl acetate/petroleum ether=2:3) to give the desired compound A-3 (1.52 g, yield: 77%).

A-4: benzyl (4-(8-amino-1-iodoimidazo[1,5-a]pyrazin-3-yl)bicyclo[2.2.1]heptan-1-yl)carbamate

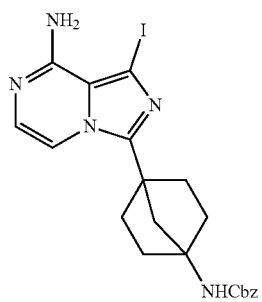 [SMILES: Nc1nccn2c(C34CCC(NC(=O)OCc5ccccc5)(CC3)C4)nc(I)c12]

To a suspension of compound A-3 (1.5 g, 2.87 mmol) in IPA (15 mL) was added NH$_4$OH (3 mL), and the mixture was heated to 110° C. and maintained at this temperature for 6 h. The mixture was then concentrated and added with saturated aqueous NaHCO$_3$ solution (20 mL). Ethyl acetate (30 mL×2) was added for extraction. The organic phase was washed with saturated aqueous NaCl solution, separated, dried over Na$_2$SO$_4$, filtered and evaporated. The residue was purified by column chromatography (ethyl acetate/petroleum ether=1:1) to give the desired compound A-4 (1.1 g, yield: 77%).

Synthetic Route of Intermediate B-3

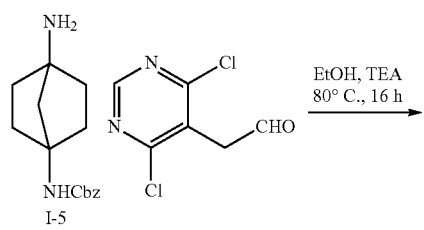

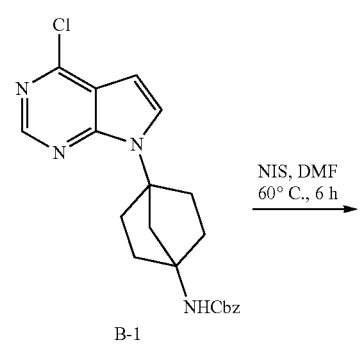

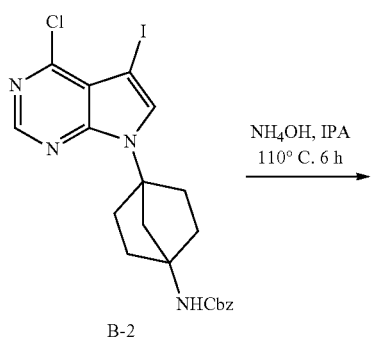

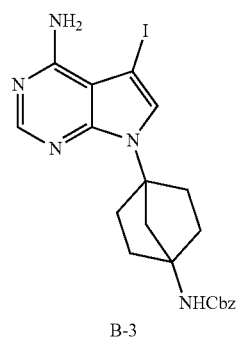

B-1: benzyl(4-(4-chloro-7H-pyrrolo[2,3-d]pyrimidin-7-yl)bicyclo[2.2.1]heptan-1-yl)carbamate

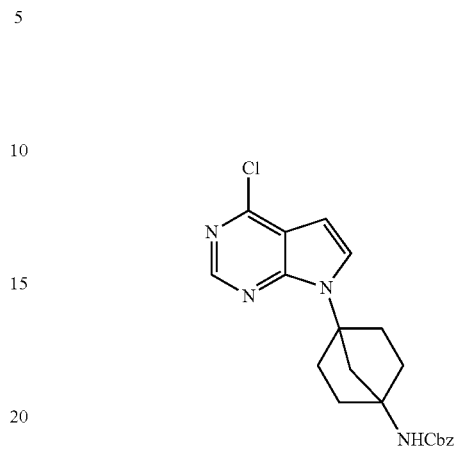

A solution of 2-(4,6-dichloropyrimidin-5-yl)acetaldehyde (735 mg, 3.8 mmol), benzyl (4-aminobicyclo[2.2.1]heptan-1-yl)carbamate (1 g, 3.8 mmol) and Et$_3$N (389 mg, 3.8 mmol) in EtOH (20 mL) was heated to 80° C. and maintained at this temperature for 16 h. The mixture was concentrated, added with water (20 mL), and extracted with ethyl acetate (20 mL×2). The organic phase was separated, dried over Na$_2$SO$_4$, filtered and evaporated, and the residue was purified by column chromatography (EA/PE=1:4) to give the desired compound B-1 (1.25 g, yield: 83%). LC-MS m/z=397.1[M+1]$^+$.

B-2: benzyl (4-(4-chloro-5-iodo-7H-pyrrolo[2,3-d]pyrimidin-7-yl)bicyclo[2.2.1]heptan-1-yl) carbamate

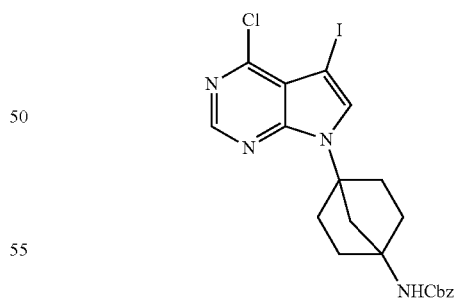

To a solution of compound B-1 (1.25 g, 3.16 mmol) in DMF (10 mL) was added NIS (950 mg, 4.2 mmol), and the mixture was heated to 60° C. and maintained at this temperature for 6 h. The mixture was poured into water (20 mL) and extracted with ethyl acetate (20 mL×2). The organic phase was separated, dried over Na$_2$SO$_4$, filtered and evaporated, and the residue was purified by column chromatography (EA/PE=1:4) to give the desired compound (0.09 g, yield: 66%). LC-MS m/z, 523.1[M+1]$^+$.

B-3: benzyl (4-(4-amino-5-iodo-7H-pyrrolo[2,3-d]pyrimidin-7-yl)bicyclo[2.2.1]heptan-1-yl) carbamate

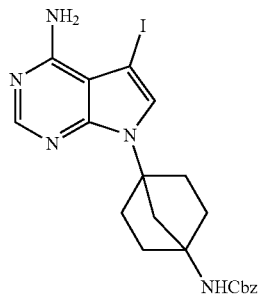 [SMILES: Nc1ncnc2c1c(I)cn2C12CCC(NC(=O)OCc3ccccc3)(CC1)C2]

To a solution of benzyl (4-(4-chloro-5-iodo-7H-pyrrolo[2,3-d]pyrimidin-7-yl)bicyclo[2.2.1]heptan-1-yl)carbamate (B-2) (1.09 g, 2.08 mmol) in IPA (10 mL) was added NH$_4$OH (2 mL), and the mixture was heated to 110° C. and maintained at this temperature for 6 h. The mixture was then concentrated, poured into aqueous NaHCO$_3$ solution, and extracted with DCM (20 mL×2). The organic phase was separated, dried, filtered and concentrated, and the residue was purified by column chromatography (MeOH/DCM=1:20) to give the desired compound B-3 (900 mg, yield: 86%).

Synthetic Route of Intermediate C-4

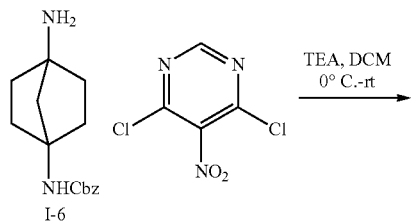

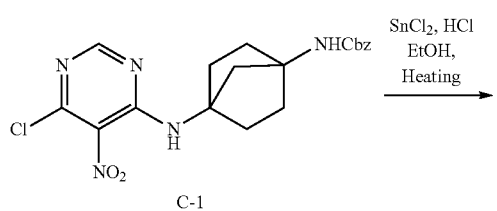

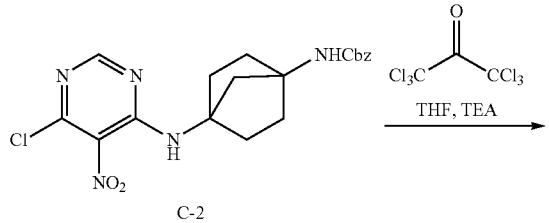

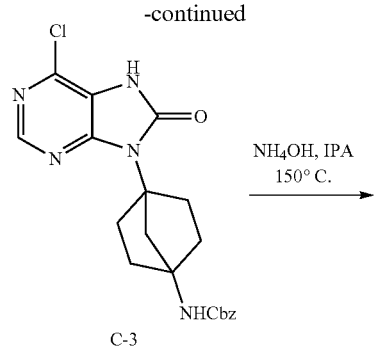

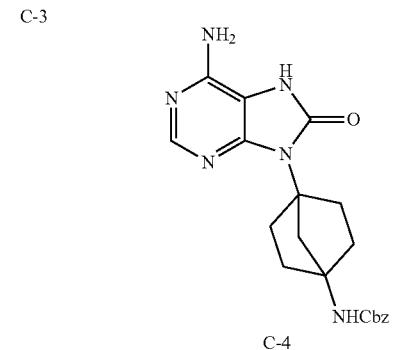

C-1: benzyl (4-((6-cloro-5-nitropyrimidin-4-yl)amino)bicyclo[2.2.1]heptan-1-yl)carbamate

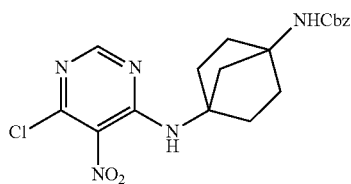 [SMILES: Nc1c(Cl)ncnc1NC12CCC(NC(=O)OCc3ccccc3)(CC1)C2]

A solution of 4,6-dichloro-5-nitropyrimidine (518 mg, 2.68 mmol), benzyl (4-aminobicyclo[2.2.1]heptan-1-yl)carbamate (I-5) (698 mg, 2.68 mmol) and Et$_3$N (1.1 g, 10.72 mmol) in DCM (20 mL) was stirred at room temperature for 4 h. The solvent was removed, and the residue was treated with ethyl acetate (50 mL) and washed with saturated aqueous NaCl solution. The organic phase was separated, dried over Na$_2$SO$_4$, filtered and concentrated, and the residue was purified by column chromatography (EA/PE=1:4) to give the desired compound C-1 (633 mg, yield: 57%).

C-2: benzyl (4-((5-amino-6-chloropyrimidin-4-yl)amino)bicyclo[2.2.1]heptan-1-yl)carbamate

To a solution of compound C-1 (400 mg, 0.96 mmol) in a mixed solvent (EtOH/H$_2$O 20 mL/4 mL) were added Fe powder (268 mg, 4.8 mmol) and NH₄Cl (254 mg, 4.8 mmol). The mixture was then heated to reflux for 1 h. After being cooled to room temperature, the mixture was filtered and washed with MeOH (10 mL). The filtrate was concentrated, and the crude product was purified by column chromatography (EA/PE=1:4) to give the desired compound C-2 (292 mg, yield: 79%).

C-3: benzyl (4-(6-chloro-8-oxo-7,8-dihydropurin-9-yl)bicyclo[2.2.1]heptan-1-yl)carbamate

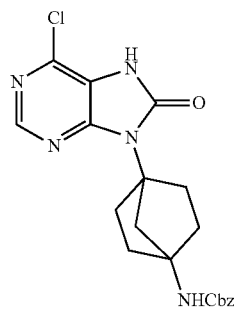 [SMILES: O=C(NC12CCC(n3c(=O)[nH]c4c(Cl)ncnc43)(CC1)C2)OCc1ccccc1]

To a solution of compound C-2 (290 mg, 0.75 mmol) in DCM (10 mL) at 0° C. were added Et₃N (166 mg, 1.5 mmol) and triphosgene (291 mg, 0.9 mmol), and the mixture was stirred at 0° C. for 2 h. The mixture was then poured into water (20 mL) and the organic phase was separated, and then the aqueous solution was extracted with DCM (10 mL×2) to separate the organic phase. The combined organic phases were dried over Na₂SO₄, filtered and concentrated to give crude C-3 (316 mg), which was directly used in the next step without purification.

C-4: benzyl (4-(6-amino-8-oxo-7,8-dihydropurin-9-yl)bicyclo[2.2.1]heptan-1-yl)carbamate

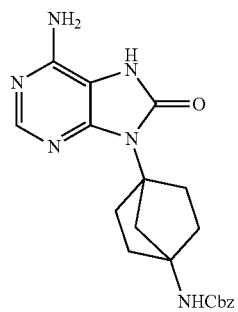 [SMILES: Nc1ncnc2c1[nH]c(=O)n2C12CCC(NC(=O)OCc3ccccc3)(CC1)C2]

To a solution of compound C-3 (310 mg, 0.75 mmol) in IPA (10 mL) was added NH₄OH (2 mL), and the mixture was heated to 150° C. and maintained at this temperature for 24 h. The mixture was then concentrated, poured into aqueous NaHCO₃ solution and extracted with DCM (20 mL×2). The organic phase was separated, dried, filtered and concentrated, and the residue was purified by column chromatography (MeOH/DCM=1:20) to give the desired compound C-4 (100 mg, yield: 34%). LC-MS m/z=395.1 [M+1]⁺.

Synthetic Route of Intermediate D-5

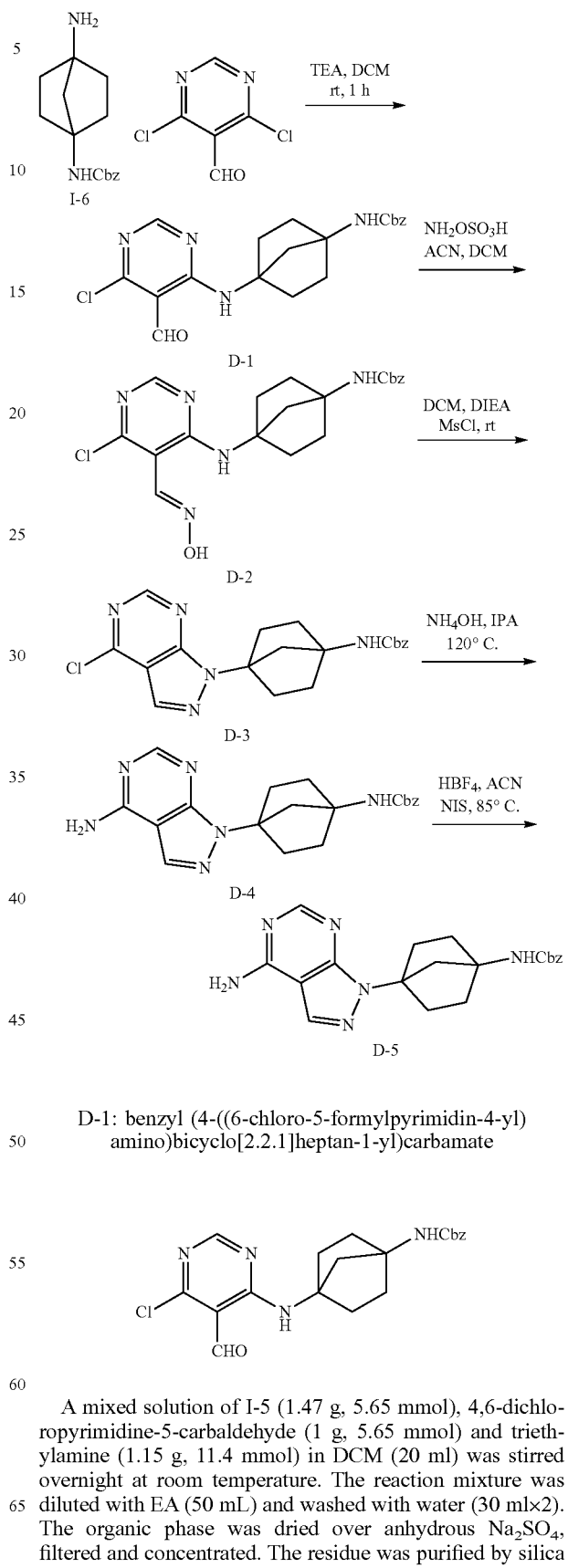

D-1: benzyl (4-((6-chloro-5-formylpyrimidin-4-yl)amino)bicyclo[2.2.1]heptan-1-yl)carbamate A mixed solution of I-5 (1.47 g, 5.65 mmol), 4,6-dichloropyrimidine-5-carbaldehyde (1 g, 5.65 mmol) and triethylamine (1.15 g, 11.4 mmol) in DCM (20 ml) was stirred overnight at room temperature. The reaction mixture was diluted with EA (50 mL) and washed with water (30 ml×2). The organic phase was dried over anhydrous Na₂SO₄, filtered and concentrated. The residue was purified by silica gel column chromatography (eluent: petroleum ether/ethyl acetate=1:1) to give the desired product D-1 (1.24 g, 55%). LC-MS m/z=401.0 [M+1]⁺.

D-2: benzyl (E)-(4-((6-chloro-5-((hydroxyimino) methyl)pyrimidin-4-yl)amino)bicyclo[2.2.1]heptan-1-yl)carbamate

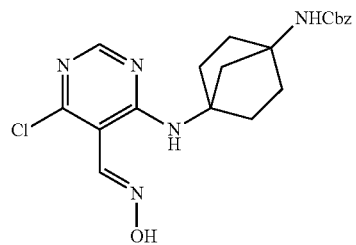 [SMILES: O=C(NC12CCC(Nc3ncnc(Cl)c3/C=N/O)(CC1)C2)OCc1ccccc1]

A mixed solution of D-1 (1.2 g, 3.0 mmol), hydroxylamine-O-sulfonic acid (0.41 g, 3.6 mmol) in DCM/ACN (50 ml/50 mL) was stirred at room temperature for 16 h and then stirred at 50° C. for 6 h. After being cooled, the mixture was concentrated to 10 ml, and the concentrate was filtered and washed with ACN (2 mL) to give the desired product D-2 (1.0 g, 81%). LC-MS m/z=416.0[M+1]⁻.

D-3: benzyl (4-(4-chloro-1H-pyrazolo[3,4d]pyrimidin-1-yl)bicyclo[2.2.1]heptan-1-yl) carbamate

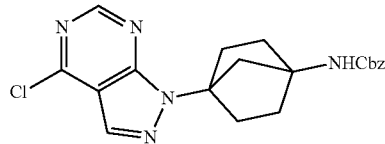 [SMILES: O=C(NC12CCC(n3ncc4c(Cl)ncnc43)(CC1)C2)OCc1ccccc1]

To a solution of D-2 (1.0 g, 2.41 mmol) in DCM (100 mL) was added DIEA (4 mL), and then TsCl (0.23 mL, 2.9 mmol) was added dropwise. After being stirred at room temperature for 3 h, the reaction mixture was treated with water (100 mL). The organic phase was washed with brine (30 mL×2), dried over anhydrous Na₂SO₄, filtered and concentrated. The residue was purified by silica gel column chromatography (eluent: ethyl acetate/petroleum ether=1:6) to give the desired product D-3 (400 mg, 42%). LC-MS m/z=398.1 [M+1]⁺.

D-4: benzyl (4-(4-amino-1H-pyrazolo[3,4-d]pyrimidin-1-yl)bicyclo[2.2.1]heptan-1-yl) carbamate

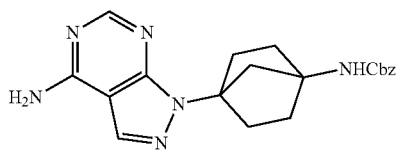 [SMILES: Nc1ncnc2c1cnn2C12CCC(NC(=O)OCc3ccccc3)(CC1)C2]

A mixture of D-3 (400 mg, 1.0 mmol) and ammonium hydroxide (30%, 5 mL) in isopropanol (20 mL) was stirred in a sealed tube at 120° C. for 6 h. The solvent was evaporated off and the residue was purified by silica gel column chromatography (eluent: PE/EA=2:1) to give the desired product D-4 (280 mg, 73.4%).

D-5: benzyl (4-(4-amino-3-iodo-1H-pyrazolo[3,4-d] pyrimidin-1-yl)bicyclo[2.2.1]heptan-1-yl)carbamate

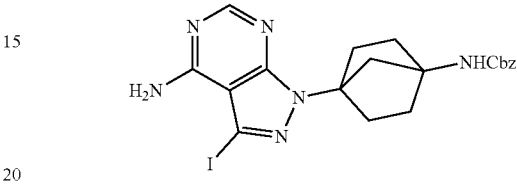

A mixture of D-4 (190 mg, 0.5 mmol), NIS (400) mg, 1.78 mmol) and HBF₄ (50%, 19.6 mmol, 4 mL) in ACN (2.5 mL) was heated to 85° C. in a sealed tube and stirred for 6 h. After the mixture was cooled, the reaction was quenched with saturated NaHCO₃ and EA (50 mL×2) was added for extraction. The organic phase was dried over anhydrous Na₂SO₄, filtered and concentrated. The residue was purified by silica gel column chromatography (eluent: PE/EA=1:1-1:0) to give the desired product D-5 (96 mg, 38.1%). LC-MS m/z=505.0 [M+1]⁺.

Example 1

Synthetic Route of Compound A-7-n

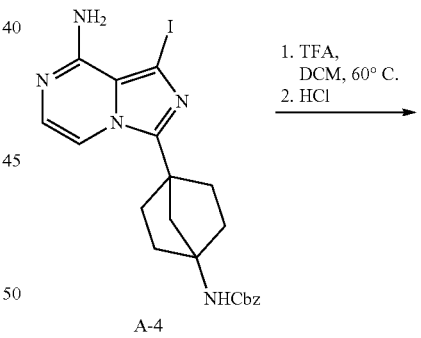

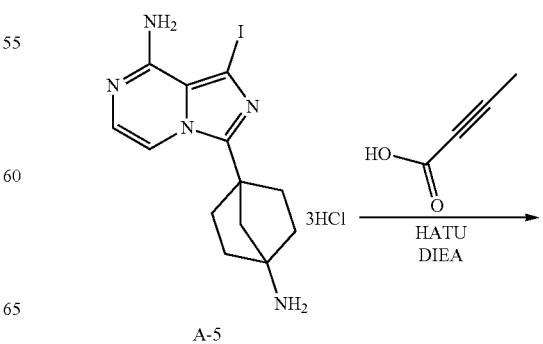

-continued

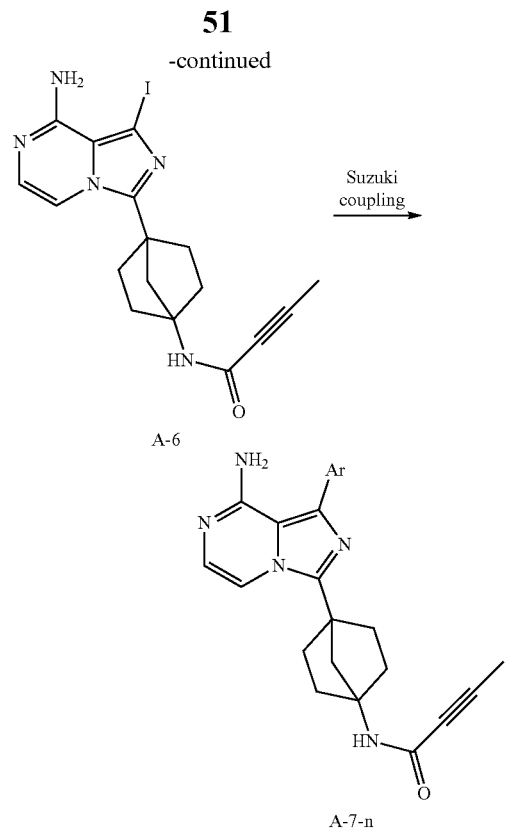

A-5: 3-(4-aminobicyclo[2.2.1]heptan-1-yl)-1-iodo-imidazo[1,5-a]pyrazin-8-amine

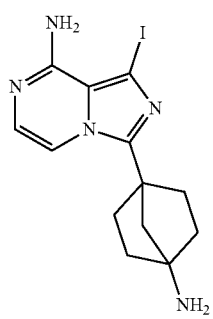 [SMILES: Nc1nccn2c(C34CCC(N)(CC3)C4)nc(I)c12]

A solution of compound A-4 (1 g, 1.99 mmol) in a mixed solvent of TFA/DCM (10 mL/10 mL) was heated to 60° C. and maintained at this temperature for 6 h. The mixture was concentrated and added with DCM (20 mL×2). The resulting mixture was concentrated, dissolved in DCM (20 mL), added with a solution of HCl in dioxane (5 mL), and stirred at room temperature for 10 min. The mixture was evaporated and added with DCM (20 mL×2), and the resulting mixture was evaporated and added with DME (20 mL). The mixture was stirred at room temperature for 30 min. filtered and then washed with DME (10 mL×2). The obtained compound A-5 was directly used in the next step without purification. LC-MS m/z=370.1 [M+1]$^+$.

A-6: N-(4-(8-amino-1-iodoimidazo[1,5-a]pyrazin-3-yl)bicyclo[2.2.1]heptan-1-yl)but-2-ynamide A solution of compound A-5 (1.35 g, 2.8 mmol). DIEA (3.28 g, 25.2 mmol), but-2-ynoic acid (235 mg, 2.8 mmol) and HATU (1.06 g, 2.8 mmol) in DMF (20 mL) was stirred at room temperature for 30 min. The mixture was poured into water (30 mL) and extracted with ethyl acetate (30 mL×2). The organic phase was washed with saturated aqueous NaCl solution, separated, dried over Na$_2$SO$_4$, filtered and evaporated. The residue was purified by column chromatography (ethyl acetate/petroleum ether=2:3) to give the desired compound A-6 (800 mg, yield: 65%).

A-7-1: 4-(8-amino-3-(4-(but-2-ynamido)bicyclo[2.2.1]heptan-1-yl)imidazo[1,5-a]pyrazin-1-yl)-N-(pyridin-2-yl)benzamide

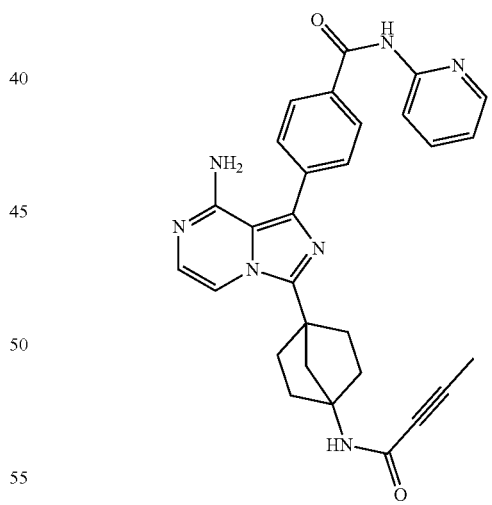

A solution of compound A-6 (30 mg, 0.069 mmol), (4-(pyridin-2-ylcarbamoyl)phenyl) boronic acid (II-1) (20 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-1 (10 mg, yield: 30%). LC-MS m/z=506.2 [M+1]⁺.

A-7-2: 4-(8-amino-3-(4-(but-2-ynamido)bicyclo[2.2.1]heptan-1-yl)imidazo[1,5-a]pyrazin-1-yl)-N-(4-fluoropyridin-2-yl)benzamide

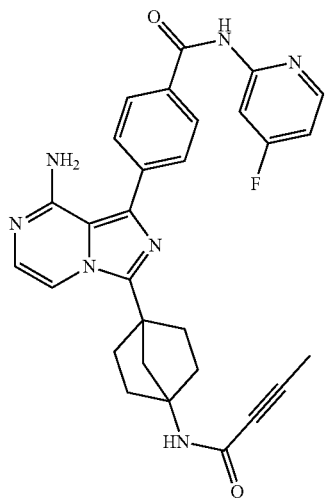

A solution of compound A-6 (30 mg, 0.069 mmol), (4-((4-fluoropyridin-2-yl)carbamoyl) phenyl)boronic acid (II-2) (22 mg, 0.085 mmol), Pd[PPh₃]₄ (8 mg, 0.0069 mmol) and Cs₂CO₃ (45 mg, 0.138 mmol) in a mixed solvent of DMF/H₂O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na₂SO₄, filtered and evaporated. The residue was purified by column chromatography (ethyl acetate/petroleum ether=1:1) to give the desired compound A-7-2 (15 mg, yield: 34%). LC-MS m/z=524.0 [M+1]⁺.

A-7-3: 4-(8-amino-3-(4-(but-2-ynamido)bicyclo[2.2.1]heptan-1-yl)imidazo[1,5-a]pyrazin-1-yl)-N-(4-(trifluoromethyl)pyridin-2-yl)benzamide

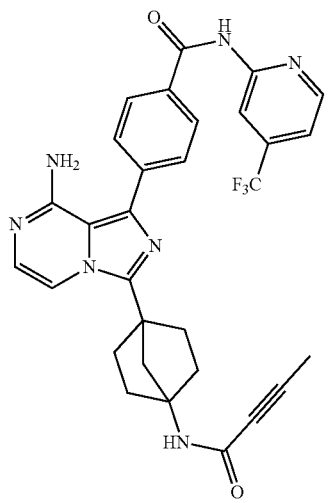 [SMILES: CC#CC(=O)NC12CCC(c3nc(-c4ccc(C(=O)Nc5cc(C(F)(F)F)ccn5)cc4)c4c(N)nccn34)(CC1)C2]

A solution of compound A-6 (30 mg, 0.069 mmol), (4-((4-(trifluoromethyl)pyridin-2-yl) carbamoyl)phenyl)boronic acid (II-3) (26 mg, 0.085 mmol), Pd[PPh₃]₄ (8 mg, 0.0069 mmol) and Cs₂CO₃ (45 mg, 0.138 mmol) in a mixed solvent of DME/H₂O (1.5 mL/0.3 mL) was heated to 140° C. and maintained at this temperature for 3 h. The mixture was concentrated, added with water (20 mL) and extracted with ethyl acetate (20 mL×2). The organic phase was separated, dried over Na₂SO₄, filtered and evaporated. The residue was purified by column chromatography (ethyl acetate/petroleum ether=1:1) to give the desired compound A-7-3 (12 mg, yield: 31%). LC-MS m/z=574.2[M+1]⁺.

A-7-4: 4-(8-amino-3-(4-(but-2-ynamido)bicyclo[2.2.1]heptan-1-yl)imidazo[1,5-a]pyrazin-1-yl)-N-(4-methylpyridin-2-yl)benzamide

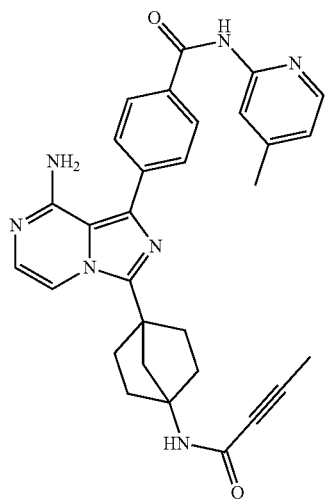 [SMILES: CC#CC(=O)NC12CCC(c3nc(-c4ccc(C(=O)Nc5cc(C)ccn5)cc4)c4c(N)nccn34)(CC1)C2]

A solution of compound A-6 (30 mg, 0.069 mmol), (4-((4-methylpyridin-2-yl)carbamoyl) phenyl)boronic acid (II-4) (22 mg, 0.085 mmol). Pd[PPh₃]₄ (8 mg, 0.0069 mmol) and Cs₂CO₃ (45 mg, 0.138 mmol) in a mixed solvent of DMF/H₂O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na₂SO₄, filtered and evaporated. The residue was purified by column chromatography (ethyl acetate/petroleum ether=1:1) to give the desired compound A-7-4 (14 mg, yield: 39%). LC-MS m/z=520.2 [M+1]⁺.

A-7-5: 4-(8-amino-3-(4-(but-2-ynamido)bicyclo[2.2.1]heptan-1-yl)imidazo[1,5-a]pyrazin-1-yl)-N-(4-cyanopyridin-2-yl)benzamide

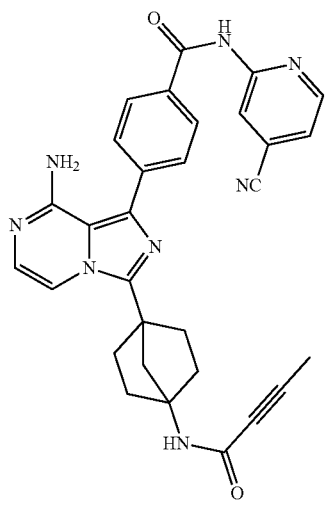 [SMILES: CC#CC(=O)NC12CCC(c3nc(-c4ccc(C(=O)Nc5cc(C#N)ccn5)cc4)c4c(N)nccn34)(CC1)C2]

A solution of compound A-6 (30 mg, 0.069 mmol), (4-((4-cyanopyridin-2-yl)carbamoyl) phenyl)boronic acid (II-5) (23 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-5 (12 mg, yield: 33%). LC-MS m/z=531.0 [M+1]$^+$.

A-7-6: 4-(8-amino-3 (4-(but-2-ynamido)bicyclo[2.2.1]heptan-1-yl)imidazol[1,5-a]pyrazin-1-yl)-2-fluoro-N-(pyridin-2-yl)benzamide

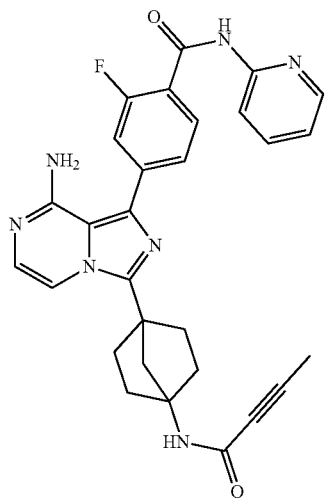 [SMILES: CC#CC(=O)NC12CCC(c3nc(-c4ccc(C(=O)Nc5ccccn5)c(F)c4)c4c(N)nccn34)(CC1)C2]

A solution of compound A-6 (30 mg, 0.069 mmol), (3-fluoro-4-(pyridin-2-ylcarbamoyl) phenyl)boronic acid (II-6)(22 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-6 (15 mg, yield: 42%). LC-MS m/z=524.2 [M+1]$^+$.

A-7-7: 4-(8-amino-3-(4-(but-2-ynamido)bicyclo[2.2.1]heptan-1-yl)imidazol[1,5-a]pyrazin-1-yl)-N-(thiazol-2-yl)benzamide

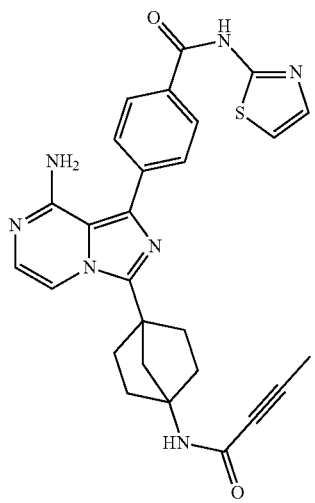 [SMILES: CC#CC(=O)NC12CCC(c3nc(-c4ccc(C(=O)Nc5nccs5)cc4)c4c(N)nccn34)(CC1)C2]

A solution of compound A-6 (30 mg, 0.069 mmol), (4-(thiazol-2-ylcarbamoyl)phenyl) boronic acid (II-7)(28 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated to dryness. The residue was purified by column chromatography (ethyl acetate/petroleum ether=1:1) to give the desired compound A-7-7 (13 mg, yield: 37%). LC-MS m/z=512.0 [M+1]$^+$.

A-7-8: 4-(8-amino-3-(4-(but-2-ynamido)bicyclo[2.2.1]heptan-1-yl)imidazo[1,5-a]pyrazin-1-yl)-3-fluoro-N-(pyridin-2-yl)benzamide

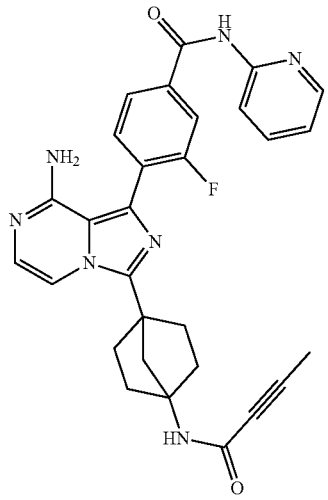 [SMILES: CC#CC(=O)NC12CCC(c3nc(-c4ccc(C(=O)Nc5ccccn5)cc4F)c4c(N)nccn34)(CC1)C2]

A solution of compound A-6 (30 mg, 0.069 mmol), (2-fluoro-4-(pyridin-2-ylcarbamoyl) phenyl)boronic acid (11-) (22 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-8 (14 mg, yield: 39%). LC-MS m/z=524.0 [M+1]$^+$.

A-7-9: 4-(8-amino-3-(4-(but-2-ynamido)bicyclo[2.2.1]heptan-1-yl)imidazo[1,5-a]pyrazin-1-yl)-3-fluoro-N-(4-(trifluoromethyl)pyridin-2-yl)benzamide

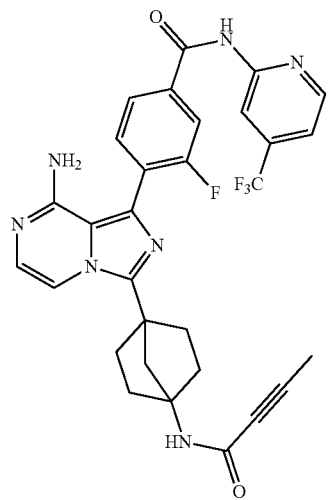 [SMILES: CC#CC(=O)NC12CCC(c3nc(-c4ccc(C(=O)Nc5cc(C(F)(F)F)ccn5)cc4F)c4c(N)nccn34)(CC1)C2]

A solution of compound A-6 (30 mg, 0.069 mmol), (2-fluoro-4-((4-(trifluoromethyl) pyridin-2-yl)carbamoyl) phenyl)boronic acid (II-9) (28 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-9 (19 mg, yield: 47%). LC-MS m/z=592.0 [M+1]$^+$.

A-7-10: 4-(8-amino-3-(4-(but-2-ynamido)bicyclo[2.2.1]heptan-1-yl)imidazo[1,5-]pyrazin-1-yl)-3-methoxy-N-(4-(trifluoromethyl)pyridin-2-yl)benzamide

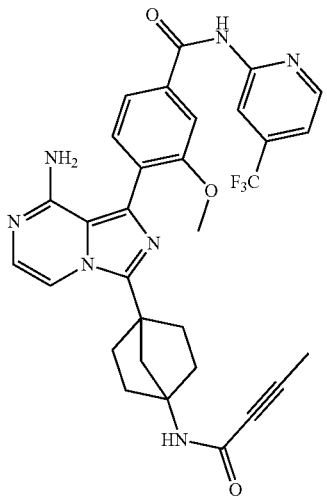 [SMILES: CC#CC(=O)NC12CCC(c3nc(-c4ccc(C(=O)Nc5cc(C(F)(F)F)ccn5)cc4OC)c4c(N)nccn34)(CC1)C2]

A solution of compound A-6 (30 mg, 0.069 mmol), (2-methoxy-4-((4-(trifluoromethyl) pyridin-2-yl)carbamoyl) phenyl)boronic acid (II-10) (29 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-10 (16 mg, yield: 38%). LC-MS m/z=604.0 [M+1]$^+$.

A-7-11: N-(4-(8-amino-3-(4-(but-2-ynamido)bicyclo[2.2.1]heptan-1-yl)imidazo[1,5-a]pyrazin-1-yl)benzyl)-2-methoxy benzamide

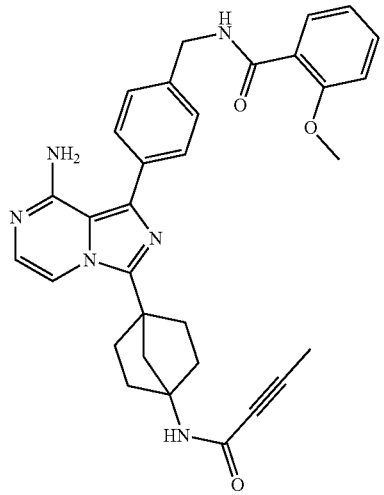 [SMILES: CC#CC(=O)NC12CCC(c3nc(-c4ccc(CNC(=O)c5ccccc5OC)cc4)c4c(N)nccn34)(CC1)C2]

A solution of compound A-6 (30 mg, 0.069 mmol), 2-methoxy-N-(4-(4,4,5,5-tetramethyl-1,3,2-dioxaborolan-2-yl)benzyl)benzamide (II-11) (31 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL). The organic phase was separated, dried over Na$_2$SO$_4$, filtered and evaporated. The residue was purified by column chromatography (ethyl acetate/petroleum ether:=1:1) to give the desired compound A-7-11 (21 mg, yield: 50%). LC-MS m/z=549.3 [M+1]$^+$.

A-7-12: N-(4-(8-amino-3-(4-(but-2-ynamido)bicyclo[2.2.1]heptan-1-yl)imidazo[1,5-a]pyrazin-1-yl)benzyl)-5-fluoro-2-methoxybenzamide

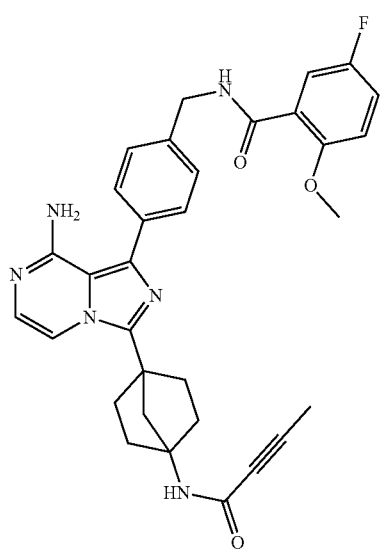 [SMILES: CC#CC(=O)NC12CCC(c3nc(-c4ccc(CNC(=O)c5cc(F)ccc5OC)cc4)c4c(N)nccn34)(CC1)C2]

A solution of compound A-6 (30 mg, 0.069 mmol), 5-fluoro-2-methoxy-N-(4-(4,4,5,5-tetramethyl-1,3,2-dioxaborolan-2-yl)benzyl)benzamide (II-12) (33 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over anhydrous Na$_2$SO$_4$, filtered and evaporated. The residue was purified by column chromatography (ethyl acetate/petroleum ether=1:1) to give the desired compound A-7-12 (24 mg, yield: 56%). LC-MS m/z=567.0[M+1]$^+$.

A-7-13: N-(4-(8-amino-3-(4-(but-2-ynamido)bicyclo[2.2.1]heptan-1-yl)imidazo[1,5-a]pyrazin-1-yl)benzyl)-4-fluoro-2-methoxybenzamide

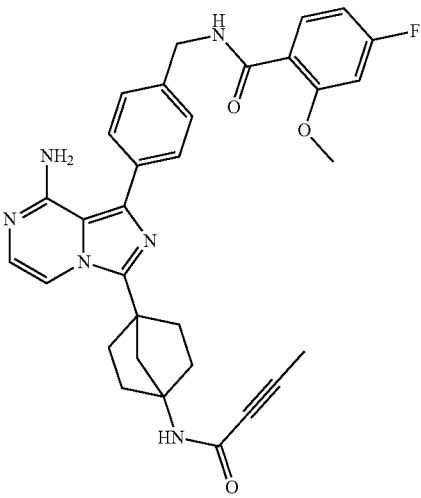 [SMILES: CC#CC(=O)NC12CCC(c3nc(-c4ccc(CNC(=O)c5ccc(F)cc5OC)cc4)c4c(N)nccn34)(CC1)C2]

A solution of compound A-6 (30 mg, 0.069 mmol), 4-fluoro-2-methoxy-N-(4-(4,4,5,5-tetramethyl-1,3,2-dioxaborolan-2-yl)benzyl)benzamide (II-13) (33 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated. The residue was purified by column chromatography (ethyl acetate/petroleum ether=1:1) to give the desired compound A-7-13 (26 mg, yield: 60%). LC-MS m/z=567.1 [M+1]+.

A-7-14: N-(4-(8-amino-1-(4-phenoxyphenyl)imidazol[1,5-a]pyrazin-3-yl)bicyclo[2.2.1]heptan-1-yl)but-2-ynamide

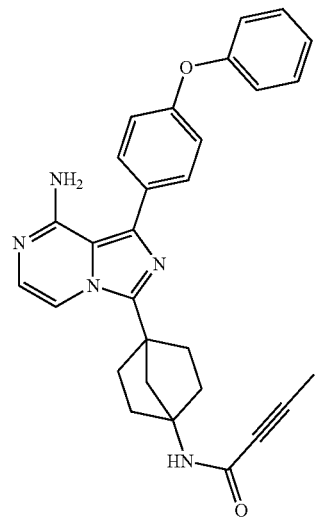 [SMILES: CC#CC(=O)NC12CCC(c3nc(-c4ccc(Oc5ccccc5)cc4)c4c(N)nccn34)(CC1)C2]

A solution of compound A-6 (30 mg, 0.069 mmol), 4-phenoxyphenylboronic acid (18 mg, 0.085 mmol), Pd[PPh$_3$]$_4$ (8 mg, 0.0069 mmol) and Cs$_2$CO$_3$ (45 mg, 0.138 mmol) in a mixed solvent of DME/H$_2$O (1.5 mL/0.3 mL) was heated to 80° C. and maintained at this temperature for 3 h. The mixture was concentrated, added with water (20 mL) and extracted with ethyl acetate (20 mL×2). The organic phase was separated, dried over Na$_2$SO$_4$, filtered and evaporated to dryness. The residue was purified by column chromatography (ethyl acetate/petroleum ether=1:1) to give the desired compound A-7-14 (19 mg, yield: 49%). LC-MS m/z=478.0 [M+1]+.

Synthetic Route of Compound A-10-n

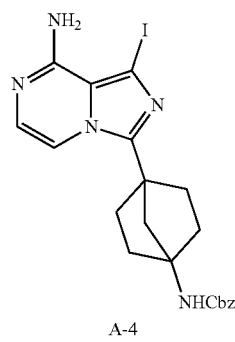

-continued

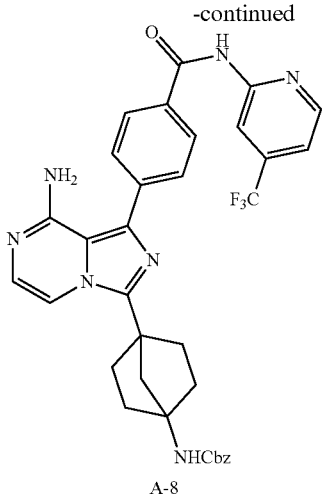

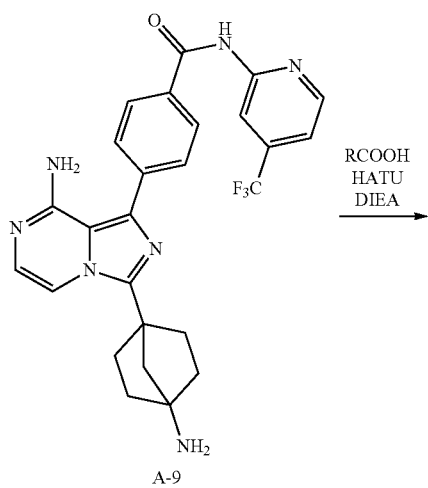

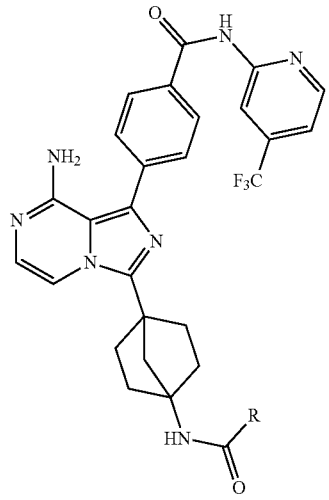

A-8: benzyl (4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)carbamate

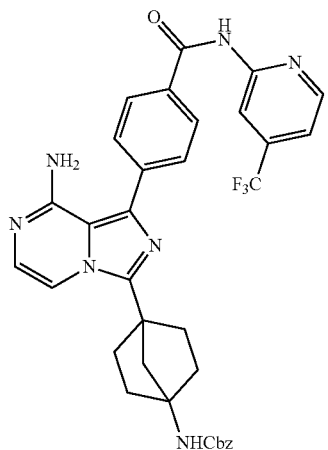 [SMILES: Nc1nccn2c(C34CCC(NC(=O)OCc5ccccc5)(CC3)C4)nc(-c3ccc(C(=O)Nc4cc(C(F)(F)F)ccn4)cc3)c12]

A solution of benzyl (4-(8-amino-1-iodoimidazo[1,5-a]pyrazin-3-yl)bicyclo[2.2.1]heptan-1-yl)carbamate (A-4) (300 mg, 0.6 mmol), (4-((4-(trifluoromethyl)pyridin-2-yl)carbamoyl)phenyl)boronic acid (II-3) (229 mg, 0.738 mmol), Pd[PPh$_3$]$_4$ (69 mg, 0.06 mmol) and Cs$_2$O$_3$ (239 mg, 0.738 mmol) in a mixed solvent of DME:H$_2$O (2.5 mL:0.5 mL) was heated to 80° C. and stirred overnight. The mixture was concentrated, and the residue was purified by column chromatography (methanol/DCM=1.30) to give the desired compound A-B (265 mg, yield: 69%).

A-9: 4-(8-amino-3-(4-aminobicyclo[2.2.1]heptan-1-yl)imidazo[1,5-a]pyrazin-1-yl)-N-(4-(trifluoromethyl)pyridin-2-yl)benzamide

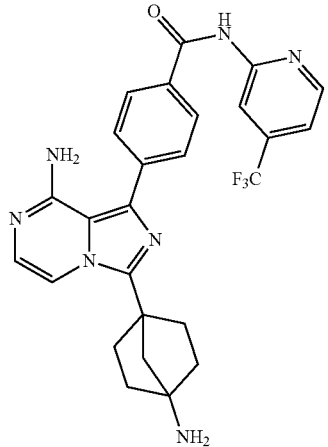 [SMILES: Nc1nccn2c(C34CCC(N)(CC3)C4)nc(-c3ccc(C(=O)Nc4cc(C(F)(F)F)ccn4)cc3)c12]

A solution of compound A-8 (265 mg, 0.42 mmol) in a mixed solvent of DCM/TFA (10 mL:10 mL) was heated to 60° C. and stirred for 18 h. After the mixture was evaporated to dryness, DCM (20 mL×2) was added, and the resulting mixture was concentrated. The residue was dissolved in DCM (30 mL), and then the solution was added to a solution of HCl in dioxane. After the mixture was evaporated to dryness, DCM (20 mL×2) was then added, and the resulting mixture was concentrated, followed by the addition of isopropyl ether (30 mL). After being stirred for 2 h, the mixture was filtered and washed with isopropyl ether (10 mL×2) to give the hydrochloride of the desired product A-9 (1% mg), which was directly used in the next step without purification.

A-10-1: (E)-4-(8-amino-3-(4-(4-methoxybut-2-enamido)bicyclo[2.2.1]heptan-1-yl)imidazo[1,5-a]pyrazin-1-yl)-N-(4-(trifluoromethyl)pyridin-2-yl)benzamide

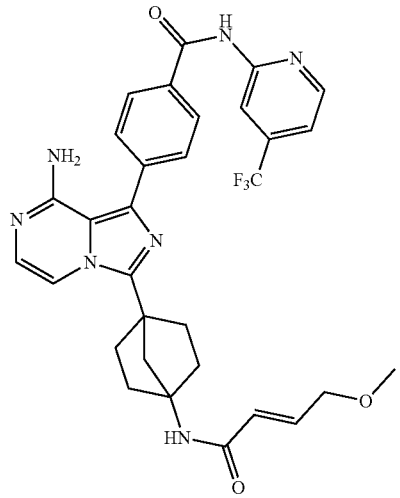 [SMILES: COC/C=C/C(=O)NC12CCC(c3nc(-c4ccc(C(=O)Nc5cc(C(F)(F)F)ccn5)cc4)c4c(N)nccn34)(CC1)C2]

A solution of compound A-9 (15 mg, 0.024 mmol), HATU (9.12 mg, 0.024 mmol), DIEA (16 mg, 0.12 mmol) and (E)-4-methoxybut-2-enoic acid (2.8 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (eluent: DCM/MeOH=20:1) to give the product A-10-1 (5 mg, yield: 35%). LC-MS m/z=606.1 [M+1]+.

A-10-2: (E)-4-(8-amino-3-(4-(4-(tetrahydropyrrol-1-yl)but-2-enamido)bicyclo[2.2.1]heptan-1-yl)imidazo[1,5-a]pyrazin-1-yl)-N-(4-(trifluoromethyl)pyridin-2-yl)benzamide

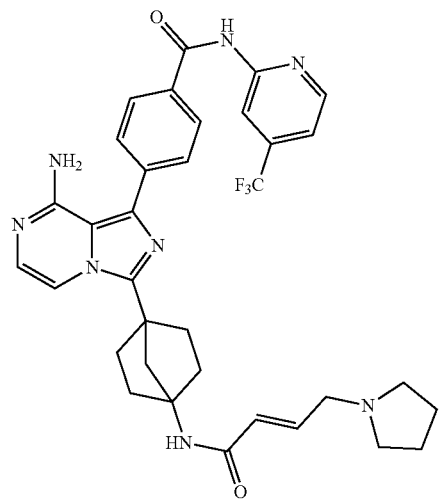 [SMILES: Nc1nccn2c(C34CCC(NC(=O)/C=C/CN5CCCC5)(CC3)C4)nc(-c3ccc(C(=O)Nc4cc(C(F)(F)F)ccn4)cc3)c12]

A solution of compound A-9 (15 mg, 0.024 mmol), HATU (9.12 mg, 0.024 mmol), DIEA (16 mg, 0.12 mmol) and (E)-4-(tetrahydropyrrol-1-yl)-but-2-enoic acid (4 mg, 0.024 mmol) in DMF (1 ml) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-2 (6 mg, yield: 38%). LC-MS m/z=645.0 [M+1]+.

A-10-3: 4-(3-(4-acrylamidobicyclo[2.2.1]heptan-1-yl)-8-aminoimidazo[1,5-a]pyrazin-1-yl)-N-(4-(trifluoromethyl)pyridin-2-yl)benzamide

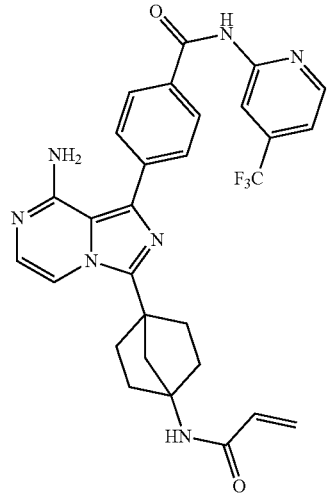 [SMILES: C=CC(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and acrylic acid (2 mg, 0.024 mmol) were stirred at room temperature for 1 h, and then the mixture was poured into water (1 ml) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-3 (5 mg, yield: 38%). LC-MS m/z=562.0[M+1]+.

A-10-4: 4-(3-(4-acetamidobicyclo[2.2.1]heptan-1-yl)-8-aminoimidazo[1,5-a]pyrazin-1-yl)-N-(4-(trifluoromethyl)pyridin-2-yl)benzamide

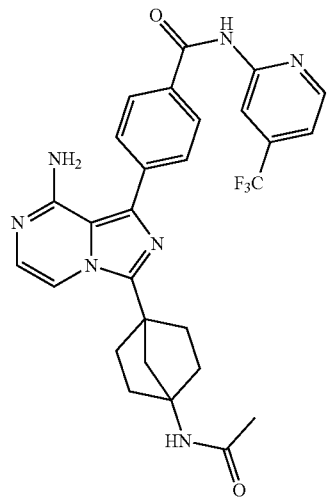 [SMILES: CC(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and acetic acid (1.5 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-4 (4 mg, yield: 31%). LC-MS m/z=550.0 [M+1]+.

A-10-5: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)-3-methyloxetane-3-carboxamide

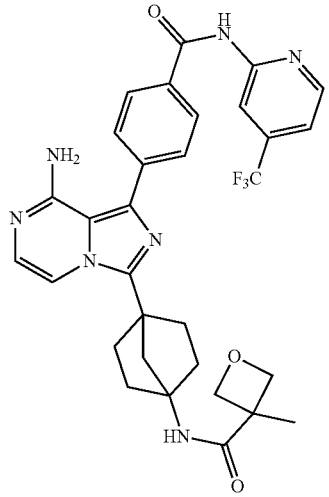 [SMILES: CC1(C(=O)NC23CCC(c4nc(-c5ccc(C(=O)Nc6cc(C(F)(F)F)ccn6)cc5)c5c(N)nccn45)(CC2)C3)COC1]

A solution of compound A-9 (15 mg, 0.024 mmol), HATU (9.12 mg, 0.024 mmol), DIEA (16 mg, 0.12 mmol) and 3-methyloxetane-3-carboxylic acid (3 mg, 0.024 mmol) in DMF (1 mL) was stirred at room temperature for 1 h, and then the mixture was poured into water (5 mL) and washed with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-5 (6 mg, yield: 40%). LC-MS m/z=606.1[M+1]+.

A-10.6: 4-(8-amino-3-(4-(2-hydroxy-2-methylpropanamido)bicyclo[2.2.1]heptan-1-yl)imidazo[1,5-a]pyrazin-1-yl-N-(4-(trifluoromethyl)pyridin-2-yl)benzamide

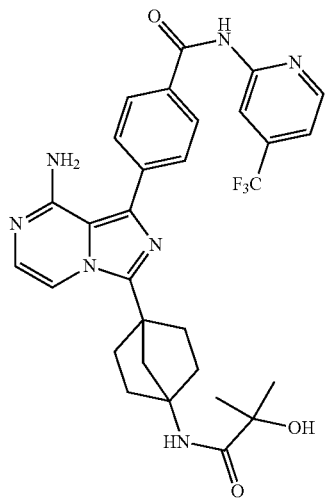 [SMILES: CC(C)(O)C(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and 2-hydroxy-2-methylpropionic acid (2.5 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-6 (6 mg, yield: 41%). LC-MS m/z=594.1 [M+1]+.

A-10-7: 4-(8-amino-3-(4-(2-methoxyacetamido)bicyclo[2.2.1]heptan-1-yl)imidazo[1,5-a]pyrazin-1-yl)-N-(4-(trifluoromethyl)pyridin-2-yl)benzamide A-10-8: 4-(8-amino-3-(4-(3-methoxypropanamido)bicyclo[2.2.1]heptan-1-yl)imidazo[1,5-a]pyrazin-1-yl)-N-(4-(trifluoromethyl)pyridin-2-yl)benzamide

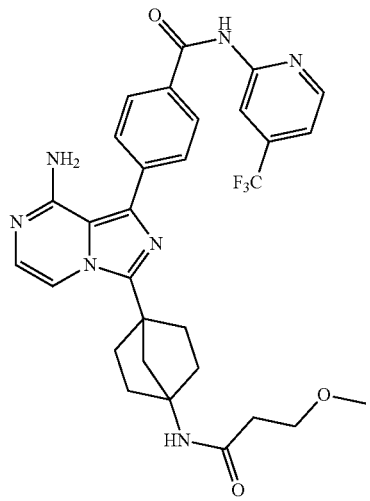

Compound A-9 (15 mg, 0.024 mmol). HATU (9.12 mg, 0.024 mmol), DIEA (16 mg, 0.12 mmol) and 3-methoxypropionic acid (2.5 mg, 0.024 mmol) were stirred at room temperature for 1 h. and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-8 (5 mg, yield: 35%). LC-MS m/z=594.1 [M+1]+.

A-10-9: 4-(8-amino-3-(4-(1-hydroxycyclopropanecarboxamido)bicyclo[2.2.1]heptan-1-yl)imidazo[1,5-a]pyrazin-1-yl)-N-(4-(trifluoromethyl)pyridin-2-yl)benzamide

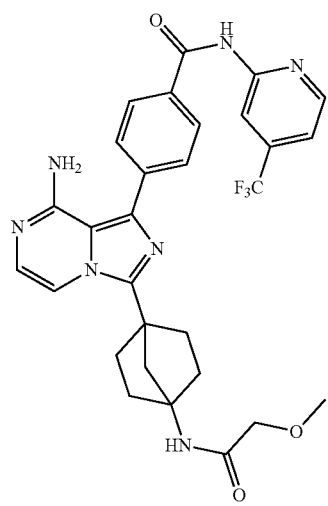 [SMILES: COCC(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and 2-methoxyacetic acid (2 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-7 (5 mg, yield: 36%). LC-MS m/z=580.1 [M+1]+.

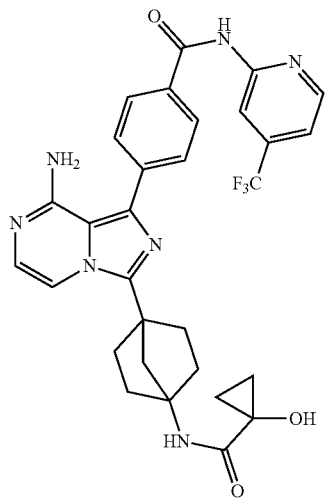 [SMILES: Nc1nccn2c(C34CCC(NC(=O)C5(O)CC5)(CC3)C4)nc(-c3ccc(C(=O)Nc4cc(C(F)(F)F)ccn4)cc3)c12]

A solution of compound A-9 (15 mg, 0.024 mmol), HATU (9.12 mg, 0.024 mmol), DIEA (16 mg, 0.12 mmol) and 1-hydroxycyclopropanecarboxylic acid (2.5 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-9 (5 mg, yield: 36%). LC-MS m/z=592.01 [M+H]+.

A-10-10: 4-(8-amino-3-(4-(2-morpholinoacetamido) bicyclo[2.2.1]heptan-1-yl)imidazo[1,5-a]pyrazin-1-yl)-N-(4-(trifluoromethyl)pyridin-2-yl)benzamide

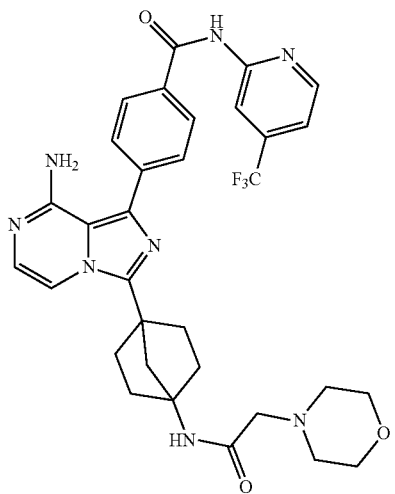 [SMILES: Nc1nccn2c(C34CCC(NC(=O)CN5CCOCC5)(CC3)C4)nc(-c3ccc(C(=O)Nc4cc(C(F)(F)F)ccn4)cc3)c12]

Compound A-9 (15 mg, 0.024 mmol), HATU (9.12 mg, 0.024 mmol), DIEA (16 mg, 0.12 mmol) and 2-morpholinoacetic acid (3.5 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-10 (7 mg, yield: 47%). LC-MS m/z=635.0 [M+1]+.

A-10-11: N-(4-(8-amino-1-(4-((4-(trifluoromethyl) pyridin-2-yl)carbamoyl)phenyl)imidazo [1,5-a] pyrazin-3-yl)bicyclo[2.2.1]heptan-1-yl)tetrahydrofuran-2-carboxamide

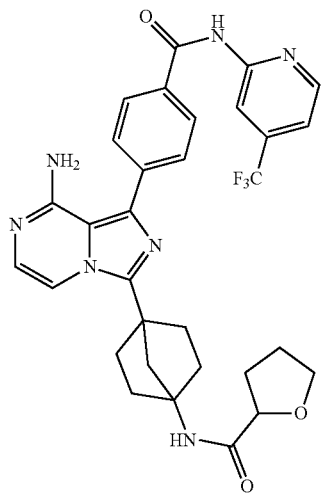 [SMILES: Nc1nccn2c(C34CCC(NC(=O)C5CCCO5)(CC3)C4)nc(-c3ccc(C(=O)Nc4cc(C(F)(F)F)ccn4)cc3)c12]

A solution of compound A-9 (15 mg, 0.024 mmol). HATU (9.12 mg, 0.024 mmol), DIEA (16 mg, 0.12 mmol) and tetrahydrofuran-2-carboxylic acid (2.8 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeO=20:1) to give the product A-10-11 (5 mg, yield: 35%). LC-MS m/z=606.0 [M+1]+.

A-10-12: 4-(8-amino-3-(4-(1-cyanocyclopropanecarboxamido)bicyclo[2.2.1]heptan-1-yl) imidazo[1,5-a] pyrazin-1-yl)-N-(4-(trifluoromethyl)pyridin-2-yl) benzamide

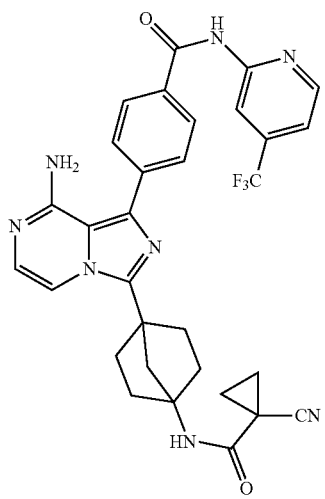 [SMILES: N#CC1(C(=O)NC23CCC(c4nc(-c5ccc(C(=O)Nc6cc(C(F)(F)F)ccn6)cc5)c5c(N)nccn45)(CC2)C3)CC1]

Compound A-9 (15 mg, 0.024 mmol), HATU (9.12 mg, 0.024 mmol), DIEA (16 mg, 0.12 mmol) and 1-cyanocyclopropanecarboxylic acid (2.7 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-12 (6 mg, yield: 42%). LC-MS m/z=601.3 [M+1]+.

A-10-13: 4-(8-amino-3-(4-(2-cyanoacetamido)bicyclo[2.2.1]heptan-1-yl)imidazo[1,5-a]pyrazin-1-yl)-N-(4-(trifluoromethyl)pyridin-2-yl)benzamide A-10-14: 4-(8-amino-3-(4-(2-cyanopropanamido)bicyclo[2.2.1]heptan-1-yl)imidazo[1,5-a]pyrazin-1-yl)-N-(4-(trifluoromethyl)pyridin-2-yl)benzamide

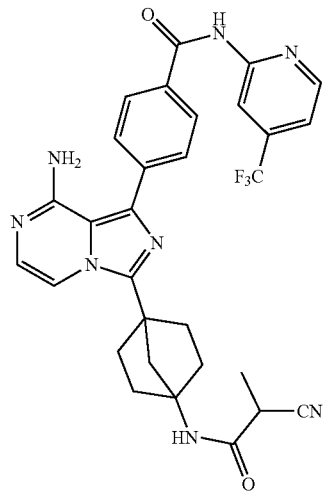

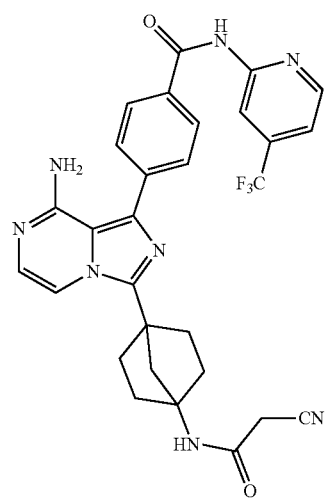 [SMILES: N#CCC(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and 2-cyanoacetic acid (2 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-13 (6 mg, yield: 44%). LC-MS m/z=575.2 [M++1]+.

Compound A-9 (15 mg, 0.024 mmol), HATU (9.12 mg, 0.024 mmol), DIEA (16 mg, 0.12 mmol) and 2-cyanopropionic acid (2.4 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-14 (5 mg, yield: 36%). LC-MS m/z=589.3 [M+1]+.

A-10-15: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)-4-cyanotetrahydro-2H-pyran-4-carboxamide

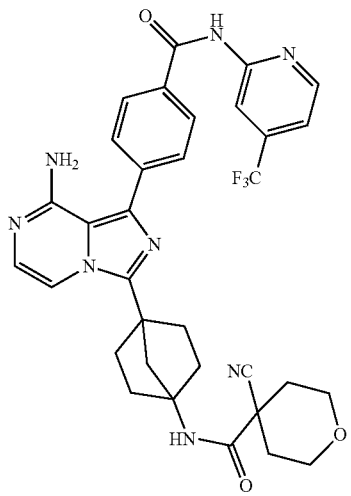 [SMILES: N#CC1(C(=O)NC23CCC(c4nc(-c5ccc(C(=O)Nc6cc(C(F)(F)F)ccn6)cc5)c5c(N)nccn45)(CC2)C3)CCOCC1]

Compound A-9 (15 mg, 0.024 mmol), HATU (9.12 mg, 0.024 mmol), DIEA (16 mg, 0.12 mmol) and 4-cyanotetrahydro-2H-pyran-4-carboxylic acid (3.7 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-15 (6 mg, yield: 39%). LC-MS m/z=645.0 [M+1]+.

A-10-16: 1-((4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)carbamoyl)cyclopropane-1-carboxylic acid

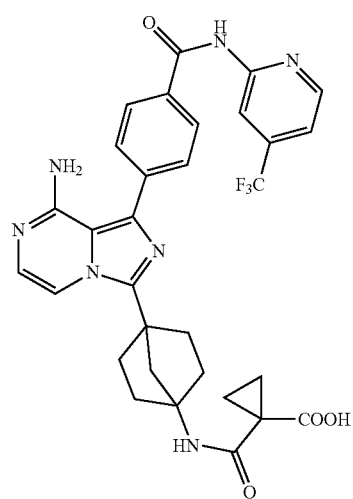 [SMILES: Nc1nccn2c(C34CCC(NC(=O)C5(C(=O)O)CC5)(CC3)C4)nc(-c3ccc(C(=O)Nc4cc(C(F)(F)F)ccn4)cc3)c12]

A solution of compound A-9 (15 mg, 0.024 mmol). HATU (9.12 mg, 0.024 mmol), DIEA (16 mg, 0.12 mmol) and cyclopropane-1,1-dicarboxylic acid (3 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-16 (6 mg, yield: 40%). LC-MS m/z=555.3 [M+1]+.

A-10-17: 4-(8-amino-3-(4-benzamidobicyclo[2.2.1]heptan-1-yl)imidazo[1,5-a]pyrazin-1-yl)-N-(4-(trifluoromethyl)pyridin-2-yl)benzamide

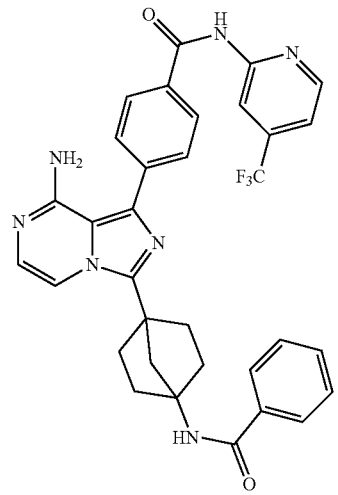 [SMILES: Nc1nccn2c(C34CCC(NC(=O)c5ccccc5)(CC3)C4)nc(-c3ccc(C(=O)Nc4cc(C(F)(F)F)ccn4)cc3)c12]

Compound A-9 (15 mg, 0.024 mmol), HATU (9.12 mg, 0.024 mmol), DIEA (16 mg, 0.12 mmol) and benzoic acid (3 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-10-17 (8 mg, yield: 53%). LC-MS m/z=612.2 [M+1]+.

A-10-18: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)picolinamide

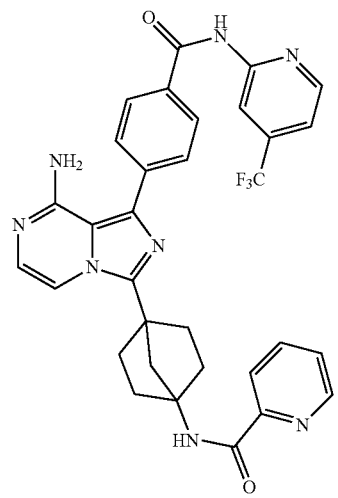 [SMILES: Nc1nccn2c(C34CCC(NC(=O)c5ccccn5)(CC3)C4)nc(-c3ccc(C(=O)Nc4cc(C(F)(F)F)ccn4)cc3)c12]

Compound A-9 (15 mg, 0.024 mmol), HATU (9.12 mg, 0.024 mmol), DIEA (16 mg, 0.12 mmol) and 2-picolinic acid (3 mg, 0.024 mmol) were stirred at room temperature for 1 h, and then the mixture was poured into water (1 mL)

and extracted with ethyl acetate (5 mL×2). The organic phase was washed with saturated aqueous NaCl solution, separated, dried over anhydrous Na₂SO₄, filtered and evaporated to dryness. The residue was purified by column chromatography (DCM/MeOH=20:1) to give the product A-10-18 (9 mg, yield: 60%). LC-MS m/z=613.2 [M+1]+.

A-10-19: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)nicotinamide

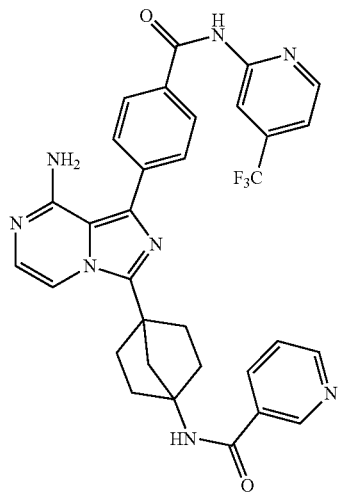 [SMILES: Nc1nccn2c(C34CCC(NC(=O)c5cccnc5)(CC3)C4)nc(-c3ccc(C(=O)Nc4cc(C(F)(F)F)ccn4)cc3)c12]

Compound A-9 (15 mg, 0.024 mmol). HATU (9.12 mg, 0.024 mmol), DIEA (16 mg, 0.12 mmol) and nicotinic acid (3 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na₂SO₄, filtered and evaporated to dryness. The residue was purified by column chromatography (DCM/MeOH=20:1) to give the product A-10-19 (8 mg, yield: 54%). LC-MS m/z=613.2 [M+1]+.

A-10-20: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)-2-methoxybenzamide

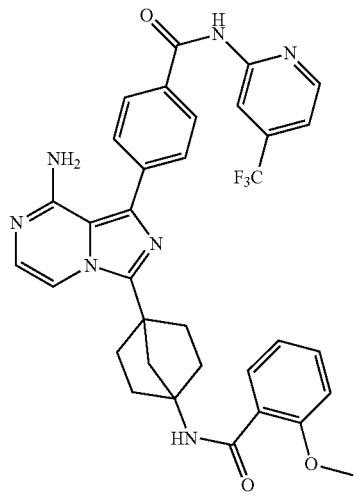 [SMILES: COc1ccccc1C(=O)NC12CCC(c3nc(-c4ccc(C(=O)Nc5cc(C(F)(F)F)ccn5)cc4)c4c(N)nccn34)(CC1)C2]

Compound A-9 (15 mg, 0.024 mmol), HATU (9.12 mg, 0.024 mmol), DIEA (16 mg, 0.12 mmol) and 2-methoxybenzoic acid (3.6 mg, 0.024 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na₂SO₄, filtered and evaporated to dryness. The residue was purified by column chromatography (DCM/MeOH=20:1) to give the product A-10-20 (8 mg, yield: 52%). LC-MS m/z=642.3 [M+1]+.

A-10-21: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)furan-2-carboxamide

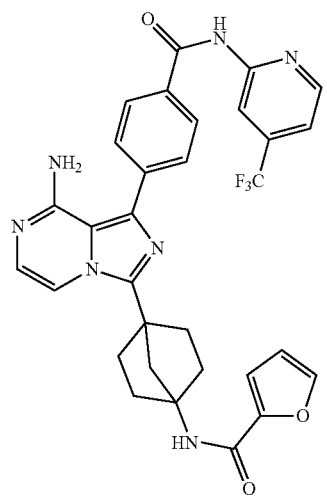

A solution of compound A-9 (15 mg, 0.024 mmol), HATU (9.12 mg, 0.024 mmol), DIEA (16 mg, 0.12 mmol) and furan-2-carboxylic acid (2.7 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous Na₂SO₄, filtered and evaporated to dryness. The residue was purified by column chromatography (DCM/MeOH=20:1) to give product A-10-21 (6 mg, yield: 43%). LC-MS m/z=602.2[M+1]⁺.

A-10-22: N-(4-(8-amino-1-(4-((4-(trifluoromethyl)pyridin-2-yl)carbamoyl)phenyl)imidazo[1,5-a]pyrazin-3-yl)bicyclo[2.2.1]heptan-1-yl)thiazole-2-carboxamide

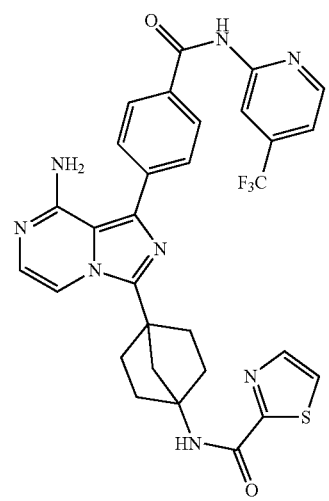 [SMILES: Nc1nccn2c(C34CCC(NC(=O)c5nccs5)(CC3)C4)nc(-c3ccc(C(=O)Nc4cc(C(F)(F)F)ccn4)cc3)c12]

A solution of compound A-9 (15 mg, 0.024 mmol), HATU (9.12 Mg, 0.024 mmol), DIEA (16 mg, 0.12 mmol) and thiazole-2-carboxylic acid (3 mg, 0.024 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-10-22 (6 mg, yield: 40%). LC-MS m/z=619.21 [M+1]+.

Synthetic Route of Compound A-13-n

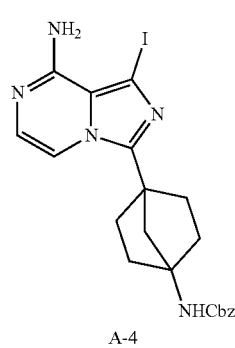

A-4

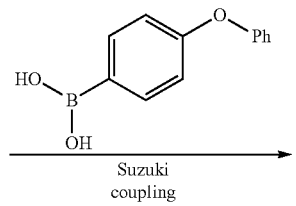

Suzuki coupling

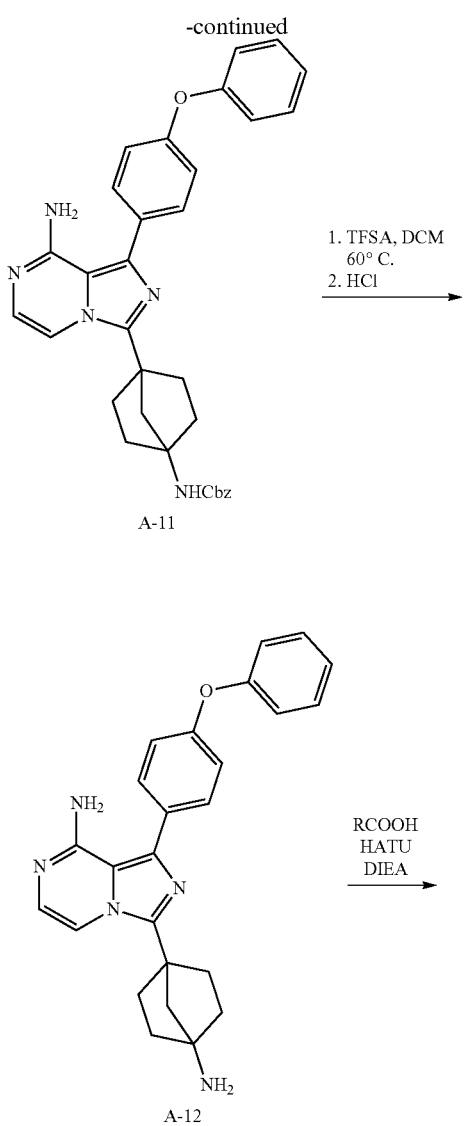

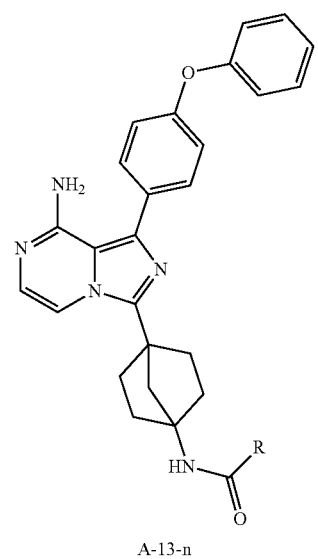

A-13-n

A-11: benzyl (4-(8-amino-1-(4-phenoxyphenyl)imi-dazol[1,5-a]pyrazin-3-yl)bicyclo[2.2.1]heptan-1-yl)carbamate

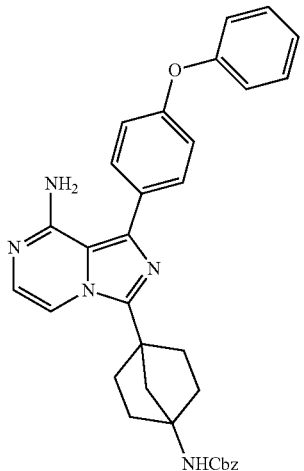 [SMILES: Nc1nccn2c(C34CCC(NC(=O)OCc5ccccc5)(CC3)C4)nc(-c3ccc(Oc4ccccc4)cc3)c12]

A solution of benzyl (4-(8-amino-1-iodoimidazo[1,5-a]pyrazin-3-yl)bicyclo[2.2.1]heptan-1-yl)carbamate (A-4) (30) mg, 0.6 mmol), 4-phenoxybenzoic acid (158 mg, 0.738 mmol), Pd[PPh$_3$]$_4$ (69 mg, 0.06 mmol) and Cs$_2$O$_3$ (239 mg, 0.738 mmol) in a mixed solvent of DME:H$_2$O (2.5 mL:0.5 mL) was heated to 80° C. and stirred overnight. The mixture was then concentrated, and the residue was purified by column chromatography to give the desired compound A-11 (268 mg, yield: 82%).

A-12: 3-(4-aminobicyclo[2.2.1]heptan-1-yl)-1-(4-phenoxyphenyl)imidazo[1,5-a]pyrazin-8-amine

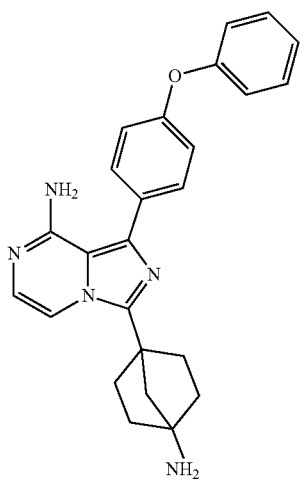 [SMILES: Nc1nccn2c(C34CCC(N)(CC3)C4)nc(-c3ccc(Oc4ccccc4)cc3)c12]

A solution of compound A-11 (260 mg, 0.48 mmol) in a mixed solvent of DCM/TFA (10 mL:10 mL) was heated to 60° C. and stirred for 18 h. After the mixture was evaporated to dryness, DCM (20 mL×2) was added, and the resulting mixture was concentrated. The residue was dissolved in DCM (30 mL), and then the solution was added to a solution of HCl in dioxane. After the mixture was evaporated to dryness, DCM (20 mL×2) was then added, and the resulting mixture was concentrated, followed by the addition of isopropyl ether (30 mL). After being stirred for 2 h, the mixture was filtered and washed with isopropyl ether (10 mL×2) to give the hydrochloride of the desired product A-12 (200 mg), which was directly used in the next step without purification.

A-13-1: N-(4-(8-amino-1-(4-phenoxyphenyl)imi-dazo[1,5-a]pyrazin-3-yl)bicyclo[2.2.1]heptan-1-yl)-2-hydroxy-2-methylpropanamide

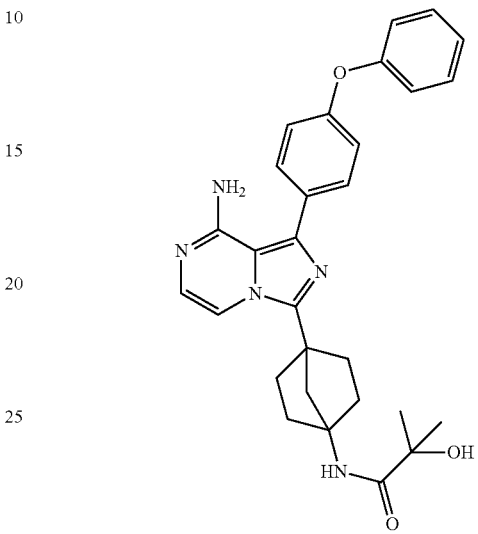

Compound A-12 (15 mg, 0.025 mmol), HATU (9.3 mg, 0.025 mmol), DIEA (19 mg, 0.15 mmol) and 2-hydroxy-2-propionic acid (3 mg, 0.029 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product A-13-1 (8 mg, yield: 57%). LC-MS m/z=498.4 [M+1]+.

A-13-2: N-(4-(8-amino-1-(4-phenoxyphenyl)imi-dazo[1,5-a]pyrazin-3-yl)bicyclo[2.2.1]heptan-1-yl)-3-methoxypropanamide

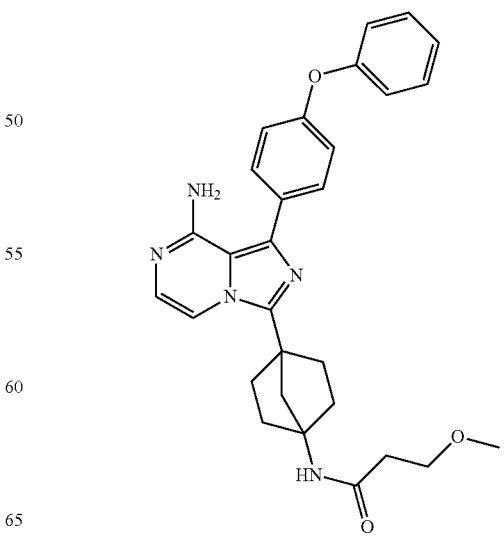

Compound A-12 (15 mg, 0.025 mmol), HATU (9.3 mg, 0.025 mmol), DIEA (19 mg, 0.15 mmol) and 3-methoxypropionic acid (3 mg, 0.029 mmol) were stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-13-2 (6 mg, yield: 40%). LC-MS m/z=498.7 [M+1]+.

A-13-3: N-(4-(8-amino-1-(4-phenoxy phenyl)imidazo[1,5-a]pyrazin-3-yl)bicyclo[2.2.1]heptan-1-yl)-3-methyloxetane-3-carboxamide

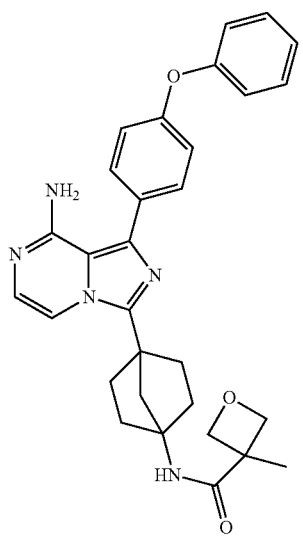 [SMILES: CC1(C(=O)NC23CCC(c4nc(-c5ccc(Oc6ccccc6)cc5)c5c(N)nccn45)(CC2)C3)COC1]

A solution of compound A-12 (15 mg, 0.025 mmol), HATU (9.3 mg, 0.025 mmol), DIEA (19 mg, 0.15 mmol) and 3-methyloxetane-3-carboxylic acid (3.4 mg, 0.029 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-13-3 (8 mg, yield: 53%). LC-MS m/z=510.2 [M+1]+.

A-13-4: N-(4-(8-amino-1-(4-phenoxyphenyl)imidazo[1,5-a]pyrazin-3-yl)bicyclo[2.2.1]heptan-1-yl)-2-morpholinoacetamide

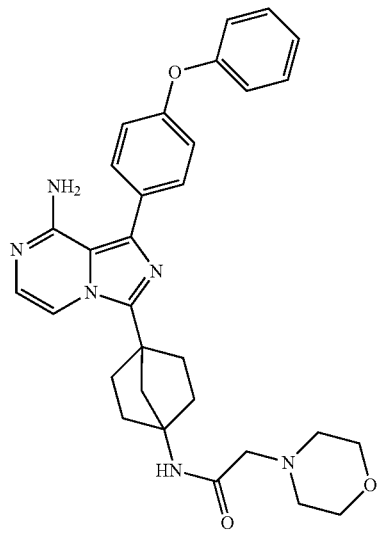 [SMILES: Nc1nccn2c(C34CCC(NC(=O)CN5CCOCC5)(CC3)C4)nc(-c3ccc(Oc4ccccc4)cc3)c12]

A solution of compound A-12 (15 mg, 0.025 mmol), HATU (9.3 mg, 0.025 mmol), DIEA (19 mg, 0.15 mmol) and 2-morpholinoacetic acid (4.2 mg, 0.029 mmol) in DMF (1 mL) was stirred at room temperature for 1 h, and then the mixture was poured into water (1 mL) and extracted with ethyl acetate (5 mL×2). The organic phase was wished with saturated aqueous NaCl solution, separated, dried over anhydrous $Na_2SO_4$, filtered and evaporated to dryness. The residue was purified by column chromatography (DCM/MeOH=20:1) to give the product A-13-4 (9 mg, yield: 58%).

Synthetic Route of Compound A-16-n

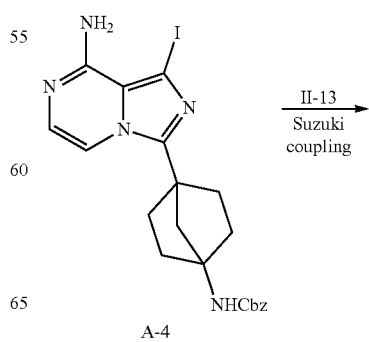

-continued

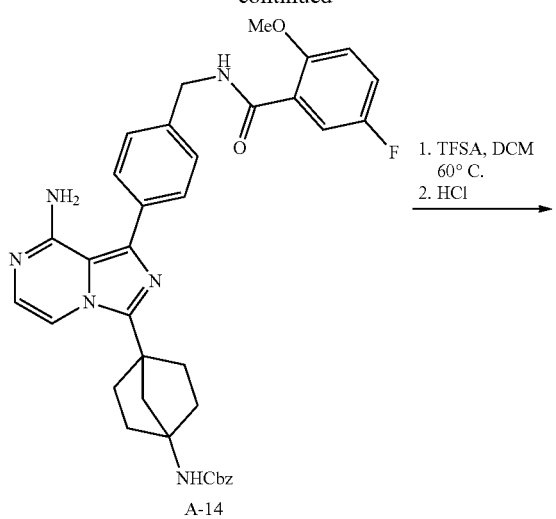

A-14

1. TFSA, DCM 60° C.
2. HCl

→

A-14: benzyl (4-(8-amino-1-(4-((5-fluoro-2-methoxybenzamido)methyl)phenyl)imidazo[1,5-a]pyrazin-3-yl)bicyclo[2.2.1]heptan-1-yl)carbamate

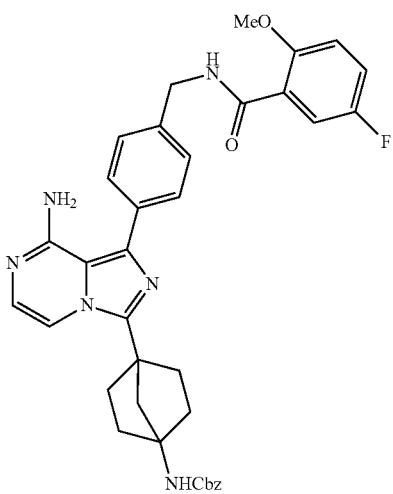 [SMILES: COc1ccc(F)cc1C(=O)NCc1ccc(-c2nc(C34CCC(NC(=O)OCc5ccccc5)(CC3)C4)n3ccnc(N)c23)cc1]

A solution of benzyl (4-(8-amino-1-iodoimidazo[1,5-a]pyrazin-3-yl)bicyclo[2.2.1]heptan-1-yl)carbamate (A-4) (300 mg, 0.6 mmol), 5-fluoro-2-methoxy-N-(4-(4,4,5,5-tetramethyl-1,3,2-dioxaborolan-2-yl)benzyl)benzamide (II-12) (284 mg, 0.738 mmol), Pd[PPh$_3$]$_4$ (69 mg, 0.06 mmol) and Cs$_2$O$_3$ (239 mg, 0.738 mmol) in a mixed solvent of DME:H$_2$O (2.5 mL:0.5 mL) was heated to 80° C. and stirred overnight. The mixture was then concentrated, and the residue was purified by column chromatography to give the desired compound A-14 (285 mg, yield: 75%).

A-15: N-(4-(8-amino-3-(4-aminobicyclo[2.2.1]heptan-1-yl)imidazo[1,5-a]pyrazin-1-yl) benzyl)-5-fluoro-2-methoxybenzamide

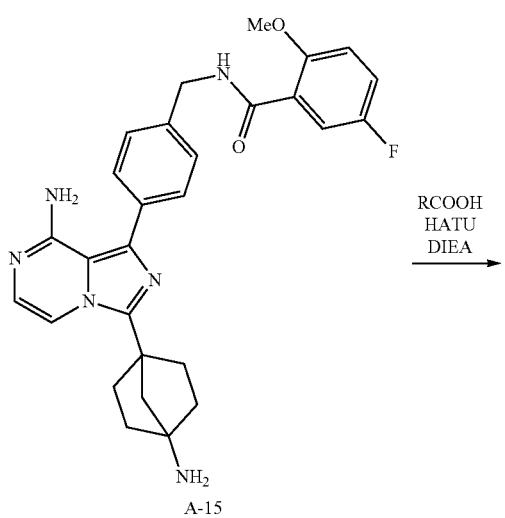

A-15

RCOOH
HATU
DIEA

→

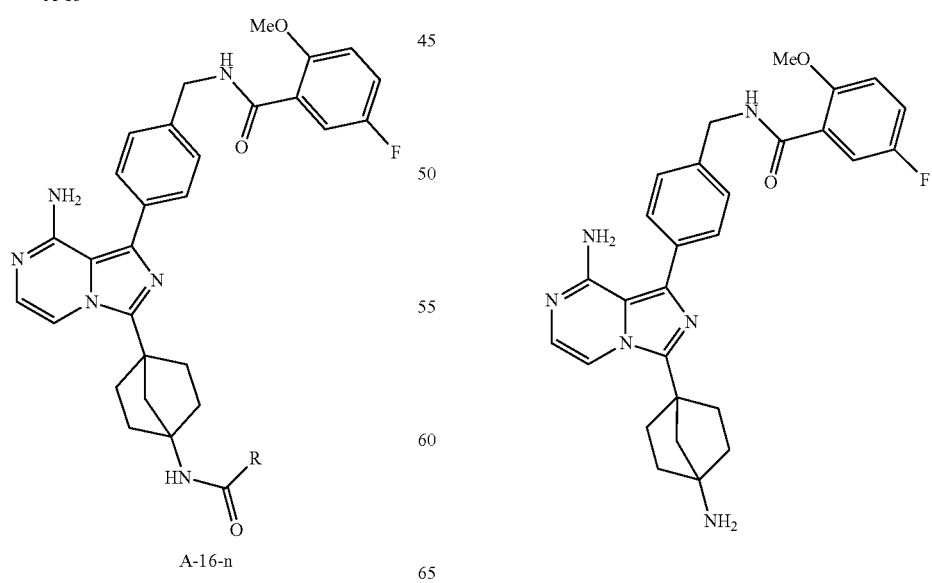

A-16-n

A solution of compound A-14 (280 mg, 0.44 mmol) in a mixed solvent of DCM/TFA (10 mL:10 mL) was heated to 60° C. and stirred for 18 h. After the mixture was evaporated to dryness, DCM (20 mL×2) was added, and the resulting mixture was concentrated. The residue was dissolved in DCM (30 mL), and then the solution was added to a solution of HCl in dioxane (10 mL). After the mixture was evaporated to dryness, DCM (20 mL×2) was then added, and the resulting mixture was concentrated, followed by the addition of isopropyl ether (30 mL). After being stirred for 2 h, the mixture was filtered and washed with isopropyl ether (10 mL×2) to give the hydrochloride of the desired product A-15 (180 mg), which was directly used in the next step without purification.

A-16-1: N-(4-(8-amino-3-(4-(2-hydroxy-2-methyl-propanamido)bicyclo[2.2.1]heptan-1-yl)imidazo[1,5-a]pyrazin-1-yl)benzyl)-5-fluoro-2-methoxybenzamide

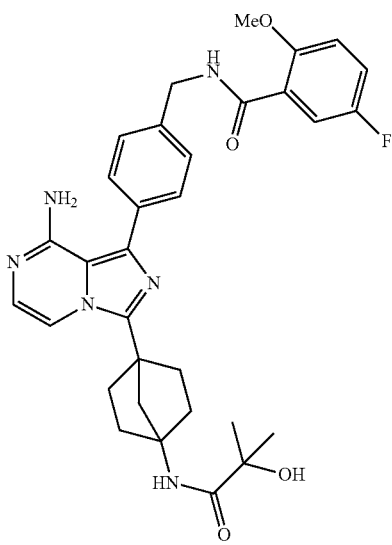 [SMILES: COc1ccc(F)cc1C(=O)NCc1ccc(-c2nc(C34CCC(NC(=O)C(C)(C)O)(CC3)C4)n3ccnc(N)c23)cc1]

A solution of compound A-15 (15 mg, 0.025 mmol), HATU (9.3 mg, 0.025 mmol), DIEA (19 mg, 0.15 mmol) and 2-hydroxy-2-propionic acid (2.6 mg, 0.025 mmol) in DMF (1 ml) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-16-1 (6 mg, yield: 40%). LC-MS m/z=587.3 [M+1]+.

A-16-2: N-(4-(8-amino-3-(4-(3-methoxypropanamido)bicyclo[2.2.1]heptan-1-yl)imidazo[1,5-a]pyrazin-1-yl)benzyl)-5-fluoro-2-methoxybenzamide

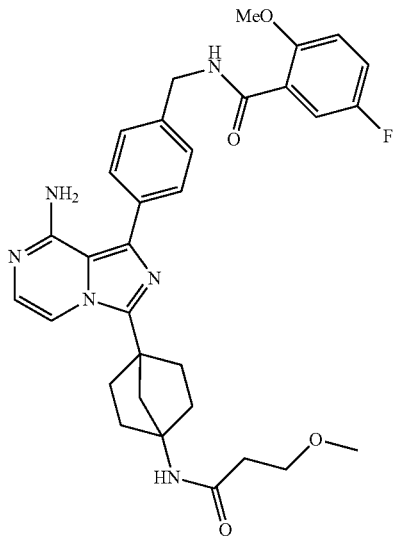 [SMILES: COCCC(=O)NC12CCC(c3nc(-c4ccc(CNC(=O)c5cc(F)ccc5OC)cc4)c4c(N)nccn34)(CC1)C2]

A solution of compound A-15 (15 mg, 0.025 mmol), HATU (9.3 mg, 0.025 mmol), DIEA (19 mg, 0.15 mmol) and 3-methoxypropionic acid (2.6 mg, 0.025 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $NaSO_4$, filtered and evaporated to dryness. The residue was purified by column chromatography (DCM/MeOH=20:1) to give the product A-16-2 (8 mg, yield: 40%). LC-MS m/z=587.3 [M+1]+.

A-16-3: N-(4-(8-amino-1-(4-((5-fluoro-2-methoxybenzamido)methyl)phenyl)imidazo[1,5-a]pyrazin-3-yl)bicyclo[2.2.1]heptan-1-yl)-3-methyloxetane-3-carboxamide

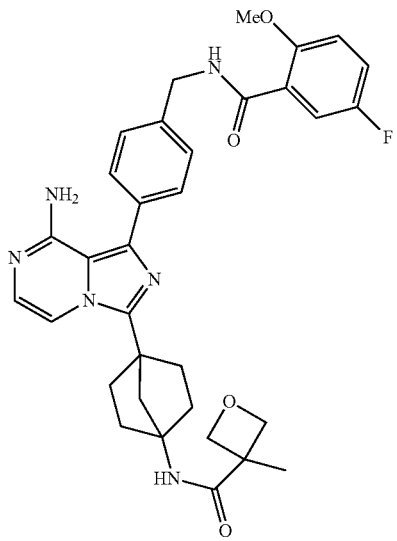 [SMILES: COc1ccc(F)cc1C(=O)NCc1ccc(-c2nc(C34CCC(NC(=O)C5(C)COC5)(CC3)C4)n3ccnc(N)c23)cc1]

A solution of compound A-15 (15 mg, 0.025 mmol), HATU (9.3 mg, 0.025 mmol), DIEA (19 mg, 0.15 mmol) and 3-methyloxetane-3-carboxylic acid (2.9 mg, 0.025 mmol) in DMF (1 mL) was stirred at room temperature for 1 h, and then the mixture was poured into water (5 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-16-3 (10 mg, yield: 66%). LC-MS m/z=599.3 [M+1]+.

A-16-4: N-(4-(8-amino-3-(4-(2-morpholinoacetamido)bicyclo[2.2.1]heptan-1-yl)imidazo[1,5-a]pyrazin-1-yl) benzyl)-5-fluoro-2-methoxybenzamide

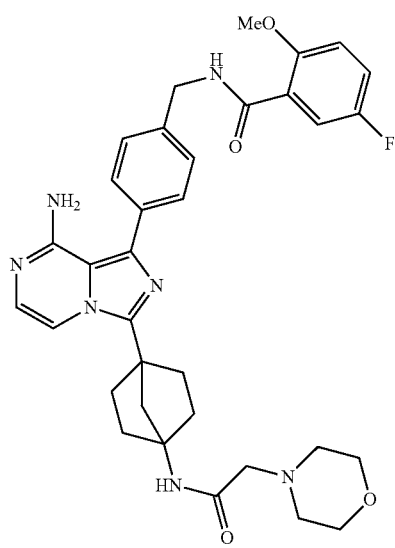 [SMILES: COc1ccc(F)cc1C(=O)NCc1ccc(-c2nc(C34CCC(NC(=O)CN5CCOCC5)(CC3)C4)n3ccnc(N)c23)cc1]

A solution of compound A-15 (15 mg, 0.025 mmol), HATU (9.3 mg, 0.025 mmol), DIEA (19 mg, 0.15 mmol) and 2-morpholinoacetic acid (3.6 mg, 0.025 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product A-16-4 (9 mg, yield: 57%). LC-MS m/z=628.3 [M+1]+.

Synthetic Route of Compound B-6-n

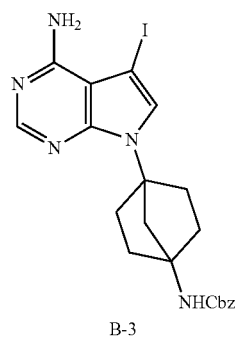

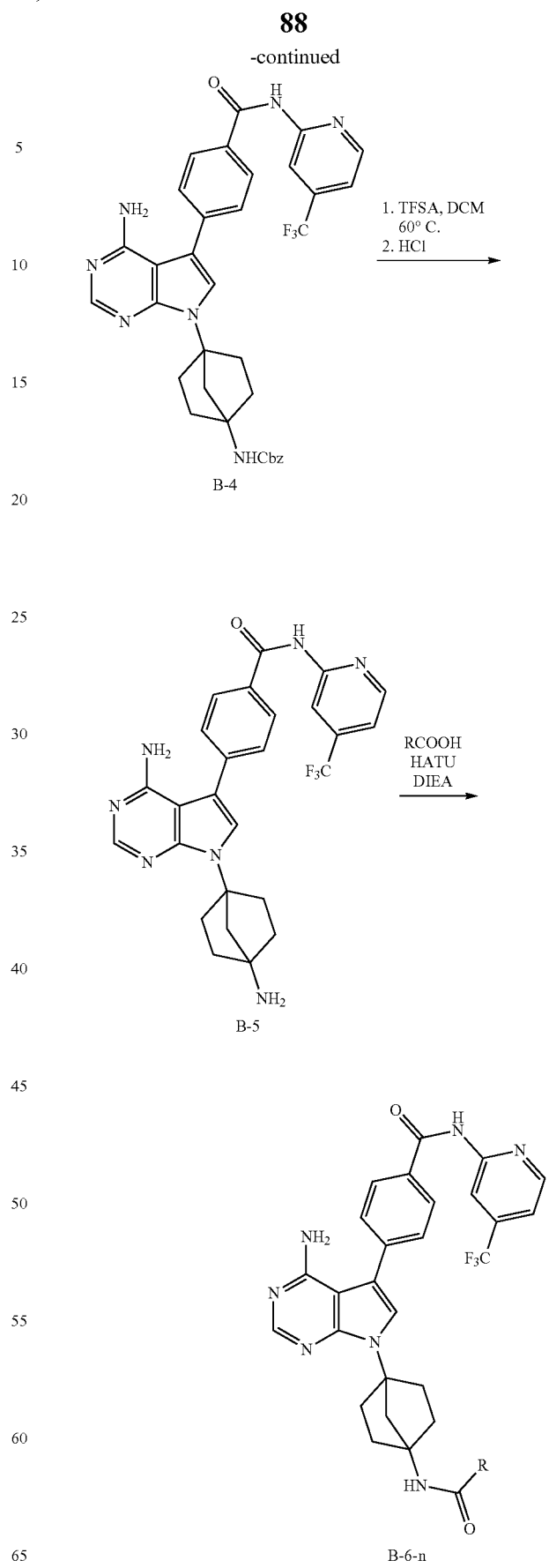

B-4: benzyl (4-(4-amino-5-(4-((4-(trifluoromethyl)pyridin-2-yl)carbamoyl)phenyl)-7H-pyrrolo[2,3-d]pyrimidin-7-yl)bicyclo[2.2.1]heptan-1-yl)carbamate

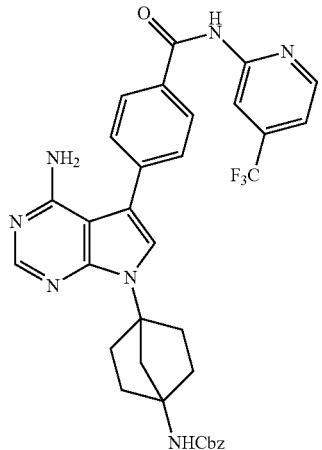 [SMILES: Nc1ncnc2c1c(-c1ccc(C(=O)Nc3cc(C(F)(F)F)ccn3)cc1)cn2C12CCC(NC(=O)OCc3ccccc3)(CC1)C2]

A solution of compound B-3 (200 mg, 0.4 mmol), (4-((4-(trifluoromethyl)pyridin-2-yl) carbamoyl)phenyl)boronic acid (II-3)(152 mg, 0.49 mmol), Pd[PPh$_3$]$_4$ (46 mg, 0.04 mmol) and Cs$_2$CO$_3$ (159 mg, 0.49 mmol) in a mixed solvent of DME:H$_2$O (2.5 mL:0.5 mL) was heated to 80° C. and stirred overnight. The mixture was concentrated, and the residue was purified by column chromatography (methanol/DCM=1:40) to give the desired compound B-4 (187 mg, yield: 73%).

B-5: 4-(4-amino-7-(4-aminobicyclo[2.2.1]heptan-1-yl)-711-pyrrolo[2,3-d]pyrimidin-5-yl)-N-(4-(trifluoromethyl)pyridin-2-yl)benzamide

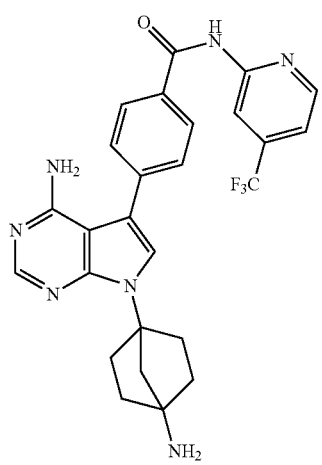 [SMILES: Nc1ncnc2c1c(-c1ccc(C(=O)Nc3cc(C(F)(F)F)ccn3)cc1)cn2C12CCC(N)(CC1)C2]

A solution of compound B-4 (187 mg, 0.29 mmol) in a mixed solvent of DCM/TFA (10 mL:10 mL) was heated to 60° C. and stirred for 18 h. After the mixture was evaporated to dryness, DCM (20 mL×2) was added, and the resulting mixture was concentrated. The residue was added with DCM (30 mL), and then the mixture was added to a solution of HCl in dioxane (10 mL). After the mixture was evaporated to dryness, DCM (20 mL×2) was then added again, and the resulting mixture was evaporated to dryness, followed by the addition of isopropyl ether (30 mL). After being stirred for 2 h, the mixture was filtered and washed with isopropyl ether (10 mL×2) to give the hydrochloride of the desired product B-5, which was directly used in the next step without purification.

B-6-1: 4-(4-amino-7-(4-(but-2-ynamido)bicyclo[2.2.1]heptan-1-yl)-7H-pyrrolo[2,3-d]pyrimidin-5-yl)-N-(4-trifluoromethyl)pyridin-2-yl)benzamide

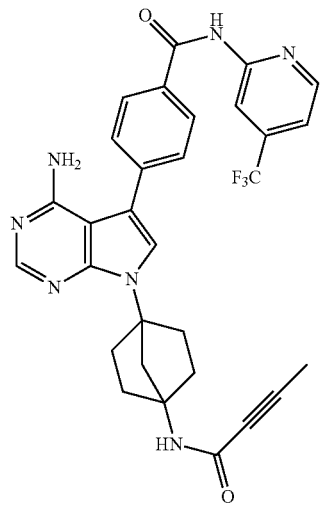 [SMILES: CC#CC(=O)NC12CCC(n3cc(-c4ccc(C(=O)Nc5cc(C(F)(F)F)ccn5)cc4)c4c(N)ncnc43)(CC1)C2]

A solution of compound B-5 (19 mg, 0.031 mmol), HATU (12 mg, 0.031 mmol), DIEA (24 mg, 0.19 mmol) and but-2-ynoic acid (2.6 mg, 0.031 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous Na$_2$SO$_4$, filtered and evaporated to dryness. The residue was purified by column chromatography (DCM/MeOH=20:1) to give the product B-6-1 (11 mg yield: 59%). LC-MS m/z=574.3 [M+1]+.

B-6-2: 4-(4-amino-7-(4-(2-hydroxy-2-methylpropanamido)bicyclo[2.2.1]heptan-1-yl)-7f-pyrrolo[2,3-d]pyrimidin-5-yl)-N-(4-(trifluoromethyl)pyridin-2-yl)benzamide

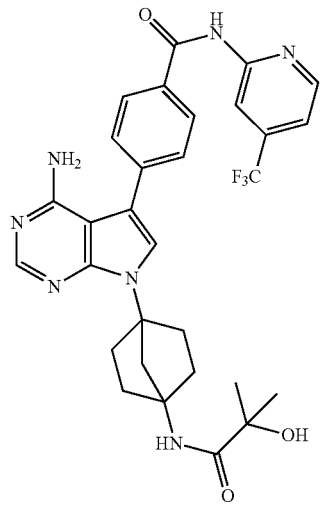 [SMILES: CC(C)(O)C(=O)NC12CCC(n3cc(-c4ccc(C(=O)Nc5cc(C(F)(F)F)ccn5)cc4)c4c(N)ncnc43)(CC1)C2]

A solution of compound B-5 (19 mg, 0.031 mmol), HATU (12 mg, 0.031 mmol), DIEA (24 mg, 0.19 mmol) and 2-hydroxy-2-methylpropionic acid (3.2 mg, 0.031 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product B-6-2 (9 mg, yield: 49%). LC-MS m/z=594.2 [M+1]+.

B-6-3: 4-(4-amino-7-(4-(3-methoxypropanamido)bicyclo[2.2.1]heptan-1-yl)-7H-pyrrolo[2,3-d]pyrimidin-5-yl)-N-(4-(trifluoromethyl)pyridin-2-yl)benzamide

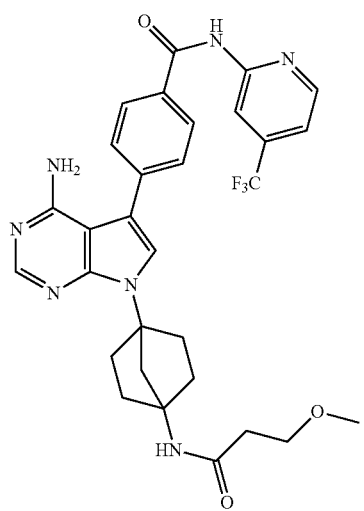 [SMILES: COCCC(=O)NC12CCC(n3cc(-c4ccc(C(=O)Nc5cc(C(F)(F)F)ccn5)cc4)c4c(N)ncnc43)(CC1)C2]

A solution of compound B-5 (19 mg, 0.031 mmol), HATU (12 mg, 0.031 mmol), DIEA (24 mg, 0.19 mmol) and 3-methoxypropionic acid (3.2 mg, 0.031 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product B-6-3 (12 mg, yield: 66%). LC-MS m/z=594.2 [M+1]+.

B-6-4: N-(4-(4-amino-5-(4-((4-(trifluoromethyl)pyridin-2-yl)carbamoyl)phenyl)-7H-pyrrolo[2,3-d]pyrimidin-7-yl)bicyclo[2.2.1]heptan-1-yl)-3-methyloxetane-3-carboxamide

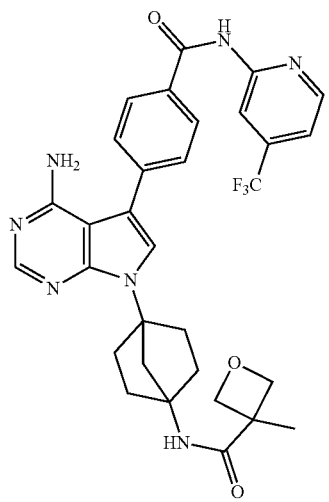 [SMILES: CC1(C(=O)NC23CCC(n4cc(-c5ccc(C(=O)Nc6cc(C(F)(F)F)ccn6)cc5)c5c(N)ncnc54)(CC2)C3)COC1]

A solution of compound B-5 (19 mg, 0.031 mmol), HATU (12 Mg, 0.031 mmol), DIEA (24 mg, 0.19 mmol) and 3-methyloxetane-3-carboxylic acid (3.6 mg, 0.031 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product B-6-4 (12 mg, yield: 64%). LC-MS m/z=606.3 [M+1]+.

B-6-5: 4-(4-amino-7-(4-(2-morpholinoacetamido)bicyclo[2.2.1]heptan-1-yl)-7H-pyrrolo[2,3-d]pyrimidin-5-yl)-N-(4-(trifluoromethyl)pyridin-2-yl)benzamide

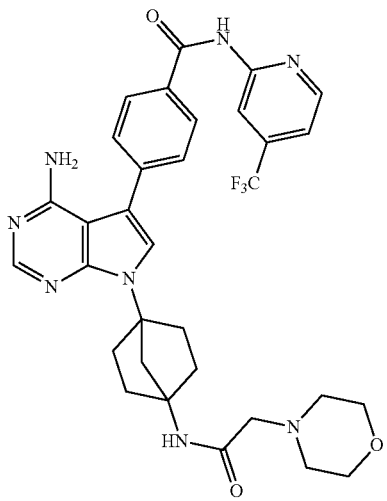 [SMILES: Nc1ncnc2c1c(-c1ccc(C(=O)Nc3cc(C(F)(F)F)ccn3)cc1)cn2C12CCC(NC(=O)CN3CCOCC3)(CC1)C2]

A solution of compound B-5 (19 mg, 0.031 mmol), HATU (12 mg, 0.031 mmol), DIEA (24 mg, 0.19 mmol) and 2-morpholinoacetic acid (4.5 mg, 0.031 mmol) in DMF (1 mL) was stirred at room temperature for 1 h, and then the mixture was poured into water (l mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product B-6-5 (11 mg, yield: 58%). LC-MS m/z=635.2 [M+1]+.

Synthetic Route of Compound C-7-n

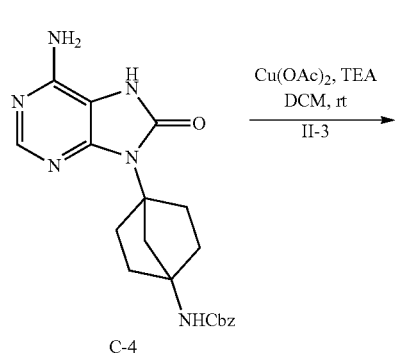

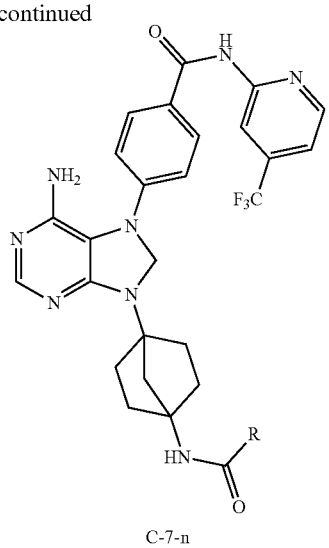

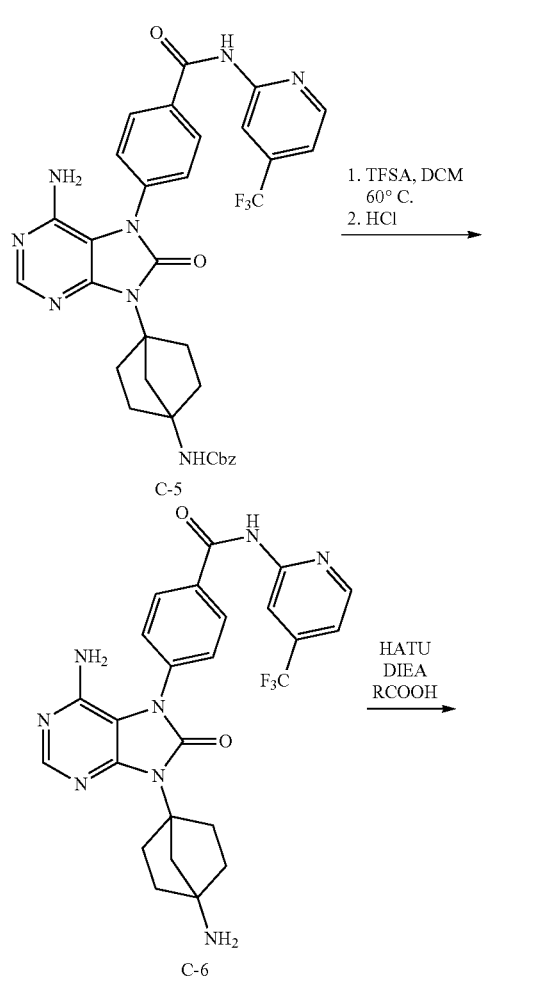

C-5: benzyl (4-(6-amino-8-oxo-7-(4-((4-(trifluoromethyl)pyridin-2-yl)carbamoyl)phenyl)-7,8-dihydro-9H-purin-9-yl)bicyclo[2.2.1]heptan-1-yl)carbamate A solution of compound C-4 (100 mg, 0.25 mmol). (4-((4-(trifluoromethyl)pyridin-2-yl) carbamoyl)phenyl)boronic acid (II-3) (160 mg, 0.5 mmol), copper acetate (64) mg, 0.3 mmol) and $Et_3N$ (30 mg, 0.3 mmol) in DCM (10 mL) was stirred at room temperature for 24 h, and then the mixture was poured into water (20 mL) and extracted with ethyl acetate (10 mL×2). The organic phase was separated, dried over anhydrous $Na_2SO_4$, filtered and evaporated to dryness. The residue was purified by column chromatography (EA/PE=1:1 EA) to give the desired compound C-5 (47 mg, yield: 29%). LC-MS m/z=657.3 [M−1]−.

C-6: 4-(6-amino-9-(4-aminobicyclo[2.2.1]heptan-1-yl)-8-oxo-8,9-dihydro-7H-purin-7-yl)-N-(4-(trifluoromethyl)pyridin-2-yl)benzamide

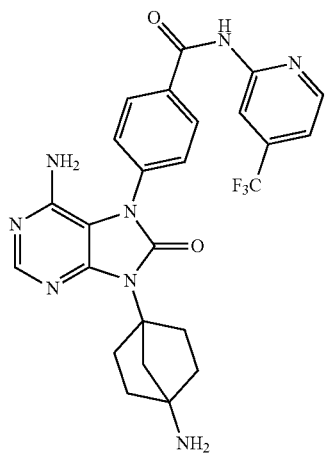 [SMILES: Nc1ncnc2c1n(-c1ccc(C(=O)Nc3cc(C(F)(F)F)ccn3)cc1)c(=O)n2C12CCC(N)(CC1)C2]

A solution of compound C-5 (45 mg, 0.09 mmol) in a mixed solvent of DCM/TFA (10 mL:10 mL) was heated to 60° C. and stirred for 18 h. After the mixture was evaporated to dryness, DCM (20 mL×2) was added, and the resulting mixture was concentrated. The residue was dissolved in DCM (30 mL), and then the solution was added to a solution of HCl in dioxane (10 mL). After the mixture was evaporated to dryness, DCM (20 mL×2) was then added, and the resulting mixture was concentrated, followed by the addition of isopropyl ether (30 mL). After being stirred for 2 h, the mixture was filtered and washed with isopropyl ether (10 mL×2) to give the hydrochloride of the desired product C-6, which was directly used in the next step without purification.

C-7-1: 4-(6-amino-9-(4-(but-2-ynamido)bicyclo[2.2.1]heptan-1-yl)-8-oxo-8,9-dihydro-7H-purin-7-yl)-N-(4-(trifluoromethyl)pyridin-2-yl)benzamide

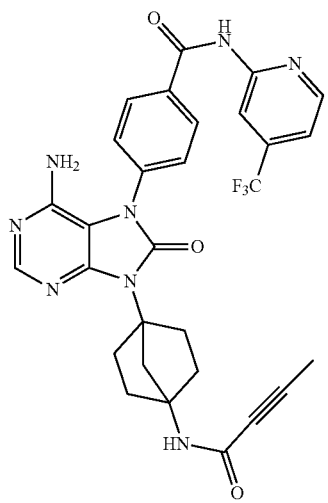 [SMILES: CC#CC(=O)NC12CCC(n3c(=O)n(-c4ccc(C(=O)Nc5cc(C(F)(F)F)ccn5)cc4)c4c(N)ncnc43)(CC1)C2]

A solution of compound C-6 (13 mg, 0.022 mmol), HATU (9 mg, 0.022 mmol), DIEA (16.8 mg, 0.13 mmol) and but-2-ynoic acid (1.8 mg, 0.022 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product C-7-1 (5 mg, yield: 38%). LC-MS m/z=591.2 [M+1]+.

C-7-2: 4-(6-amino-9-(4-(2-morpholinoacetamido)bicyclo[2.2.1]heptan-1-yl)-8-oxo-8,9-dihydro-7H-purin-7-yl)-N-(4-(trifluoromethyl)pyridin-2-yl)benzamide

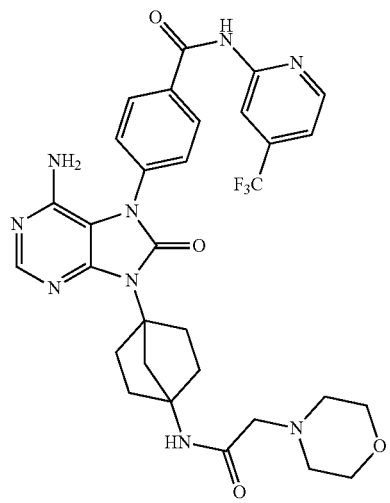 [SMILES: Nc1ncnc2c1n(-c1ccc(C(=O)Nc3cc(C(F)(F)F)ccn3)cc1)c(=O)n2C12CCC(NC(=O)CN3CCOCC3)(CC1)C2]

A solution of compound C-6 (13 mg, 0.022 mmol), HATU (9 mg, 0.022 mmol). DIEA (16.8 mg, 0.13 mmol) and 2-morpholinoacetic acid (3.2 mg, 0.022 mmol) in DMF (1 mL) was stirred at room temperature for 1 h, and then the mixture was poured into water (1 mL) and extracted with ethyl acetate (5 mL×2). The organic phase was washed with saturated aqueous NaCl solution, separated, dried over anhydrous $Na_2SO_4$, filtered and evaporated to dryness. The residue was purified by column chromatography (DCM/MeOH=20:1) to give the product C-7-2 (6 mg, yield: 42%). LC-MS m/z=652.2 [M+1]+.

Synthetic Route of Compound D-8-n

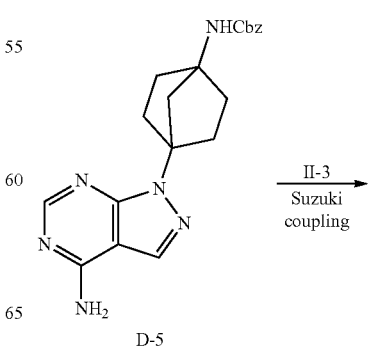

-continued

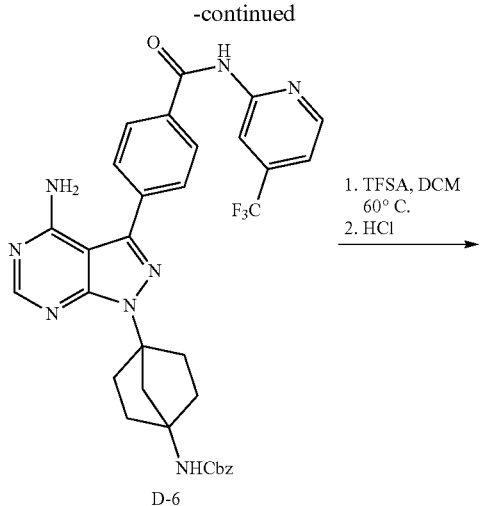

D-6

1. TFSA, DCM 60° C.
2. HCl
→

D-6: benzyl (4-(4-amino-3-(4-((4-(trifluoromethyl)pyridin-2-yl)carbamoyl)phenyl)-1H-pyrazolo[3,4-d]pyrimidin-1-yl)bicyclo[2.2.1]heptan-1-yl)carbamate

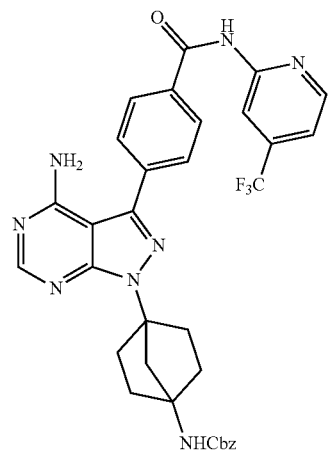 [SMILES: Nc1ncnc2c1c(-c1ccc(C(=O)Nc3cc(C(F)(F)F)ccn3)cc1)nn2C12CCC(NC(=O)OCc3ccccc3)(CC1)C2]

A mixed solution of D-5 (96 mg, 0.19 mmol), II-3 (73 mg, 0.234 mmol), Pd[PPh₃]₄ (22 mg, 0.019 mmol) and Cs₂CO₃ (76.4 mg, 0.234 mmol) in DME/H₂O (9 mL/1 ml) was purged with N₂ for 1 min to remove oxygen and then heated to 80° C. in a sealed tube and stirred for 12 h. After the mixture was cooled, the reaction was quenched with brine (20 mL) and EA (50 mL×2) was added for extraction. The organic phase was dried over anhydrous Na₂SO₄, filtered and concentrated. The residue was purified by silica gel column chromatography (eluent: PE/EA=1:1) to give the desired product D-6 (42 mg, 34.4%). LC-MS m/z=643.2 [M+1]+.

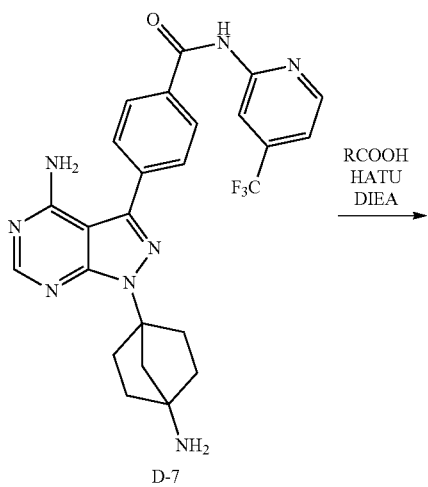

D-7

RCOOH
HATU
DIEA
→

D-7: 4-(4-amino-1-(4-aminobicyclo[2.2.1]heptan-1-yl)-1H-pyrazolo[3,4-d]pyrimidin-3-yl)-N-(4-(trifluoromethyl)pyridin-2-yl)benzamide

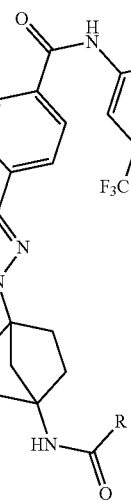

D-8-n

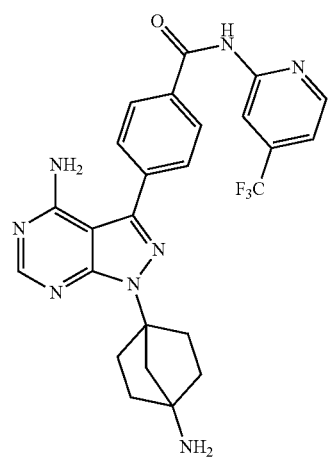 [SMILES: Nc1ncnc2c1c(-c1ccc(C(=O)Nc3cc(C(F)(F)F)ccn3)cc1)nn2C12CCC(N)(CC1)C2]

A mixture of D-6 (42 mg, 0.065 mmol) in TFA/DCM (1 mL/1 mL) was stirred at 60° C. for 12 h. After the mixture was cooled, the solvent was removed by evaporation. A solution of HCl in dioxane (2 mL) was then added, and the resulting mixture was stirred for 10 min and concentrated. The residue was added with isopropyl ether (10 mL), stirred, and concentrated. The above procedure was repeated twice. The solid was filtered, washed with isopropyl ether and dried to give the hydrochloride of the desired product D-7 (30 mg, 75%).

D-8-1: 4-(4-amino-1-(4-(but-2-ynamido)bicyclo [2.2.1]heptan-1-yl)-1H-pyrazolo[3,4-d]pyrimidin-3-yl)-N-(4-(trifluoromethyl)pyridin-2-yl)benzamide

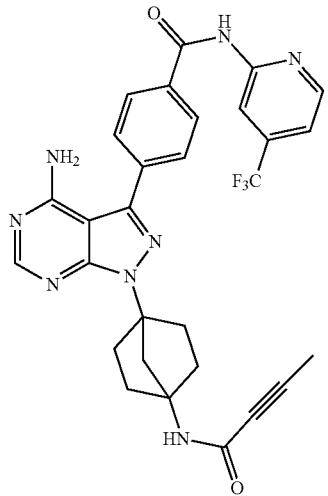 [SMILES: CC#CC(=O)NC12CCC(n3nc(-c4ccc(C(=O)Nc5cc(C(F)(F)F)ccn5)cc4)c4c(N)ncnc43)(CC1)C2]

A mixed solution of D-7 (15 mg, 0.025 mmol), but-2-ynoic acid (2 mg, 0.024 mmol), HATU (9.1 mg, 0.024 mmol) and DIEA (0.041 mL, 0.241 mmol) in DMF (1 mL) was stirred at room temperature for 4 h. The reaction solution was diluted with EA (30 mL) and washed with brine, and the organic phase was dried over anhydrous $Na_2SO_4$, filtered and concentrated. The residue was purified by silica gel column chromatography (eluent: PE/EA=1:1) to give the desired product D-8-1 (12 mg, 86%). LC-MS m/z=575.1 [M+1]+.

D8-2: 4-(4-amino-1-(4-(2-morpholinoacetamido) bicyclo[2.2.1]heptan-1-yl)-1H-pyrazolo[3,4-d]pyrimidin-3-yl)-N-(4-(trifluoromethyl)pyridin-2-yl)benzamide

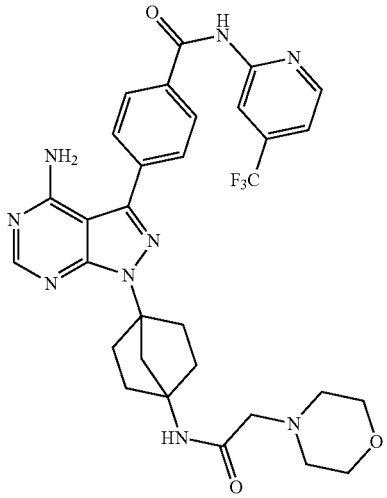 [SMILES: Nc1ncnc2c1c(-c1ccc(C(=O)Nc3cc(C(F)(F)F)ccn3)cc1)nn2C12CCC(NC(=O)CN3CCOCC3)(CC1)C2]

A mixed solution of D-7 (15 mg, 0.025 mmol), 2-morpholinoacetic acid (3.5 mg, 0.024 mmol), HATU (9.1 mg, 0.024 mmol) and DIEA (0.041 mL, 0.241 mmol) in DMF (1 mL) was stirred at room temperature for 4 h. The reaction solution was diluted with EA (30 mL) and washed with brine, and the organic phase was dried over anhydrous $Na_2SO_4$, filtered and concentrated. The residue was purified by silica gel column chromatography (eluent: PE/EA=1:1) to give the desired product D-8-2 (8.5 mg, 56%). LC-MS m/z=636.3 [M+1]+.

1. In Vitro Inhibitory Activity Against BTK(Wt)/BTK (C481S) (Determination of $IC_{50}$ Value)

(1) Method

The substrate solution was prepared by adding the substrate poly(Glu, Tyr) sodium salt (Sigma Aldrich, St. Louis, MO) to the substrate reaction buffer (20 mM Hepes (pH 7.5), 10 mM $MgCl_2$, 1 mM EGTA, 0.02% Brij35, 0.02 mg/mL BSA, 0.1 mM $Na_3VO_4$, 2 mM DIT and 1% DMSO)(final substrate concentration in the reaction solution was 0.2 μM). Test compound was formulated into stock solutions at 10 mM concentration with 100% DMSO, and 3-fold serial dilution for 10 doses was performed in a 384-well cyclic olefin copolymer LDV microplate. BTK(wt) or BTK (C481S) kinase (recombinant human full-length protein, histidine tag, expressed in insect cells, invitrogen, Carlsbad, CA) was added to the substrate solution and mixed gently (final BTK concentration in the reaction solution was 8 nM). Test compound in 100% DMSO was then added to the kinase reaction mixture by acoustic liquid transfer technology (Echo 550; nanoliter range) (Labcyte Inc, Sunny vale, CA) and incubated for 20 min at room temperature, 33P-ATP (specific activity 10 μCi/μL) was added to the reaction mixture to initiate the reaction, followed by incubation at room temperature for 2 h. A small portion of the reaction mixture was dropped onto P-81 ion exchange filter paper (Whatman). After washing the unbound phosphate from the filter paper with 0.75% phosphate buffer (three times) and drying, the remaining radioactivity on the filter paper was measured. The kinase activity was expressed as the percentage of the remaining, kinase activity in the test sample to the kinase activity in the vehicle (dimethyl sulfoxide) blank control. $IC_{50}$ values were calculated by curve fitting the data obtained using Prism (GraphPad Software).

(2) Results

Compared with the second-generation BTK inhibitor acalabrutinib, most of the compounds disclosed herein have stronger inhibition capability against the activity of wild-type BTK(wt) enzyme. More importantly, most of the compounds exhibit more excellent inhibition activity against BTK(C481S) mutants, and some even show inhibition activity of less than (0.1 nM.

TABLE 1

Inhibition against activity of BTK (wt)/BTK (C481S) enzyme
(A ≤ 0.1 nM; 0.1 nM < B ≤ 1 nM; 1 nM < C ≤ 10 nM; 10 nM < D ≤ 50 nM)

| Compound number | $IC_{50}$ BTK (wt) | $IC_{50}$ BTK (C481S) | Compound number | $IC_{50}$ BTK (wt) | $IC_{50}$ BTK (C481S) |
|---|---|---|---|---|---|
| A-7-2 | C | B | A-7-3 | B | B |
| A-7-5 | C | B | A-7-9 | C | B |
| A-7-12 | C | B | A-7-14 | C | B |
| A-10-1 | C | B | A-10-3 | C | B |
| A-10-5 | C | A | A-10-6 | C | A |
| A-10-7 | C | B | A-10-8 | C | A |
| A-10-10 | C | A | A-10-11 | C | B |

TABLE 1-continued

Inhibition against activity of BTK (wt)/BTK (C481S) enzyme
(A ≤ 0.1 nM; 0.1 nM < B ≤ 1 nM; 1 nM < C ≤ 10 nM;
10 nM < D ≤ 50 nM)

| Compound number | IC$_{50}$ BTK (wt) | IC$_{50}$ BTK (C481S) | Compound number | IC$_{50}$ BTK (wt) | IC$_{50}$ BTK (C481S) |
|---|---|---|---|---|---|
| A-10-12 | C | B | A-10-13 | C | A |
| A-10-14 | C | B | A-10-15 | C | B |
| A-10-17 | D | C | A-10-18 | D | C |
| A-10-19 | D | C | A-10-20 | D | C |
| A-10-21 | C | C | A-10-22 | C | C |
| A-13-1 | C | C | A-13-2 | C | B |
| A-13-3 | C | C | A-13-4 | D | C |
| A-16-1 | D | C | A-16-2 | C | C |
| A-16-3 | C | C | A-16-4 | C | C |
| B-6-1 | C | C | B-6-2 | D | C |
| B-6-3 | C | C | B-6-4 | C | C |
| B-6-5 | C | C | C-7-1 | C | C |
| C-7-2 | C | B | Acalabrutinib | 18.6 nM | 8.15 nM |

2. Experiment on In Vitro Tumor Cell Proliferation Inhibition (1) Method

The tumor cell line (TMD-8/OCY-LY10) was suspended in RPMI1640+FBS10% and cultured in an incubator (37° C. 5% CO$_2$). Cells were passaged periodically, and cells at logarithmic growth phase were collected for plating.

Cell staining was performed with trypan blue and viable cells were counted.

Cell concentration was adjusted to 7000 cells/well with medium.

90 µL of cell suspension was added to a 96-well plate and cell-free culture medium was added to the blank control wells.

Cells in the 96-well plate were incubated overnight in an incubator (37° C., 5% CO$_2$, 100% relative humidity).

Preparation of 400× compound storage plates: test compounds and reference drug were each dissolved in DMSO and 3× diluted from the highest concentration (400 µM) to the lowest concentration (0.61 µM).

Preparation of 10× compound working solutions: 78 µL of cell culture medium was added to a V-bottom 96-well plate, and 2 µL of the compound was pipetted from the 400× compound storage plate into the 96-well plate. Vehicle control wells and blank control wells were added with 2 µL of DMSO. After the addition of the compound or DMSO, the mixture was mixed well by a pipette.

Adding compound: 10 µL of 10× compound working solution (as shown in Table 1) was added to the cell culture plate, 10 µL of the mixture of DMSO and cell culture solution was added to the vehicle control wells and blank control wells. The final concentration of DMSO was 0.25%.

The 96-well cell plate was put back in the incubator for 72 h of culturing.

CellTiter-Glo buffer was thawed and left to stand to room temperature.

CellTiter-Glo substrate was left to stand to room temperature.

A flask of CellTiter-Glo substrate was added with the CellTiter-Glo buffer for dissolving, such that a CellTiter-Glo working solution was prepared.

The flask was subjected to slow vortex shaking to completely dissolve the substrate.

The cell culture plate was taken out and left to stand for 30 min to be balanced to room temperature.

50 µL (equal to half the volume of cell culture medium in each well) of the CellTiter-Glo working solution was added to each well. The cell plate was wrapped with aluminum foil to keep out of light.

The plate was shaken on at orbital shaker for 2 min to induce cell lysis.

The plate was left to stand at room temperature for 10 min to stabilize the luminescence signals.

The luminescence signals were detected on 2104 EnVision plate reader.

Data analysis: The inhibition rate (IR) of the test compound was calculated by the following formula: JR (%)=(1−(RLU compound RLU blank control)/(RLU vehicle control−RLU blank control))−100%. Inhibition rates of compounds at different concentrations were calculated in Excel, followed by plotting the inhibition curves and calculating IC$_{50}$ values with GraphPad Prism.

(2) Results

In the proliferation inhibition experiment of B-cell lymphoma cells TMD-8 and OCI-LY10, compound A-10-10 and ibrutinib exhibit strong inhibition activity against tumor cell proliferation.

TABLE 2

Inhibitory activity of compound A-10-10/ibrutinib against tumor cell proliferation

| Compound number | IC$_{50}$ (nM) | |
|---|---|---|
|  | TMD-8 | OCI-LY10 |
| A-10-10 | 2.9 | 10.3 |
| Ibrutinib | 0.4 | 1.7 |

3. Pharmacokinetic Study (1) Method

Male SD rats were fasted overnight before test. The test drugs were each suspended in a solution of 0.5% methylcellulose (MC) and 0.1% SDS in deionized water (w/w/v), and the suspension, each at a concentration of 1 mg/mL, was administered intragastrically at 5 mL/kg. At 15 min. 30 min. 1 h, 2 h, 4 h, 6 h, 8 h and 24 h after administration, approximately 0.4 mL of whole blood was collected from the orbital venous plexus of the animals and then placed in heparin anticoagulant tubes. Three animals were sampled at each time point and then put to death, and thus sample collection was completed on different individuals. The whole blood sample would be centrifuged within 15 min and centrifuged at 4° C./4200 rpm for 5 min. All plasma samples were stored in a refrigerator at −80±15° C. prior to analysis. An LC-MS/MS (Waters I Class UPLC-Xevo TQD tandem mass spectrometry) assay for the compounds was established prior to sample analysis. The collected plasma was quantitatively analyzed, plasma concentration-time data of animals were analyzed using WinNonlin (professional edition, version 5.2) software, a non-compartmental model was used for concentration analysis, and the pharmacokinetic parameters of the test compounds were calculated.

Three adult male beagle dogs were fasted overnight before test. The test drugs were each suspended in a solution of 0.5% methylcellulose (MC) and 0.1% SDS in deionized water (w/w/v), and the suspension, each at a concentration of 1 mg/mL, was administered intragastrically at 5 mL/kg. Blood was collected 15 min, 30 min, 1 h, 2 h, 4 h, 6 h, 8 h and 24 h after administration. Animals were lightly anesthetized with chloral hydrate, and approximately 0.5 mL of whole blood was collected from the forelimb vein using a glass blood collection tube and placed in a heparin anticoagulant tube. The sample was centrifuged at 4° C./4200 rpm for 5 min. All plasma samples were stored in a refrigerator at −80±15° C. prior to analysis. An LC-MS/MS (Waters I Class UPLC-Xevo TQD tandem mass spectrometry) assay for the compounds was established prior to sample analysis. The collected plasma was quantitatively analyzed, plasma concentration-time data of animals were analyzed using WinNonlin (professional edition, version 5.2) software, a non-compartmental model was used for concentration analysis, and the pharmacokinetic parameters of the test compounds were calculated.

(2) Results

Compound A-10-10 (administered intragastrically, 5 mg/kg) showed good absorption with $C_{max}$ of 8323 ng/mL and 641 ng/mL in rat and beagle dog respectively, and it had a fairly high blood exposure ($AUC_{0-INF}$=73318 hr*ng/mL and 14867 hr*ng/mL).

TABLE 3

Pharmacokinetic data for rat/beagle (male) subjected to intragastric administration (5 mg/kg) ($t_{1/2}$: half life; $T_{max}$: peak time; $C_{max}$: maximum plasma concentration; $AUC_{0-INF}$: area under 0-INF time-concentration curve)

| PK parameters | Unit | Compound A-10-10 (p.o., 5 mg/kg) | |
| --- | --- | --- | --- |
| | | Rat | Dog |
| $t_{1/2}$ | hr | 3.74 | 14.2 |
| $T_{max}$ | hr | 2.00 | 8.00 |
| $C_{max}$ | ng/mL | 8323 | 641 |
| $AUC_{0-INF}$ | hr*ng/mL | 73318 | 14867 |

4. pBTK Inhibition Experiment on HEK293 Cells Transfected with BTK(wt) and BTK(C481S)

The major cause of the drug resistance to ibrutinib lies in C481S mutation of BTK kinase, and developing a BTK inhibitor which can effectively inhibit cells with BTK (C481S) variation is of great significance for overcoming the drug resistance to ibrutinib.

(1) Method

HEK293 human embryonic kidney cells were transiently transfected with human full-length BTK or BTK (C481S) vector.

Cells were dispensed into a 96-well plate at a predetermined cell density.

Each test compound was subjected to 3-fold serial dilution for eight times with 100% DMSO.

The compound was then diluted in tissue culture medium to 10-fold final assay concentration and 5% DMSO.

The compound was added to cells in the %-well plate (10-fold dilution in culture medium) and the final concentration was 1× compound and 0.5% DMSO. For positive (high signal) controls, cells were treated with 0.5% DMSO alone. For negative (low signal) controls, cells were treated with 20 μM ibrutinib, and the final concentration was 0.5% DMSO.

Cells were incubated with the compounds for 2 h at 37° C.

The cells were lysed and the lysate was transferred to an ELISA plate previously coated with an antibody that captures the substrate (human BTK or BTK(C481S)).

The plate was washed and then incubated with HRP-linked antibody to detect total tyrosine phosphorylation.

The plate was washed and then added with HRP substrate. The absorbance was read at 450 nm.

Based on the absorbance readings of the positive and negative control values, the % inhibition value was calculated according to the following formula: (% INH=((positive control−sample)/(positive control−negative control))−100.

The Z' value was calculated based on the following formula 1−((3×standard deviation of positive+3×standard deviation of negative)/(mean positive−mean negative)).

The logarithm of % inhibition value vs. compound concentration was plotted using GraphPad Prism.

$IC_{50}$ values were determined after sigmoidal dose-response curve fitting.

(2) Results

The C481S mutation reduces the inhibition of ibrutinib against BTK phosphorylation of HEK293 cells from 0.021 μM to 1.58 μM, while the compound A-10-10 disclosed herein has strong inhibition (0.077 μM) against HEK293 cells transfected with BTK(wt) and even stronger inhibition (0.066 μM) against HEK293 cells transfected with BTK (C481S).

TABLE 4

Inhibition values of pBTK ($IC_{50}$) against HEK293 cells transfected with BTK (wt) and BTK (C481S)

| | Transfected in HEK293 cells | |
| --- | --- | --- |
| Inhibitors | BTK (wt) pBTK $IC_{50}$ (μM) | BTK (C481S) pBTK $IC_{50}$ (μM) |
| A-10-10 | 0.077 | 0.063 |
| Ibrutinib | 0.021 | 1.58 |

5. Pharmacodynamic Experiment 1

(1) Method

CB17/SCID female mice with serious immune deficiency were purchased from Beijing Vital River Laboratory Animal Technology Co., Ltd. and bred in SPF animal houses. Human OCI-LY10 cells (Shanghai Junrui-UFBN0102) were cultured in an RPMI 1640 culture medium containing 10% fetal bovine serum, 100 U/mL penicillin and 100 μg/mL streptomycin through monolayer culture in vitro in an incubator (37° C. 5% $CO_2$). Routine treatment was performed twice a week for passaging. At a cell saturation of 80%-90% and a required number, the cells were harvested and counted, 0.2 mL ($1\times10^7$) of OCI-LY10 cells (together with matrigel at a volume ratio of 1:1) were subcutaneously inoculated into the right back of each mouse, and the tumor size could be measured about one week after inoculation. Tumor size was measured using a vernier caliper and tumor volume was calculated using the following formula: tumor volume= (length×width$^2$)/2. When the mean tumor volume reached 109 mm$^3$, the mice were divided into four groups (8 mice per group) for administration. i.e., vehicle (5% DMSO+20% HP-β-CD) control group, ibrutinib intragastric administration group (25 mg/kg, once/day), and compound A-10-10 intragastric administration group (25 mg/kg, 50 mg/kg, twice/day). Ibrutinib or compound A-10-10 was dissolved in 5% DMSO+20% HP-β-CD and administered intragastrically at 10 mL/kg for 28 consecutive days.

(2) Results

Compound A-10-10 and ibrutinib showed extremely strong anti-tumor activity in OCI-LY10 xenograft tumor model (FIG. 1). The compound A-10-10 intragastrically administered (the dosage was 25 mg/kg, bid; 50 mg/kg, bid) could significantly inhibit the growth of the diffuse large B-cell lymphoma cell strain OCI-LY10 (TGI=110%, 110%; p<0.001, p<0.001). After 21 days of administration, all OCI-LY10 xenograft tumors completely disappeared in the 50 mg/kg group. After 28 days of administration, all OCI-LY10 xenograft tumors also disappeared completely in the 25 mg/kg group. At day 28, the TGI value for the control compound ibrutinib 25 mg/kg group was 94% (p<0.001).

The effect of the test substance on body weight of tumor-bearing mice is shown in FIG. 1. The tumor-bearing mice showed good tolerance to the test drug A-10-10 at all dosages, and no significant weight loss was observed in all treatment groups.

6. Pharmacodynamic Experiment 2

(1) Method

CB17/SCID female mice with serious immune deficiency were purchased from Beijing Vital River Laboratory Animal Technology Co., Ltd. and bred in SPF animal houses. Human TMD-8 cells (Shanghai Junrui-UFBN1682) were cultured in an RPMI 1640 culture medium containing 10% fetal bovine serum, 100 U/mL penicillin and 100 μg/mL streptomycin through monolayer culture in vitro in an incubator (37° C., 5% $CO_2$). Routine treatment was performed twice a week for passaging. At a cell saturation of 80%-90% and a required number, the cells were harvested and counted, 0.2 mL ($1\times10^7$) of TMD-8 cells (together with matrigel at a volume ratio of 1:1) were subcutaneously inoculated into the right back of each mouse, and the tumor size could be measured about one week after inoculation. Tumor size was measured using a vernier caliper and tumor volume was calculated using the following formula: tumor volume (length×width=)/2. When the mean tumor volume reached 107 $mm^3$, the mice were divided into four groups (8 mice per group) for administration, i.e., vehicle (5% DMSO+20% HP-β-CD) control group, ibrutinib intragastric administration group (25 mg/kg, once/day), and compound A-10-10 intragastric administration group (25 mg/kg, 50 mg/kg, twice/day). Ibrutinib or compound A-10-10 was dissolved in 5% DMSO+20% HP-β-CD and administered intragastrically at 10 mL % kg for 27 consecutive days.

(2) Results

Figure 2:
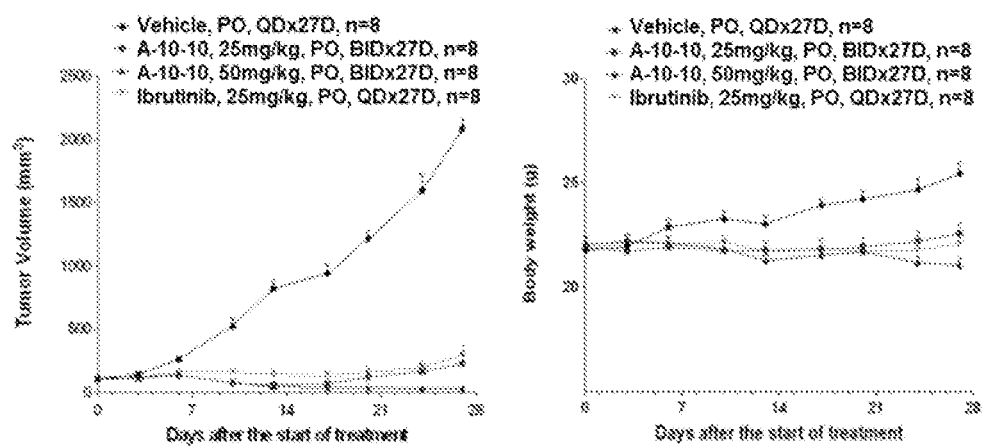
FIG. 2 is a TMD-8 xenograft tumor model.

Compound A-10-10 and ibrutinib showed extremely strong anti-tumor activity in TMD-8 xenograft tumor model (FIG. 2). The compound A-10-10 intragastrically administered (the dosage was 25 mg/kg, bid; 50 mg/kg, bid) could significantly inhibit the growth of the diffuse large B-cell lymphoma cell strain TMD-8 (TGI=94%, 104%; p<0.001, p<0.00). After 27 days of administration, ⅝ of the TMD-8 xenograft tumors disappeared in the 50 mg/kg group. The TGI value for the control compound ibrutinib 25 mg/kg group was 90% (p<0.001).

The effect of the test substance on body weight of tumor-bearing mice is shown in FIG. 2. The tumor-bearing mice showed good tolerance to the test drug A-10-10 at all dosages, and no significant weight loss was observed in all treatment groups.

What is claimed is:

1. A compound of formula I

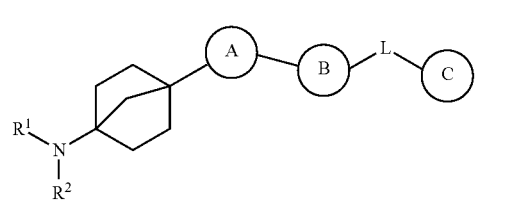

or a pharmaceutically acceptable salt, a solvate, a polymorph, an ester, or an optical isomer thereof, wherein ring A is selected from one of the following structures:

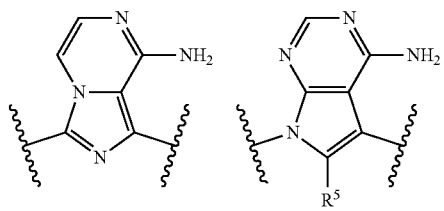

$R^5$ is hydrogen;
ring B is a substituted or unsubstituted aromatic ring or heteroaromatic ring; ring C is a substituted or unsubstituted aromatic ring or heteroaromatic ring;
L is a single bond or one of the following structures:

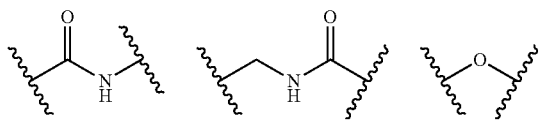

$R^1$ is selected from $R^3$ or one of the following structures:

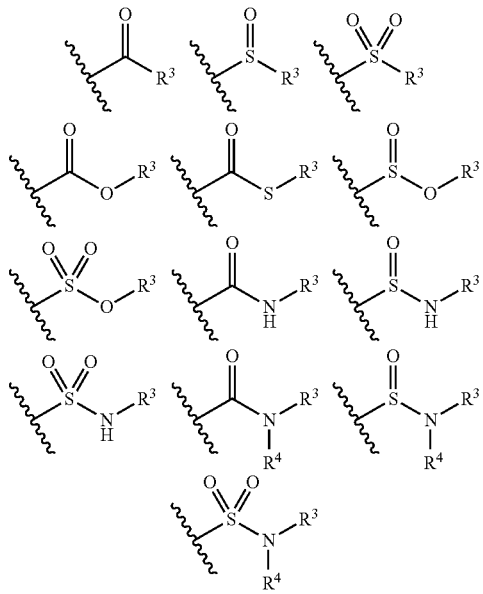

wherein R³ being selected from hydrogen, substituted or unsubstituted C₁₋₆ alkyl, substituted or unsubstituted C₁₋₆ alkynyl, substituted or unsubstituted C₁₋₆ alkenyl, substituted or unsubstituted C₆₋₁₀ aryl, substituted or unsubstituted C₁₋₉ heteroaryl, substituted or unsubstituted C₃₋₇ cycloalkyl, substituted or unsubstituted C₂₋₇ heterocycloalkyl;

R⁴ being selected from hydrogen, substituted or unsubstituted C₁₋₆ alkyl, substituted or unsubstituted C₆₋₁₀ aryl, substituted or unsubstituted C₁₋₉ heteroaryl, substituted or unsubstituted C₃₋₇ cycloalkyl, substituted or unsubstituted C₃₋₇ heterocycloalkyl;

R² is selected from H, substituted or unsubstituted C₁₋₃ alkyl, substituted or unsubstituted C₃₋₇ cycloalkyl, substituted or unsubstituted C₂₋₇ heterocycloalkyl, substituted or unsubstituted C₆₋₁₀ aryl, or substituted or unsubstituted C₁₋₉ heteroaryl; and wherein R¹ and R², along with N attached thereto, may optionally form a substituted or unsubstituted C₂₋₇ heterocyclic ring and R³ and R⁴, along with N attached thereto, may optionally form a C₃₋₇ heterocyclylamino or a C₃₋₉ heteroarylamino.

2. The compound according to claim 1, wherein for R³, a substituent of the substituted C₁₋₆ alkyl, the substituted C₁₋₆ alkynyl, the substituted C₁₋₆ alkenyl, the substituted C₆₋₁₀ aryl, the substituted C₁₋₉ heteroaryl, the substituted C₃₋₇ cycloalkyl, the substituted C₂₋₇ heterocycloalkyl is selected from one or more of halogen, cyano, hydroxyl, amino, substituted or unsubstituted acylamino, substituted or unsubstituted aminoacyl, substituted or unsubstituted C₁₋₄ alkyl, substituted or unsubstituted C₃₋₇ cycloalkyl, substituted or unsubstituted C₃₋₇ cycloalkoxy, substituted or unsubstituted C₁₋₄ alkylamino, di[substituted or unsubstituted C₁₋₄ alkyl] amino, substituted or unsubstituted C₃₋₇ cycloalkylamino, substituted or unsubstituted C₃₋₇ heterocycloalkylamino, substituted or unsubstituted C₁₋₃ alkoxy, substituted or unsubstituted C₃₋₇ cycloalkoxy, substituted or unsubstituted C₆₋₁₀ aryl, or substituted or unsubstituted C₃₋₇ heterocycloalkyl.

3. The compound according to claim 1, wherein for R⁴, a substituent of the substituted C₁₋₆ alkyl, the substituted C₆₋₁₀ aryl, the substituted C₁₋₉ heteroaryl, the substituted C₃₋₇ cycloalkyl, the substituted C₃₋₇ heterocycloalkyl is selected from one or more of halogen, hydroxyl, cyano, amino, substituted or unsubstituted C₁₋₄ alkenyl, substituted or unsubstituted C₃₋₇ cycloalkyl, substituted or unsubstituted C₃₋₇ cycloalkoxy, substituted or unsubstituted C₁₋₄ alkylamino, di[substituted or unsubstituted C₁₋₄ alkyl]amino, substituted or unsubstituted C₃₋₇ cycloalkylamino, substituted or unsubstituted C₃₋₇ heterocycloalkylamino, substituted or unsubstituted C₁₋₃ alkoxy, substituted or unsubstituted C₃₋₇ cycloalkoxy, substituted or unsubstituted C₆₋₁₀ aryl, or substituted or unsubstituted C₃₋₇ heterocycloalkyl.

4. The compound according to claim 1, wherein for ring B, a substituent of the substituted aromatic ring or heteroaromatic ring is selected from one or more of halogen, hydroxyl, cyano, amino, C₁₋₃ alkyl, C₁₋₃ alkoxy, C₁₋₃ alkylamino, C₁₋₃ haloalkyl, C₁₋₃ haloalkoxy.

5. The compound according to claim 1, wherein for ring C, a substituent of the substituted aromatic ring or heteroaromatic ring is selected from one or more of halogen, hydroxyl, cyano, amino, C₁₋₃ alkyl, C₁₋₃ alkoxy, C₁₋₃ alkylamino, C₁₋₃ haloalkyl, C₁₋₃ haloalkoxy.

6. The compound according to claim 1, wherein ring B is selected from one of the following structures:

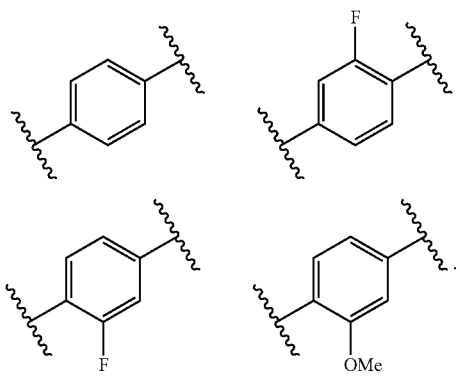

7. The compound according to claim 1, wherein ring C is selected from one of the following structures:

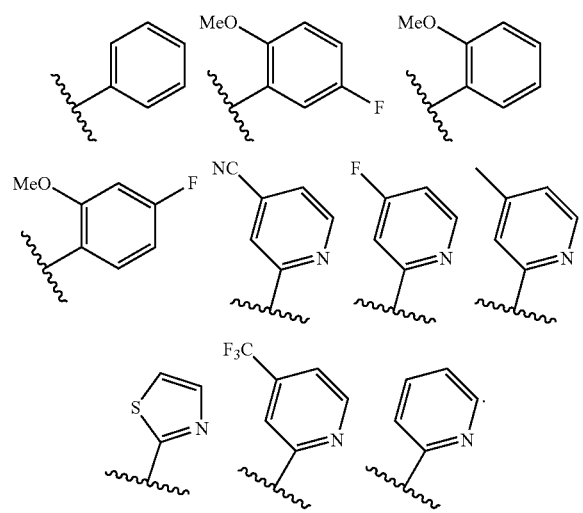

8. The compound according to claim 1, wherein R¹ is selected from one of the following structures:

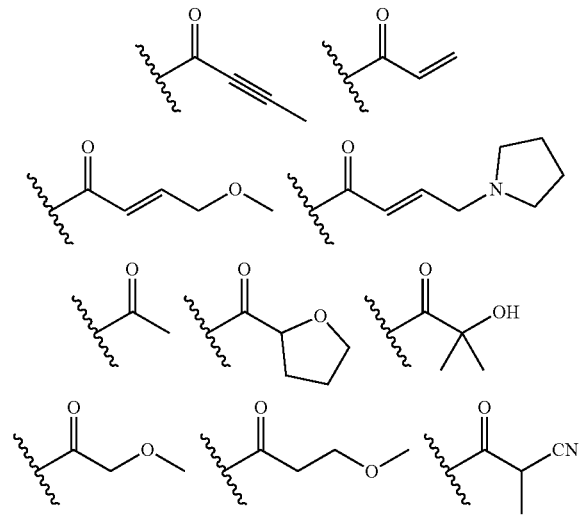

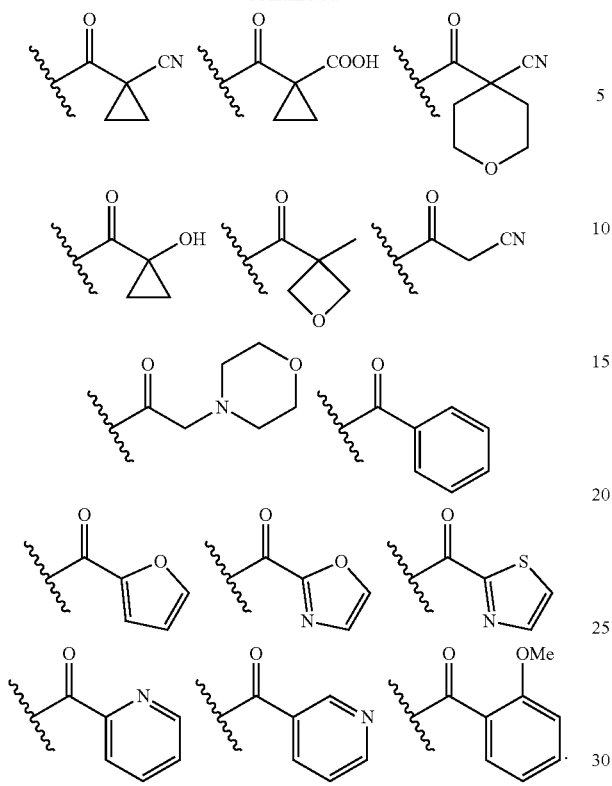

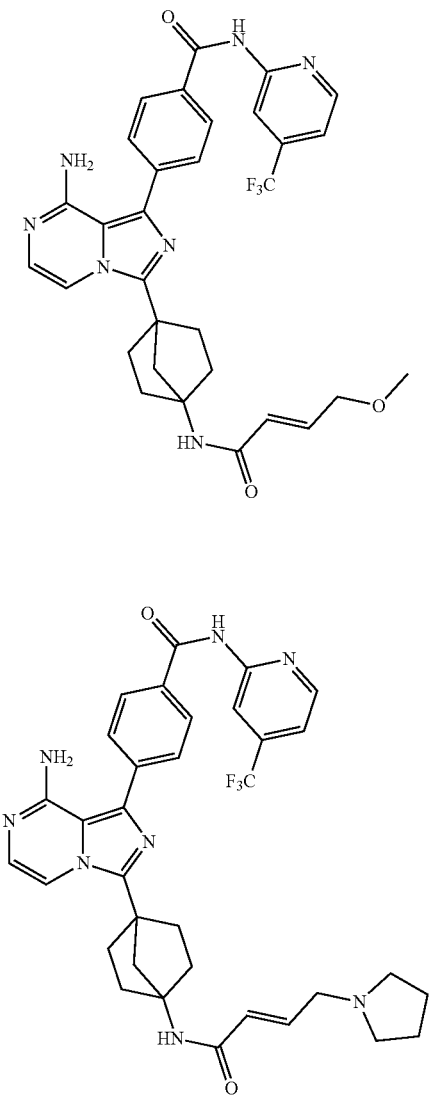

9. The compound according to claim 1, wherein $R^2$ is selected from H, and $R^1$ is selected from:

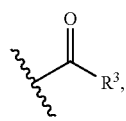

wherein $R^3$ is selected from hydrogen, substituted or unsubstituted $C_{1-6}$ alkyl, substituted or unsubstituted $C_{1-6}$ alkynyl, substituted or unsubstituted $C_{1-6}$ alkenyl, substituted or unsubstituted $C_{6-10}$ aryl, substituted or unsubstituted $C_{1-9}$ heteroaryl, substituted or unsubstituted $C_{3-7}$ cycloalkyl, substituted or unsubstituted $C_{2-7}$ heterocycloalkyl.

10. A compound of formula I

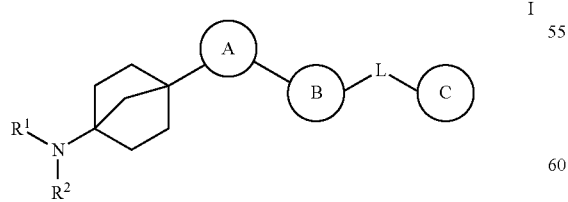

I or a pharmaceutically acceptable salt, a solvate, a polymorph, an ester, or an optical isomer thereof, wherein the compound is selected from any one of the following structures:

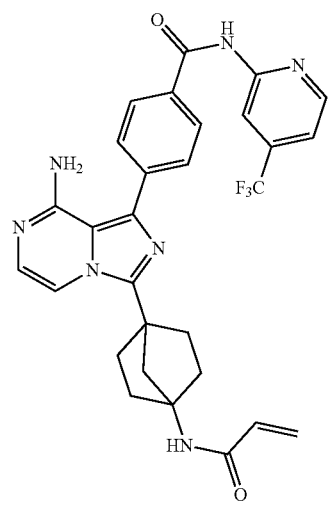

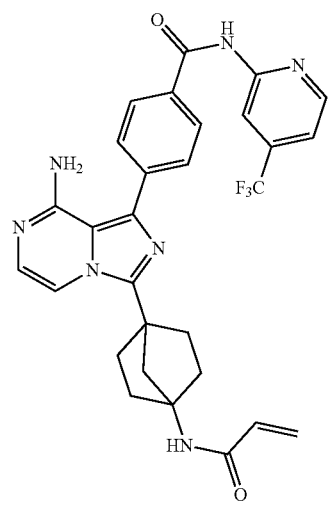

111
-continued
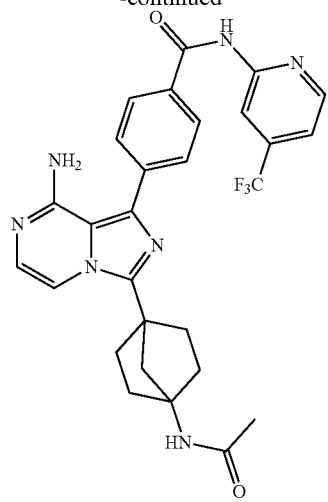
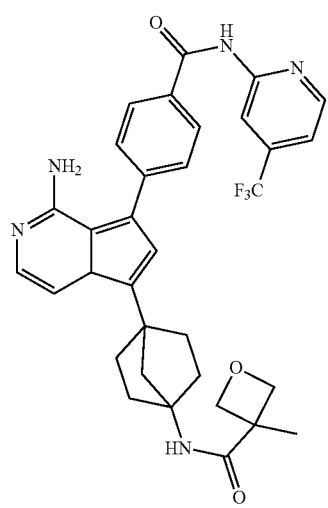
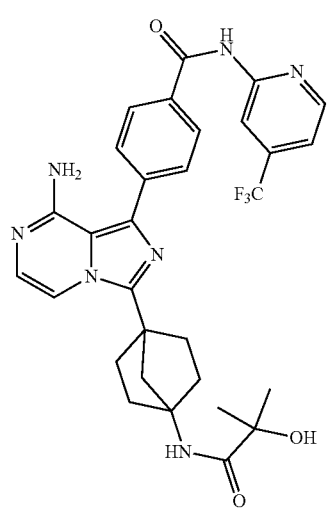
112
-continued
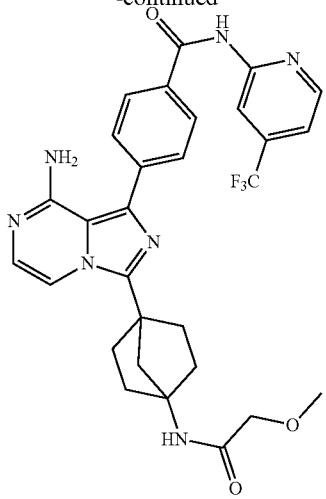
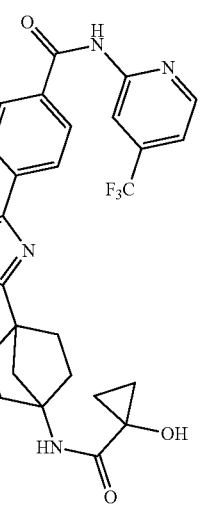

113
-continued
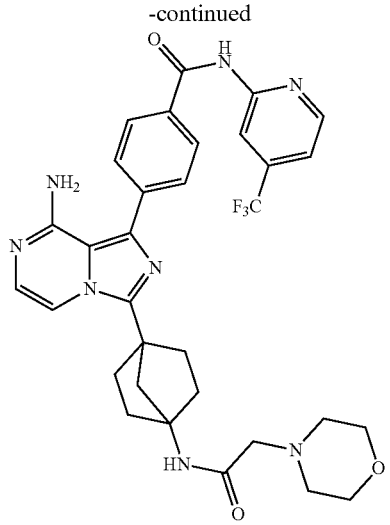
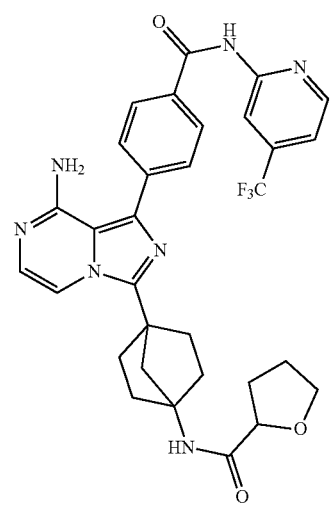
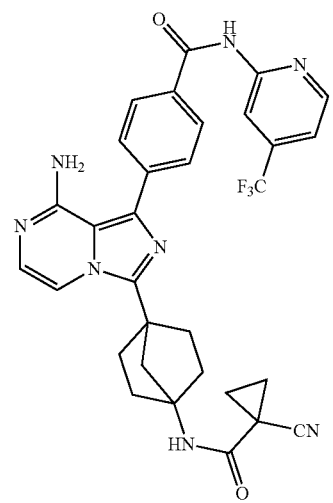
114
-continued
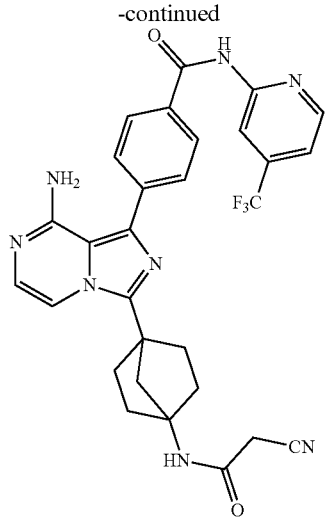
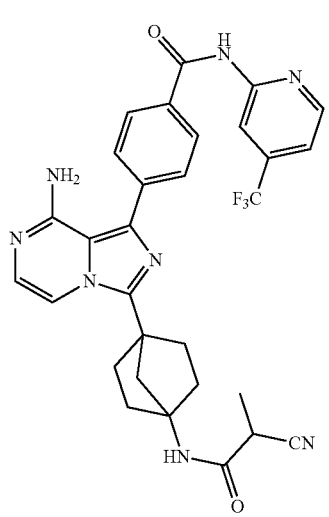
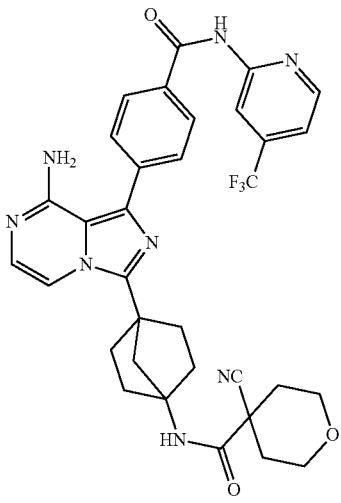

115
-continued
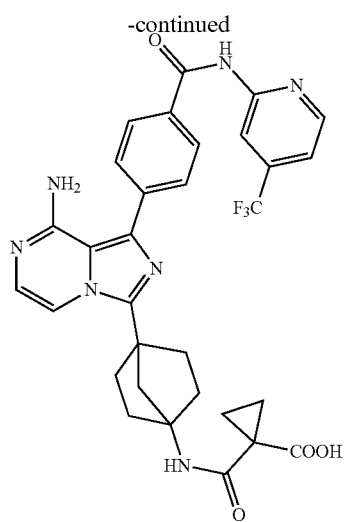
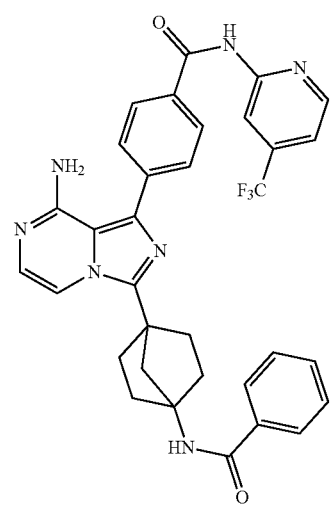
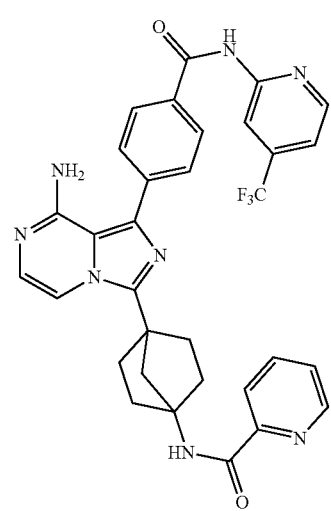
116
-continued
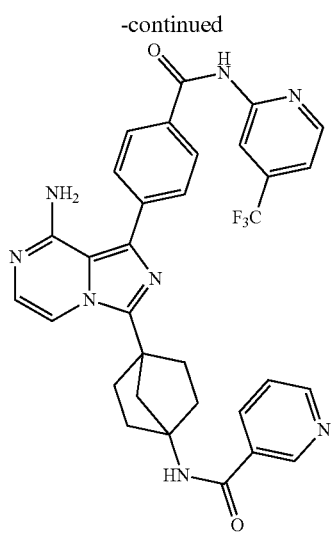
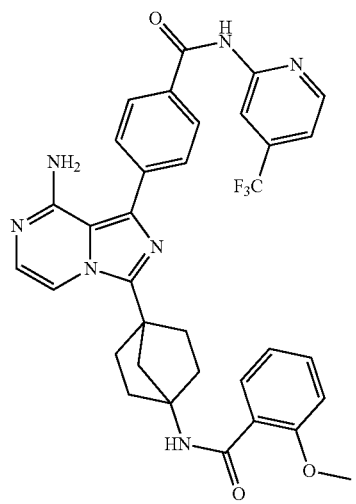
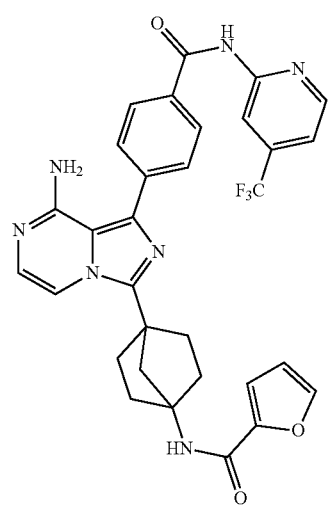

117
-continued
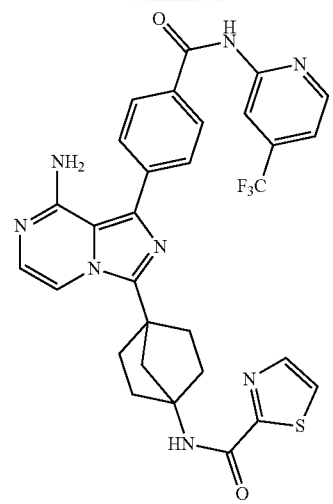
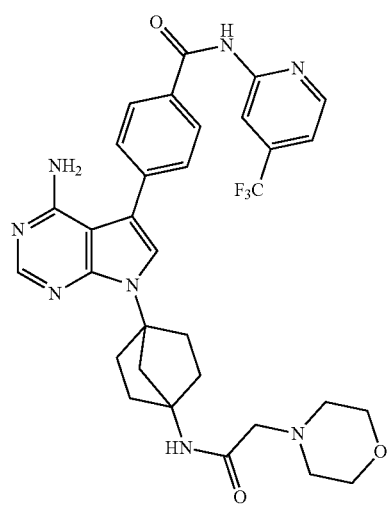
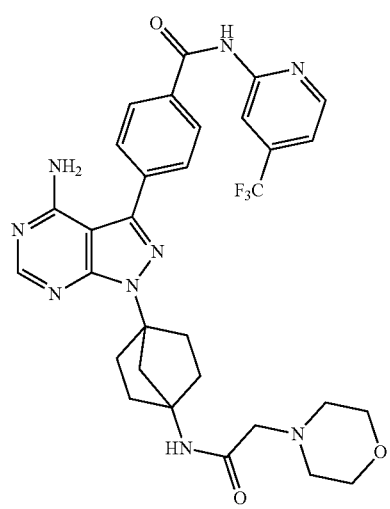
118
-continued
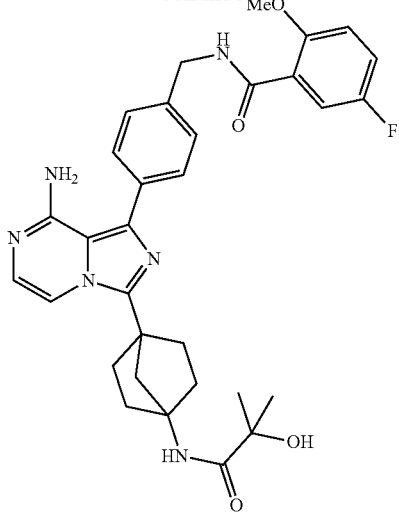
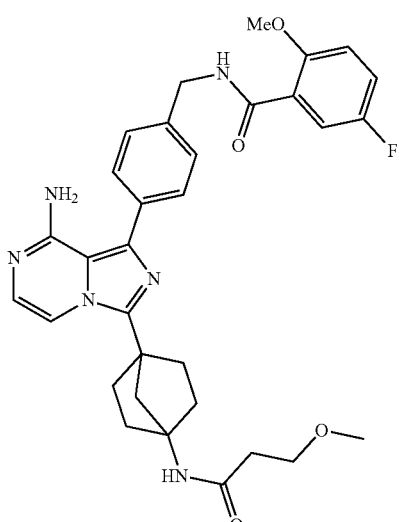
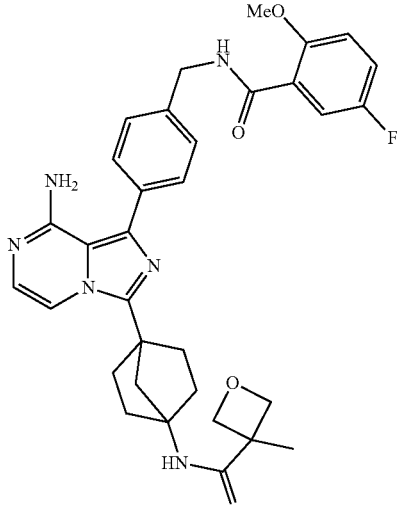

119
-continued
120
-continued
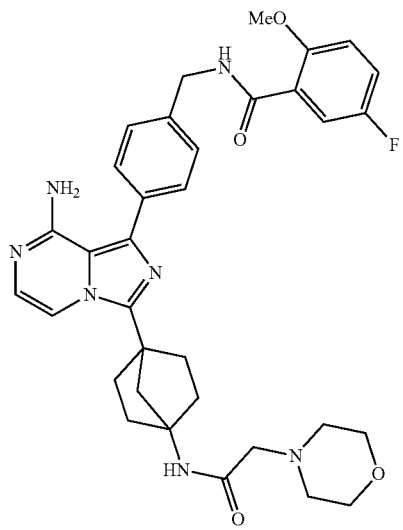
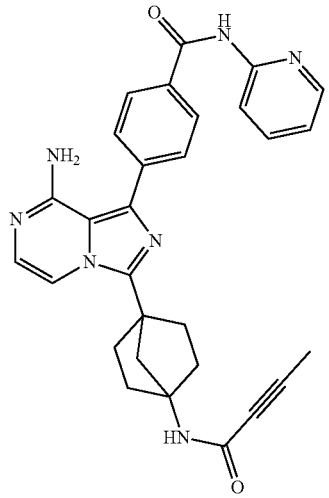
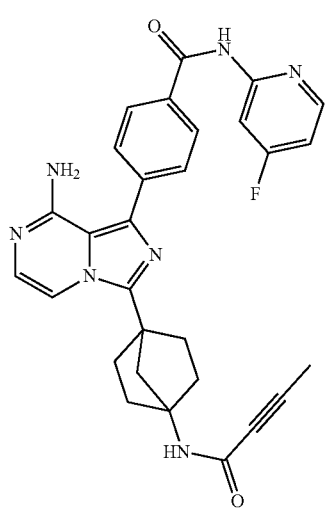
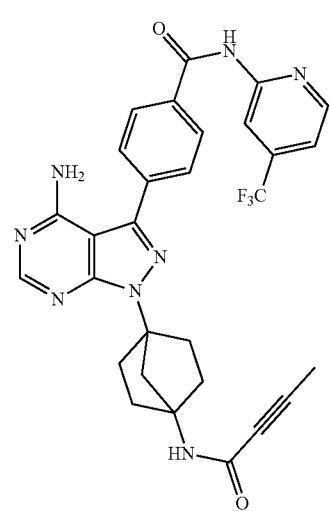

| 121 | 122 |
|---|---|
| -continued | -continued |
| 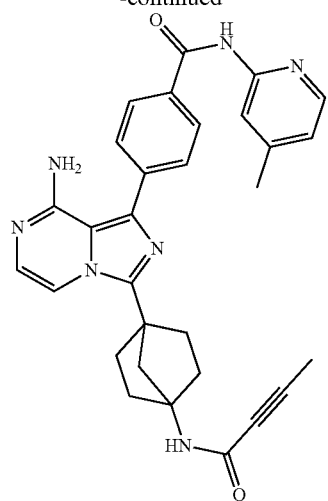 | 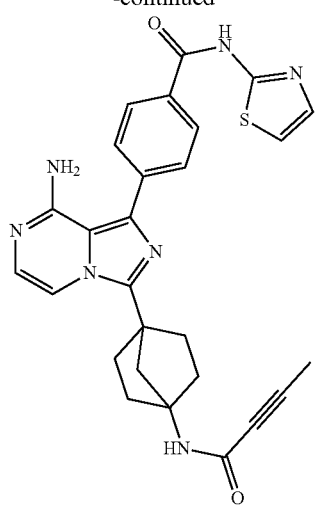 |
| 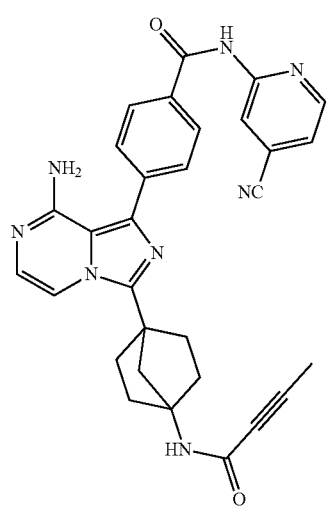 | 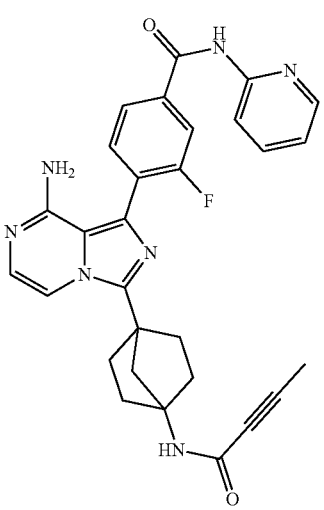 |
| 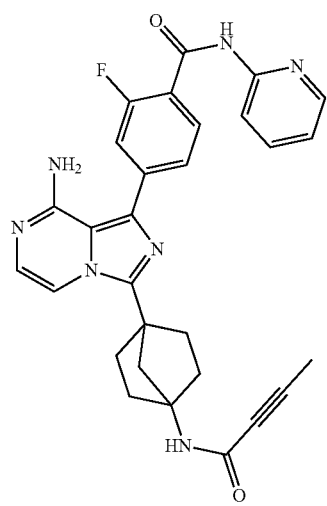 | 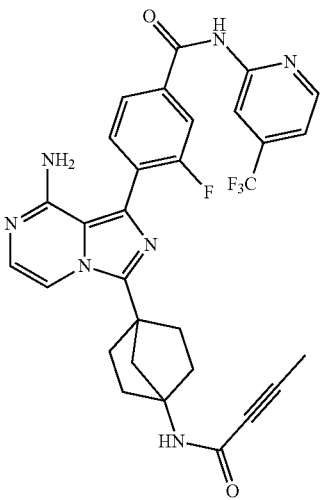 |

123
-continued
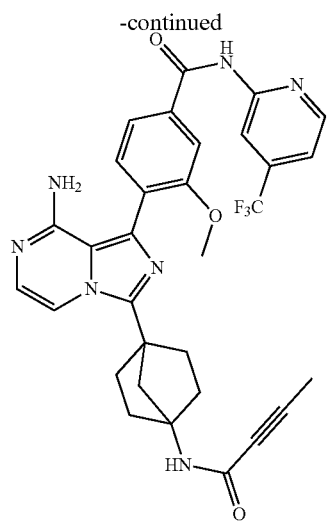
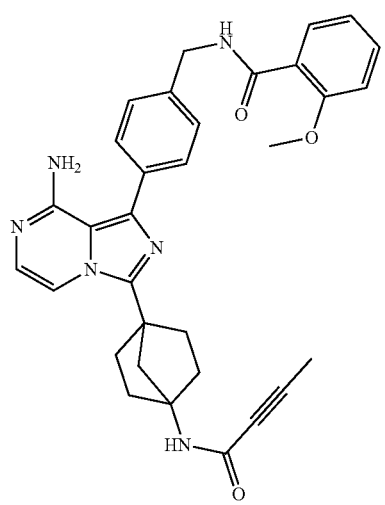
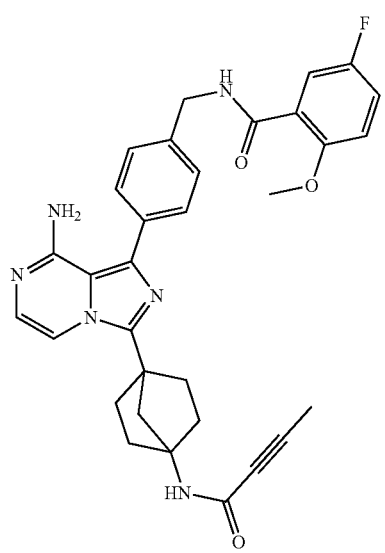
124
-continued
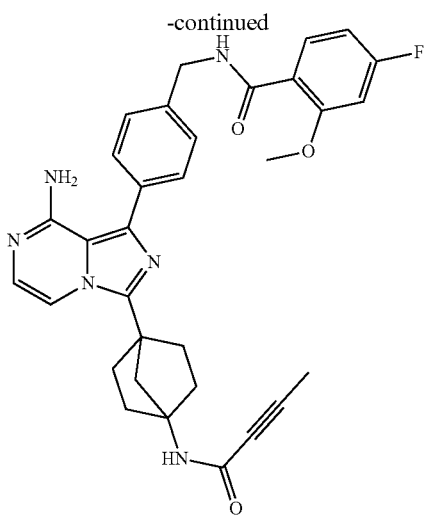
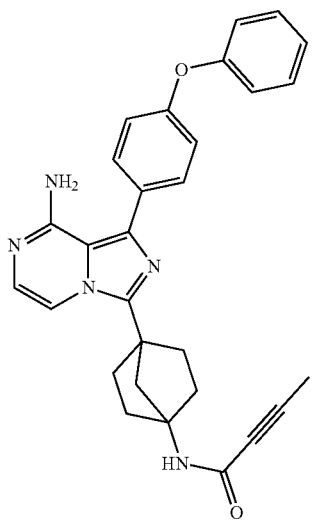
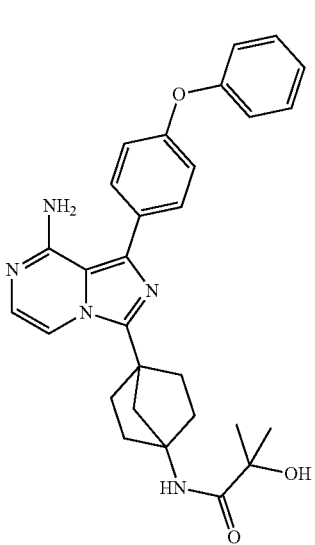

125
-continued
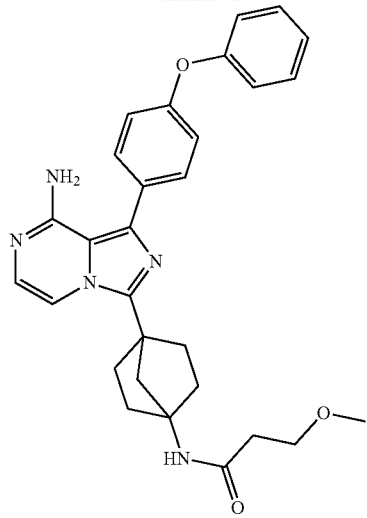
126
-continued
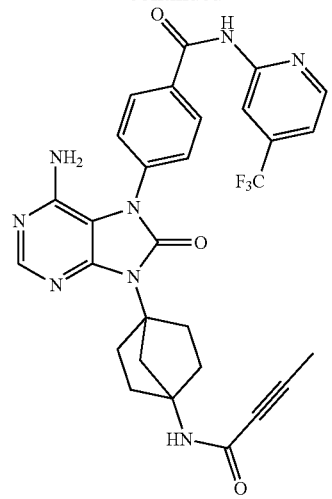
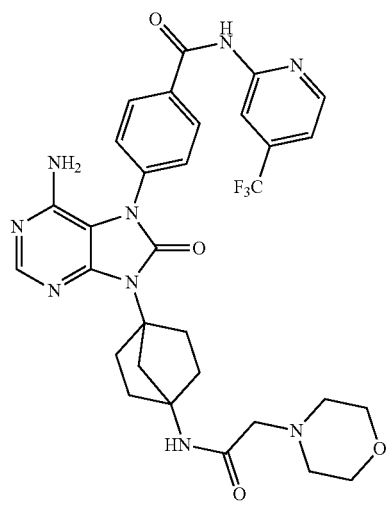
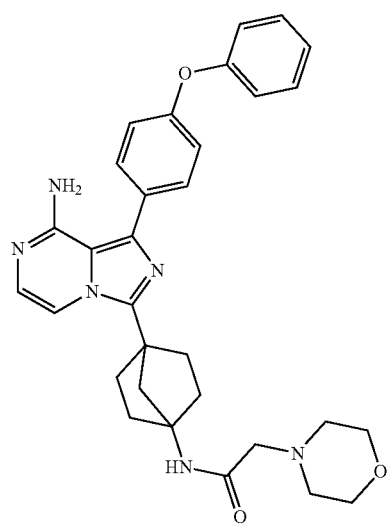

-continued

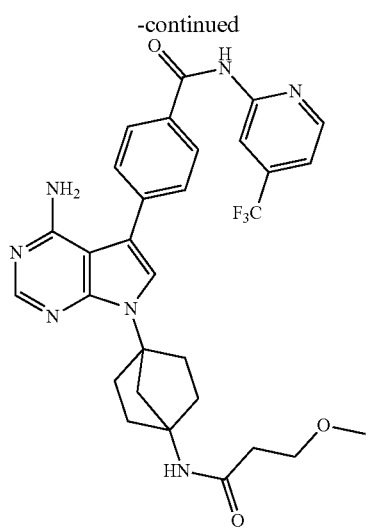

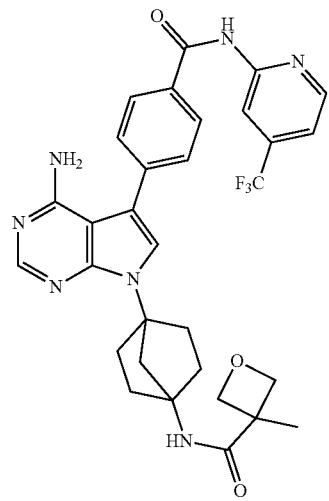

11. A pharmaceutical composition comprising the compound according to claim 1.

12. A manufacture method for the compound according to claim 1, comprising the steps as follows: (S1) performing Suzuki coupling of compound IIIA with boronic acid or borate II to give compound IV; (S2) converting the compound IV into the hydrochloride of compound V by removal of benzyloxycarbonyl with trifluoroacetic acid; (S3) coupling the compound V with an organic acid to give the compound I according to claim 1;

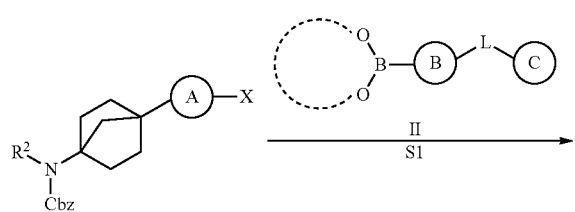

-continued

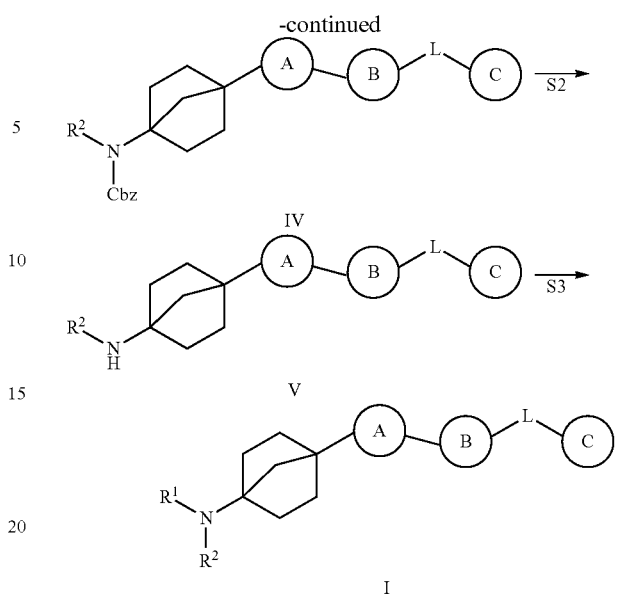

wherein X=halogen; $R^2$, $R^1$, L, ring A, ring B and ring C are described as in claim 1.

13. A manufacture method for the compound according to claim 1, comprising the steps as follows: (A1) converting compound IIIA into the hydrochloride of compound VI by removal of benzyloxycarbonyl with trifluoroacetic acid; (A2) coupling the compound VI with an organic acid to give compound VII; (A3) performing Suzuki coupling of the compound VII with boronic acid or borate II to give the compound I according to claim 1;

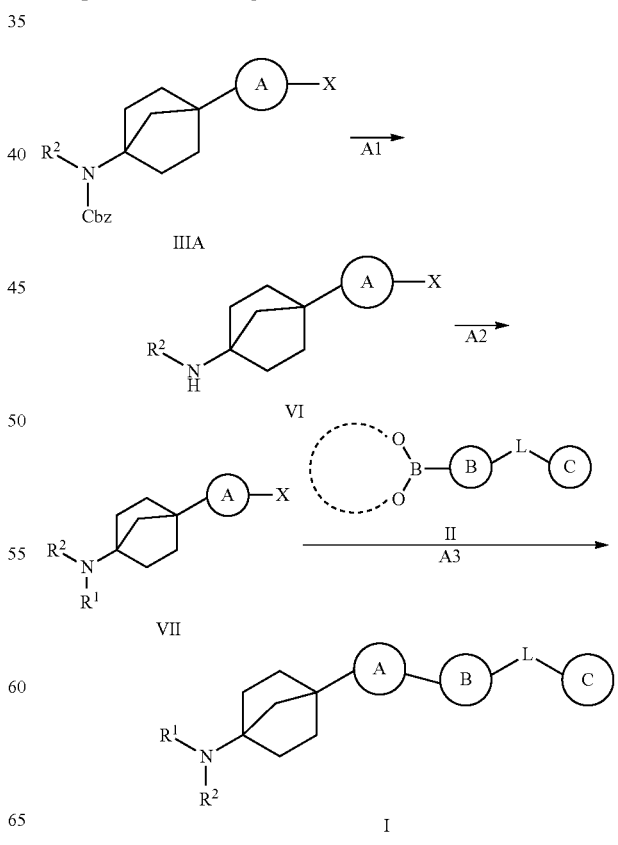

wherein X=halogen; $R^2$, $R^1$, L, ring A, ring B and ring C are described as in claim 1.

14. A manufacture method for the compound according to claim 1, comprising the steps as follows: (B1) performing Chan-Lam-Evans coupling of compound IIIB with boronic acid II in the presence of catalyzation of copper acetate to give compound VIII; (B2) converting the compound VIII into the hydrochloride of compound IX by removal of benzyloxycarbonyl with trifluoroacetic acid; (B3) coupling the compound IX with an organic acid to give the compound I according to claim 1;

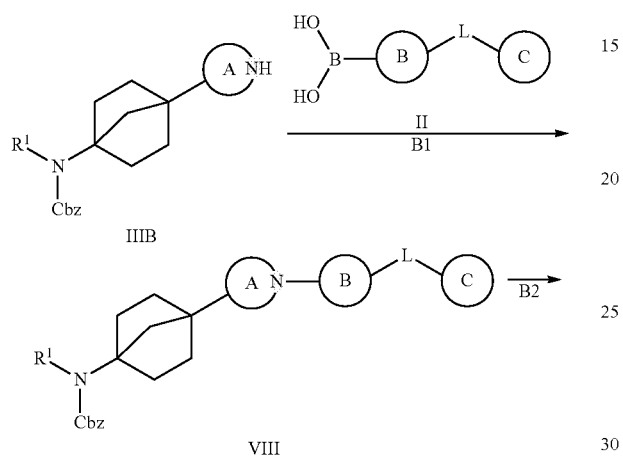

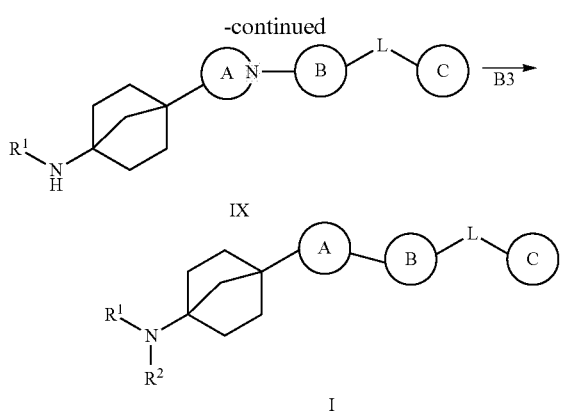

wherein $R^2$, $R^1$, L, ring A, ring B and ring C are described as in claim 1.

15. A method for treating a disease or a cancer, wherein the disease or the cancer is arthritis, asthma, systemic lupus erythematosus, chronic lymphocytic lymphoma, diffuse large cell lymphoma, follicular lymphoma, or chronic lymphocytic leukemia, comprising administering to a subject in need thereof an effective amount of the compound according to claim 1.

16. The method according to claim 15, wherein the disease or the cancer is associated with excessive activity of Bruton's tyrosine kinase, or the disease or the cancer is associated with aberrant B-cell proliferation.

* * * * *